(12) United States Patent
Skerra et al.

(10) Patent No.: US 7,585,940 B2
(45) Date of Patent: Sep. 8, 2009

(54) MUTEINS OF HUMAN TEAR LIPOCALIN

(75) Inventors: Arne Skerra, Freising (DE); Steffen Schlehuber, Langenbach (DE)

(73) Assignee: Pieris AG, Freising-Weihenstephan (DE)

( * ) Notice: Subject to any disclaimer, the term of this patent is extended or adjusted under 35 U.S.C. 154(b) by 336 days.

(21) Appl. No.: 10/569,134

(22) PCT Filed: Aug. 24, 2004

(86) PCT No.: PCT/EP2004/009447

§ 371 (c)(1),
(2), (4) Date: May 11, 2006

(87) PCT Pub. No.: WO2005/019256

PCT Pub. Date: Mar. 3, 2005

(65) Prior Publication Data

US 2007/0224633 A1    Sep. 27, 2007

(30) Foreign Application Priority Data

Aug. 25, 2003   (WO)   .................. PCT/EP03/09404

(51) Int. Cl.
*C07K 14/00* (2006.01)
(52) U.S. Cl. ................................... 530/350
(58) Field of Classification Search ................ None
See application file for complete search history.

(56) References Cited

FOREIGN PATENT DOCUMENTS

| DE | 44 17 598 A1 | 12/1998 |
|---|---|---|
| EP | 1 277 764 A | 1/2003 |
| WO | WO 99/16873 A | 4/1999 |
| WO | WO 00/75308 A1 | 12/2000 |
| WO | WO 01/75067 A | 10/2001 |
| WO | WO 02/090500 A | 11/2002 |
| WO | WO 03/029463 A | 4/2003 |
| WO | WO 03/029463 A2 | 4/2003 |
| WO | WO 03/029471 A1 | 4/2003 |

OTHER PUBLICATIONS

Gasymov et al. Biochemistry, 2001, 40: 14754-14762.*
Altschul et al., "Gapped BLAST and PSI-BLAST: a new generation of protein database search programs," Nucleic Acids Research, 1997, vol. 25, No. 17, pp. 3389-3402.
Amstutz et al., "In vitri display technologies; novel developments and applications," Current Opinion in Biotechnology, Aug. 1, 2001, vol. 12, issue 4, pp. 400-405 (Abstract, one page).
Bittker et al., "Nucleic acid evolution and minimization by nonhomologous random recombination," Nature Biotechnology, Oct. 2002, vol. 20, pp. 1024-1029.

(Continued)

*Primary Examiner*—Suzanne M. Noakes
(74) *Attorney, Agent, or Firm*—Foley & Lardner LLP

(57) ABSTRACT

The present invention relates to novel muteins derived from tear lipocalin or a homologue thereof. In particular, the invention relates to a mutein of human tear lipocalin. The invention also refers to a corresponding nucleic acid molecule encoding such a mutein and to a method for its generation. The invention further refers to a method for producing such a mutein. Finally, the invention is directed to a pharmaceutical composition comprising such a lipocalin mutein as well as to various use of the mutein.

8 Claims, 26 Drawing Sheets

```
              ***       ***
  1    HHLLAS DEEI   QDVSGTWYLK   AMTVDREFPE   MNLESVTPMT
          *  *  *                    *   *  **
 41    LT TLEGGNLE   AKVTMLISGR   CQEVKAVLEK   TDEPGKYTAD
               *   *   *  *
 81    GGKHVAYIIR   SHVKDHYIFY   CEGELHGKPV   RGVKLVGRDP

121    KNNLEALEDF   EKAAGARGLS   TESILIPRQS   ETCSPGSD   158
```

OTHER PUBLICATIONS

Bruckdorfer et al., "From Production of Peptides in Milligram Amounts for Research to Multi-Tons Quantities for Drugs of the Future," Current Phramaceutical Biotechnology, 2004, vol. 5, pp. 29-43.

Flower, Darren R., "The lipocalin protein family: structure and function," Biochem. J., 1996, vol. 318, pp. 1-14.

Flower et al., "The lipocalin protein family: structural and sequence overview," Biochimica et Biophysica Acta (BBA), Oct. 18, 2000, vol. 1482, issues 1-2, pp. 9-24 (Abstract, two pages).

Gasymov et al., "Binding studies of tear lipocalin: the role of the conserved tryptophan in maintaining structure, stability and ligand affinity," Biochimica et Biophysica Acta, 1999, vol. 1433, pp. 307-320.

Glasgow et al., "Tear lipocalins bind a broad array of lipid ligands," Curr. Eye Res., May 1995, vol. 14, No. 5, pp. 363-372 (Abstract, one page).

Jung et al., "Target Cell-restricted Triggering of the CD95 (APO-1/Fas) Death Receptor with Bispecific Antibody Fragments," Cancer Research, Mar. 1, 2001, vol. 61, pp. 1846-1848.

Kraulis et al., "The serum albumin-binding domain of streptococcal protein G is a three-helical bundle: a heteronuclear NMR study," FEBS Letters, 1996, vol. 378, pp. 190-194.

Lechner et al., "Human tear lipocalin acts as an oxidative-stress-induced scavenger of potentially harmful lipid peroxidation products in a cell culture system," Biochem. J., 2001, vol. 356, pp. 129-135.

Lowman, H.B., "Bacteriophage display and discovery of peptide leads for drug development," Annu. Rev. Biophys. Biomol. Struct., 1997, vol. 26, pp. 401-424.

Murakami et al., "Random insertion and deletion of arbitrary number of bases for codon-based random mutation of DNAs," Nature Biotechnology, 2002, vol. 20, pp. 76-81 (Abstract, one page).

Paesen et al., "Tick Histamine-Binding Proteins: Isolation, Cloning and Three-Dimensional Structure," Molecular Cell, May 1999, vol. 3, pp. 661-671.

Pervaiz et al., "Homology and structure-function correlations between $\alpha_1$-acid glycoprotein and serum retinol-binding protein and its relatives," FASEB J., 1987, vol. 1, pp. 209-214.

Pini et al., "Phage Display and Colony Filter Screening for High-Throughput Selection of Antibody Libraries," Combinatorial Chemistry & High Throughput Screening, 2002, vol. 5, No. 7, 1 pg.

Redl, Bernhard, "Human tear lipocalin," Biochimica et Biophysica Acta, 2000, vol. 1482, pp. 241-248.

Redl et al., "cDNA Cloning and Sequencing Reveals Human Tear Prealbumin to Be a Member of the Lipophilic-ligand Carrier Protein Superfamily," J. Biol. Chem., Oct. 5, 1992, vol. 267, No. 28, pp. 20282-20287.

Rodi et al., "Phage-display technology—finding a needle in a vast molecular haystack," Curr. Opin. Biotechnol., Feb. 1999, vol. 10, No. 1, pp. 87-93 (Abstract, one page).

Sangamnatdej et al., "A high affinity serotonin- and histamine-binding lipocalin from tick saliva," Insect Molecular Biology, Feb. 2002, vol. 11, p. 79 (Abstract, one page).

Schlehuber et al., "Tuning ligand affinity, specificity, and folding stability of an engineered lipocalin variant—a so-called 'anticalin' —using a molecular random approach," Biophysical Chemistry, May 2, 2002, vol. 96, issues 2-3, pp. 213-228 (Abstract, one page).

Schlehuber et al., "Duocalins: Engineered Ligand-Binding Proteins with Dual Specificity Derived from the Lipocalin Fold," Biol. Chem., Sep. 2001, vol. 382, pp. 1335-1342.

Schlehuber et al., "A Novel Type of Receptor Protein, Based on the Lipocalin Scaffold, with Specificity for Digoxigenin," J. Mol. Biol., 2000, vol. 297, pp. 1105-1120.

Schmidt et al., "Molecular Interaction Between the Strep-tag Affinity Peptide and its Cognate Target, Streptavidin," J. Mol. Biol., 1996, vol. 255, pp. 753-766.

Skerra, Arne, "Anticalins': a new class of engineered ligand-binding proteins with antobidy-like properties," Reviews in Molecular Biotechnology, 2001, vol. 74, pp. 257-275.

Skerra, Arne, "Lipocalins as a scaffold," Biochimica et Biophysica Acta, 2000, vol. 1492, pp. 337-350.

Van't Hof et al., "The Salivary Lipocalin Von Ebner's Gland Protein Is a Cysteine Proteinase Inhibitor," J. Biol. Chem., Jan. 17, 1997, vol. 272, no. 3, pp. 1837-1841.

Wang et al., "Expanding the Genetic Code of Escherichia coli," Science, Apr. 20, 2001, vol. 292, pp. 498-500.

Wang et al., "Expanding the genetic code," Chem. Commun., 2002, pp. 1-11.

Wilson et al., "The use of mRNA display to select high-affinity protein-binding peptides," PNAS, Mar. 27, 2001, vol. 98, No. 7, pp. 3750-3755.

Yusifov et al., "Endonuclease activity in lipocalins," Biochem. J., 2000, vol. 347, pp. 815-819.

Zaccalo et al., "An Approach to Random Mutagenesis of DNA Using Mixtures of Triphosphate of Nucleoside Analogues," J. Mol. Biol., Feb. 2, 1996, vol. 255, issue 4, pp. 589-603.

Gasymov Oktay K et al., "Site-directed tryptophan fluorescence reveals the solution structure of tear lipocalin: Evidence for features that confer promiscuity in ligand binding", Biochemistry, vol. 40, No. 49, Dec. 11, 2001 pp. 14754-14762.

Gasymov Oktay K et al., "Resolving near-ultraviolet circular dichroism spectra of single trp mutants in tear lipocalin", Analytical Biochemistry, vol. 318, No. 2, Jul. 15, 2003, pp. 300-308.

Kock Kai et al., "Structural organization of the genes for rat von Ebner's gland proteins 1 and 2 reveals their close relationship to lipocalins", European Journal of Biochemistry, vol. 221, No. 3, 1994, pp. 905-916.

Wojnar Petra et al., "The N-terminal part of recombinant human tear lipocalin/von Ebner's gland protein confers cysteine proteinase inhibition depending on the presence of the entire cystatin-like sequence motifs", Biological Chemistry, vol. 382, No. 10, Oct. 2001, pp. 1515-1520.

Database EMBL 'Online!', Jan. 13, 2003, "Sus scrofa Von Ebner gland protein mRNA , complete cds", XP002312650, Whole document.

A Skerra, "Engineered Protein Scaffolds for Molecular Recognition", Journal of Molecular Recognition, vol. 13, No. 4, Jul. 2000, pp. 167-187.

Gasymov Oktak K et al., "Relaxation of beta-structure in tear lipocalin and enhancement of retinoid binding" IOVS, vol. 43, No. 10, Oct. 2002, pp. 3165-3173.

Database EMBL 'Online!' Feb. 3, 2004, "Sequence 17543 from patent W002068579", XP002321060.

Gasymov Oktay K et al., "Resolution of ligand positions by site-directed tryptophan fluorescence in tear lipocalin" Protein Science, vol. 9, No. 2, Feb. 2000, pp. 325-331.

Glasgow B J et al., "Side chain mobility and ligand interactions of the G strand of tear lipocalins by site-directed spin labeling" Biochemistry vol. 38, No. 41, Oct. 12, 1999, pp. 13707-13716.

\* cited by examiner

```
                 ***      ***
1      HHLLAS DEEI  QDVS GTWYLK  AMTVDREFPE  MNLESVTPMT
        *  *  *                        *    *  **
41     LT TLEGGNLE  AKVTMLISGR  CQEVKAVLEK  TDEPGKYTAD
          *    *   *
81     GGKHVA YIIR  SHVKDHYIFY  CEGELHGKPV  RGVKLVGRDP

121    KNNLEALEDF  EKAAGARGLS  TESILIPRQS  ETCSPGSD    158
```

1. PCR

2. PCR

SEQUENCE LISTING

```
<160> NUMBER OF SEQ ID NOS: 59

<210> SEQ ID NO 1
<211> LENGTH: 1123
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(1113)
<220> FEATURE:
<221> NAME/KEY: sig_peptide
<222> LOCATION: (22)..(84)
<220> FEATURE:
<221> NAME/KEY: mat_peptide
<222> LOCATION: (85)..(1113)
<220> FEATURE:
<221> NAME/KEY: misc_feature
<222> LOCATION: (541)..(543)
<223> OTHER INFORMATION: amber stop codon

<400> SEQUENCE: 1
tctagataac gagggcaaaa a atg aaa aag aca gct atc gcg att gca gtg     51
                        Met Lys Lys Thr Ala Ile Ala Ile Ala Val
```

-continued

```
                        -20                     -15
gct ctg gct ggc ttc gct acc gta gcc cag gcc gat gga gga gag gag      99
Ala Leu Ala Gly Phe Ala Thr Val Ala Gln Ala Asp Gly Gly Glu Glu
        -10                 -5              -1  1                 5 att cag gat gtg tca ggg acg tgg tat ctg aag gcg atg acg gtg gac     147
Ile Gln Asp Val Ser Gly Thr Trp Tyr Leu Lys Ala Met Thr Val Asp
                    10                  15                  20 agg gag ttc cct gag atg aat ctg gaa tcg gtg aca ccc atg acc ctc     195
Arg Glu Phe Pro Glu Met Asn Leu Glu Ser Val Thr Pro Met Thr Leu
                25                  30                  35 acg acc ctg gaa ggg ggc aac ctg gaa gcc aag gtc acc atg ctg ata     243
Thr Thr Leu Glu Gly Gly Asn Leu Glu Ala Lys Val Thr Met Leu Ile
            40                  45                  50 agt ggc cgg tgc cag gag gtg aag gcc gtc ctg gag aaa act gac gag     291
Ser Gly Arg Cys Gln Glu Val Lys Ala Val Leu Glu Lys Thr Asp Glu
        55                  60                  65 ccg gga aaa tac acg gcc gac ggg ggc aag cac gtg gca tac atc atc     339
Pro Gly Lys Tyr Thr Ala Asp Gly Gly Lys His Val Ala Tyr Ile Ile
 70                  75                  80                  85 agg tcg cac gtg aag gac cac tac atc ttt tac tct gag ggc cag ctc     387
Arg Ser His Val Lys Asp His Tyr Ile Phe Tyr Ser Glu Gly Gln Leu
                90                  95                 100 cat ggg aag ccg gtc cga ggg gtg aag ctc gtg ggc aga gac ccc aag     435
His Gly Lys Pro Val Arg Gly Val Lys Leu Val Gly Arg Asp Pro Lys
            105                 110                 115 aac aac ctg gaa gcc ttg gag gac ttt gag aaa gcc gca gga gcc cgc     483
Asn Asn Leu Glu Ala Leu Glu Asp Phe Glu Lys Ala Ala Gly Ala Arg
        120                 125                 130 gga ctc agc acg gag agc atc ctc atc ccc agg cag agc gaa acc tgc     531
Gly Leu Ser Thr Glu Ser Ile Leu Ile Pro Arg Gln Ser Glu Thr Cys
    135                 140                 145 tct cca ggg tag gct ggc ggc ggc tct ggt ggt ggt tct ggc ggc ggc     579
Ser Pro Gly Gln Ala Gly Gly Gly Ser Gly Gly Gly Ser Gly Gly Gly
150                 155                 160                 165 tct gag ggt ggt ggc tct gag ggt ggc ggt tct gag ggt ggc ggc tct     627
Ser Glu Gly Gly Gly Ser Glu Gly Gly Gly Ser Glu Gly Gly Gly Ser
                170                 175                 180 gag gga ggc ggt tcc ggt ggt ggc tct ggt tcc ggt gat ttt gat tat     675
Glu Gly Gly Gly Ser Gly Gly Gly Ser Gly Ser Gly Asp Phe Asp Tyr
            185                 190                 195 gaa aag atg gca aac gct aat aag ggg gct atg acc gaa aat gcc gat     723
Glu Lys Met Ala Asn Ala Asn Lys Gly Ala Met Thr Glu Asn Ala Asp
        200                 205                 210 gaa aac gcg cta cag tct gac gct aaa ggc aaa ctt gat tct gtc gct     771
Glu Asn Ala Leu Gln Ser Asp Ala Lys Gly Lys Leu Asp Ser Val Ala
    215                 220                 225 act gat tac ggt gct gct atc gat ggt ttc att ggt gac gtt tcc ggc     819
Thr Asp Tyr Gly Ala Ala Ile Asp Gly Phe Ile Gly Asp Val Ser Gly
230                 235                 240                 245 ctt gct aat ggt aat ggt gct act ggt gat ttt gct ggc tct aat tcc     867
Leu Ala Asn Gly Asn Gly Ala Thr Gly Asp Phe Ala Gly Ser Asn Ser
                250                 255                 260 caa atg gct caa gtc ggt gac ggt gat aat tca cct tta atg aat aat     915
Gln Met Ala Gln Val Gly Asp Gly Asp Asn Ser Pro Leu Met Asn Asn
            265                 270                 275 ttc cgt caa tat tta cct tcc ctc cct caa tcg gtt gaa tgt cgc cct     963
Phe Arg Gln Tyr Leu Pro Ser Leu Pro Gln Ser Val Glu Cys Arg Pro
        280                 285                 290 ttt gtc ttt ggc gct ggt aaa cca tat gaa ttt tct att gat tgt gac    1011
Phe Val Phe Gly Ala Gly Lys Pro Tyr Glu Phe Ser Ile Asp Cys Asp
```

-continued

```
Phe Val Phe Gly Ala Gly Lys Pro Tyr Glu Phe Ser Ile Asp Cys Asp
    295                 300                 305 aaa ata aac tta ttc cgt ggt gtc ttt gcg ttt ctt tta tat gtt gcc    1059
Lys Ile Asn Leu Phe Arg Gly Val Phe Ala Phe Leu Leu Tyr Val Ala
310                 315                 320                 325 acc ttt atg tat gta ttt tct acg ttt gct aac ata ctg cgt aat aag    1107
Thr Phe Met Tyr Val Phe Ser Thr Phe Ala Asn Ile Leu Arg Asn Lys
                330                 335                 340 gag tct taataagctt                                                  1123
Glu Ser <210> SEQ ID NO 2
<211> LENGTH: 535
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(525)
<220> FEATURE:
<221> NAME/KEY: sig_peptide
<222> LOCATION: (22)..(84)
<220> FEATURE:
<221> NAME/KEY: mat_peptide
<222> LOCATION: (85)..(525)

<400> SEQUENCE: 2
tctagataac gagggcaaaa a atg aaa aag aca gct atc gcg att gca gtg    51
                        Met Lys Lys Thr Ala Ile Ala Ile Ala Val
                            -20                 -15 gct ctg gct ggc ttc gct acc gta gcc cag gcc gat gga atg acg gtg    99
Ala Leu Ala Gly Phe Ala Thr Val Ala Gln Ala Asp Gly Met Thr Val
    -10                 -5                  -1   1               5 gac agg gag ttc cct gag atg aat ctg gaa tcg gtg aca ccc atg acc    147
Asp Arg Glu Phe Pro Glu Met Asn Leu Glu Ser Val Thr Pro Met Thr
                10                  15                  20 ctc acg acc ctg gaa ggg ggc aac ctg gaa gcc aag gtc acc atg ctg    195
Leu Thr Thr Leu Glu Gly Gly Asn Leu Glu Ala Lys Val Thr Met Leu
            25                  30                  35 ata agt ggc cgg tgc cag gag gtg aag gcc gtc ctg gag aaa act gac    243
Ile Ser Gly Arg Cys Gln Glu Val Lys Ala Val Leu Glu Lys Thr Asp
        40                  45                  50 gag ccg gga aaa tac acg gcc gac ggg ggc aag cac gtg gca tac atc    291
Glu Pro Gly Lys Tyr Thr Ala Asp Gly Gly Lys His Val Ala Tyr Ile
    55                  60                  65 atc agg tcg cac gtg aag gac cac tac atc ttt tac tct gag ggc cag    339
Ile Arg Ser His Val Lys Asp His Tyr Ile Phe Tyr Ser Glu Gly Gln
70                  75                  80                  85 ctc cat ggg aag ccg gtc cga ggg gtg aag ctc gtg ggc aga gac ccc    387
Leu His Gly Lys Pro Val Arg Gly Val Lys Leu Val Gly Arg Asp Pro
                90                  95                  100 aag aac aac ctg gaa gcc ttg gag gac ttt gag aaa gcc gca gga gcc    435
Lys Asn Asn Leu Glu Ala Leu Glu Asp Phe Glu Lys Ala Ala Gly Ala
            105                 110                 115 cgc gga ctc agc acg gag agc atc ctc atc ccc agg cag agc gaa acc    483
Arg Gly Leu Ser Thr Glu Ser Ile Leu Ile Pro Arg Gln Ser Glu Thr
        120                 125                 130 tgc tct cca ggg agc gct tgg tct cac ccg cag ttc gaa aaa            525
Cys Ser Pro Gly Ser Ala Trp Ser His Pro Gln Phe Glu Lys
    135                 140                 145 taataagctt                                                          535
```

<210> SEQ ID NO 3
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(22)
<223> OTHER INFORMATION: a, c, g, t, unknown or other
<220> FEATURE:
<221> NAME/KEY: modified_base
<222> LOCATION: (24)..(25)
<223> OTHER INFORMATION: a, c, g, t, unknown or other
<220> FEATURE:
<221> NAME/KEY: modified_base
<222> LOCATION: (27)..(28)
<223> OTHER INFORMATION: a, c, g, t, unknown or other
<220> FEATURE:
<221> NAME/KEY: modified_base
<222> LOCATION: (30)..(31)
<223> OTHER INFORMATION: a, c, g, t, unknown or other
<220> FEATURE:
<221> NAME/KEY: modified_base
<222> LOCATION: (33)..(34)
<223> OTHER INFORMATION: a, c, g, t, unknown or other
<220> FEATURE:
<221> NAME/KEY: modified_base
<222> LOCATION: (36)..(37)
<223> OTHER INFORMATION: a, c, g, t, unknown or other

<400> SEQUENCE: 3
gtagcccagg ccgatggagg nnknnknnkn nknnknnkgt cagggacgtg gtatc        55

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, t, unknown or other
<220> FEATURE:
<221> NAME/KEY: modified_base
<222> LOCATION: (26)..(27)
<223> OTHER INFORMATION: a, c, g, t, unknown or other
<220> FEATURE:
<221> NAME/KEY: modified_base
<222> LOCATION: (32)..(33)
<223> OTHER INFORMATION: a, c, g, t, unknown or other

<400> SEQUENCE: 4
gaccttggct tccaggttmn ncccmnncag mnncgtgagg gtcatgggtg              50

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g, t, unknown or other
<220> FEATURE:
<221> NAME/KEY: modified_base
<222> LOCATION: (26)..(27)
<223> OTHER INFORMATION: a, c, g, t, unknown or other

```
<220> FEATURE:
<221> NAME/KEY: modified_base
<222> LOCATION: (32)..(33)
<223> OTHER INFORMATION: a, c, g, t, unknown or other
<220> FEATURE:
<221> NAME/KEY: modified_base
<222> LOCATION: (35)..(36)
<223> OTHER INFORMATION: a, c, g, t, unknown or other

<400> SEQUENCE: 5
ggtgaaggcc gtcctggagn nkactnnkga gnnknnkaaa tacacggccg acgg        54

<210> SEQ ID NO 6
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, g, t, unknown or other
<220> FEATURE:
<221> NAME/KEY: modified_base
<222> LOCATION: (32)..(33)
<223> OTHER INFORMATION: a, c, g, t, unknown or other
<220> FEATURE:
<221> NAME/KEY: modified_base
<222> LOCATION: (38)..(39)
<223> OTHER INFORMATION: a, c, g, t, unknown or other
<220> FEATURE:
<221> NAME/KEY: modified_base
<222> LOCATION: (44)..(45)
<223> OTHER INFORMATION: a, c, g, t, unknown or other

<400> SEQUENCE: 6
ctggccctca gagtaaaaga tmnngtggtc mnncacmnnc gamnngatga tgtatgccac   60
gtgc                                                                64

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtttcgctac cgtagcccag gccggtgg                                      28

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaccggcttc ccatggagct ggccctcaga gtaaaag                            37

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 9
ccaggacggc cttcacctcc tggcaccggc cactgatcag catcgtgacc ttggcttcca      60
ggt                                                                    63

<210> SEQ ID NO 10
<211> LENGTH: 1267
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(1257)
<220> FEATURE:
<221> NAME/KEY: misc_feature
<222> LOCATION: (541)..(543)
<223> OTHER INFORMATION: amber stop codon

<400> SEQUENCE: 10
```

| | | | | | | | | | | | |
|---|---|---|---|---|---|---|---|---|---|---|---|
| tctagataac gagggcaaaa a | atg | aaa | aag | aca | gct | atc | gcg | att | gca | gtg | 51 |
| | Met | Lys | Lys | Thr | Ala | Ile | Ala | Ile | Ala | Val | |
| | 1 | | | 5 | | | | | | 10 | |
| gct | ctg | gct | ggc | ttc | gct | acc | gta | gcc | cag | gcc | gat | gga | gga | gag | gag | 99 |
| Ala | Leu | Ala | Gly | Phe | Ala | Thr | Val | Ala | Gln | Ala | Asp | Gly | Gly | Glu | Glu | |
| | | | 15 | | | | | 20 | | | | | 25 | | | |
| att | cag | gat | gtg | tca | ggg | acg | tgg | tat | ctg | aag | gcg | atg | acg | gtg | gac | 147 |
| Ile | Gln | Asp | Val | Ser | Gly | Thr | Trp | Tyr | Leu | Lys | Ala | Met | Thr | Val | Asp | |
| | | | 30 | | | | | 35 | | | | | 40 | | | |
| agg | gag | ttc | cct | gag | atg | aat | ctg | gaa | tcg | gtg | aca | ccc | atg | acc | ctc | 195 |
| Arg | Glu | Phe | Pro | Glu | Met | Asn | Leu | Glu | Ser | Val | Thr | Pro | Met | Thr | Leu | |
| | | 45 | | | | | 50 | | | | | 55 | | | | |
| acg | acc | ctg | gaa | ggg | ggc | aac | ctg | gaa | gcc | aag | gtc | acc | atg | ctg | ata | 243 |
| Thr | Thr | Leu | Glu | Gly | Gly | Asn | Leu | Glu | Ala | Lys | Val | Thr | Met | Leu | Ile | |
| | 60 | | | | | 65 | | | | | 70 | | | | | |
| agt | ggc | cgg | tgc | cag | gag | gtg | aag | gcc | gtc | ctg | gag | aaa | act | gac | gag | 291 |
| Ser | Gly | Arg | Cys | Gln | Glu | Val | Lys | Ala | Val | Leu | Glu | Lys | Thr | Asp | Glu | |
| 75 | | | | | 80 | | | | | 85 | | | | | 90 | |
| ccg | gga | aaa | tac | acg | gcc | gac | ggg | ggc | aag | cac | gtg | gca | tac | atc | atc | 339 |
| Pro | Gly | Lys | Tyr | Thr | Ala | Asp | Gly | Gly | Lys | His | Val | Ala | Tyr | Ile | Ile | |
| | | | 95 | | | | | 100 | | | | | 105 | | | |
| agg | tcg | cac | gtg | aag | gac | cac | tac | atc | ttt | tac | tct | gag | ggc | cag | ctc | 387 |
| Arg | Ser | His | Val | Lys | Asp | His | Tyr | Ile | Phe | Tyr | Ser | Glu | Gly | Gln | Leu | |
| | | | 110 | | | | | 115 | | | | | 120 | | | |
| cat | ggg | aag | ccg | gtc | cga | ggg | gtg | aag | ctc | gtg | ggc | aga | gac | ccc | aag | 435 |
| His | Gly | Lys | Pro | Val | Arg | Gly | Val | Lys | Leu | Val | Gly | Arg | Asp | Pro | Lys | |
| | | 125 | | | | | 130 | | | | | 135 | | | | |
| aac | aac | ctg | gaa | gcc | ttg | gag | gac | ttt | gag | aaa | gcc | gca | gga | gcc | cgc | 483 |
| Asn | Asn | Leu | Glu | Ala | Leu | Glu | Asp | Phe | Glu | Lys | Ala | Ala | Gly | Ala | Arg | |
| | 140 | | | | | 145 | | | | | 150 | | | | | |
| gga | ctc | agc | acg | gag | agc | atc | ctc | atc | ccc | agg | cag | agc | gaa | acc | tgc | 531 |
| Gly | Leu | Ser | Thr | Glu | Ser | Ile | Leu | Ile | Pro | Arg | Gln | Ser | Glu | Thr | Cys | |
| 155 | | | | | 160 | | | | | 165 | | | | | 170 | |
| tct | cca | ggg | tag | gct | ggc | ggc | ggc | tct | ggt | ggt | ggt | tct | ggc | ggc | ggc | 579 |
| Ser | Pro | Gly | Gln | Ala | Gly | Gly | Gly | Ser | Gly | Gly | Gly | Ser | Gly | Gly | Gly | |
| | | | 175 | | | | | 180 | | | | | 185 | | | |
| tct | gag | ggt | ggt | ggc | tct | gag | ggt | ggc | ggt | tct | gag | ggt | ggc | ggc | tct | 627 |
| Ser | Glu | Gly | Gly | Gly | Ser | Glu | Gly | Gly | Gly | Ser | Glu | Gly | Gly | Gly | Ser | |
| | | | 190 | | | | | 195 | | | | | 200 | | | |
| gag | gga | ggc | ggt | tcc | ggt | ggt | ggc | tct | ggt | tcc | ggt | gat | ttt | gat | tat | 675 |
| Glu | Gly | Gly | Gly | Ser | Gly | Gly | Gly | Ser | Gly | Ser | Gly | Asp | Phe | Asp | Tyr | |
| | | 205 | | | | | 210 | | | | | 215 | | | | |

```
gaa aag atg gca aac gct aat aag ggg gct atg acc gaa aat gcc gtg      723
Glu Lys Met Ala Asn Ala Asn Lys Gly Ala Met Thr Glu Asn Ala Val
    220                 225                 230 aca cct caa cct gaa gaa cag aaa gaa agg aaa acc aca gaa atg caa      771
Thr Pro Gln Pro Glu Glu Gln Lys Glu Arg Lys Thr Thr Glu Met Gln
235                 240                 245                 250 agt cca atg cag cca gtg gac caa gcg agc ctt cca ggt cac tgc agg      819
Ser Pro Met Gln Pro Val Asp Gln Ala Ser Leu Pro Gly His Cys Arg
                255                 260                 265 gaa cct cca cca tgg gaa aat gaa gcc aca gag aga att tat cat ttc      867
Glu Pro Pro Pro Trp Glu Asn Glu Ala Thr Glu Arg Ile Tyr His Phe
            270                 275                 280 gtg gtg ggg cag atg gtt tat tat cag tgc gtc cag gga tac agg gct      915
Val Val Gly Gln Met Val Tyr Tyr Gln Cys Val Gln Gly Tyr Arg Ala
        285                 290                 295 cta cac aga ggt cct gct gag agc gtc tgc aaa atg acc cac ggg aag      963
Leu His Arg Gly Pro Ala Glu Ser Val Cys Lys Met Thr His Gly Lys
    300                 305                 310 aca agg tgg acc cag ccc cag ctc ata tgc aca ggt gaa atg gag acc     1011
Thr Arg Trp Thr Gln Pro Gln Leu Ile Cys Thr Gly Glu Met Glu Thr
315                 320                 325                 330 agt cag ttt cca ggt gaa gag aag cct cag gca agc ccc gaa ggc cgt     1059
Ser Gln Phe Pro Gly Glu Glu Lys Pro Gln Ala Ser Pro Glu Gly Arg
                335                 340                 345 cct gag agt gag act tcc tgc ctc gtc aca aca aca gat ttt caa ata     1107
Pro Glu Ser Glu Thr Ser Cys Leu Val Thr Thr Thr Asp Phe Gln Ile
            350                 355                 360 cag aca gaa atg gct gca acc atg gag acg tcc ata ttt aca aca gag     1155
Gln Thr Glu Met Ala Ala Thr Met Glu Thr Ser Ile Phe Thr Thr Glu
        365                 370                 375 tac cag gta gca gtg gcc ggc tgt gtt ttc ctg ctg atc agc gtc ctc     1203
Tyr Gln Val Ala Val Ala Gly Cys Val Phe Leu Leu Ile Ser Val Leu
    380                 385                 390 ctc ctg agt ggg ctc acc tgg cag cgg aga cag agg aag agt aga aga     1251
Leu Leu Ser Gly Leu Thr Trp Gln Arg Arg Gln Arg Lys Ser Arg Arg
395                 400                 405                 410 aca atc tagaaaacca                                                   1267
Thr Ile <210> SEQ ID NO 11
<211> LENGTH: 820
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (28)..(810)

<400> SEQUENCE: 11
aagataccat ttcaacttta acacagc atg atc gaa aca tac aac caa act tct        54
                            Met Ile Glu Thr Tyr Asn Gln Thr Ser
                              1               5 ccc cga tct gcg gcc act gga ctg ccc atc agc atg aaa att ttt atg      102
Pro Arg Ser Ala Ala Thr Gly Leu Pro Ile Ser Met Lys Ile Phe Met
 10                  15                  20                  25 tat tta ctt act gtt ttt ctt atc acc cag atg att ggg tca gca ctt      150
Tyr Leu Leu Thr Val Phe Leu Ile Thr Gln Met Ile Gly Ser Ala Leu
                 30                  35                  40 ttt gct gtg tat ctt cat aga agg ttg gac aag ata gaa gat gaa agg      198
```

| | | | | | | | | | | | | | | | |
|---|---|---|---|---|---|---|---|---|---|---|---|---|---|---|---|
|Phe|Ala|Val|Tyr|Leu|His|Arg|Arg|Leu|Asp|Lys|Ile|Glu|Asp|Glu|Arg|
| | | |45| | | |50| | | |55| | | | |

```
aat ctt cat gaa gat ttt gta ttc atg aaa acg ata cag aga tgc aac    246
Asn Leu His Glu Asp Phe Val Phe Met Lys Thr Ile Gln Arg Cys Asn
         60                  65                  70 aca gga gaa aga tcc tta tcc tta ctg aac tgt gag gag att aaa agc    294
Thr Gly Glu Arg Ser Leu Ser Leu Leu Asn Cys Glu Glu Ile Lys Ser
     75                  80                  85 cag ttt gaa ggc ttt gtg aag gat ata atg tta aac aaa gag gag acg    342
Gln Phe Glu Gly Phe Val Lys Asp Ile Met Leu Asn Lys Glu Glu Thr
 90                  95                 100                 105 aag aaa gaa aac agc ttt gaa atg caa aaa ggt gat cag aat cct caa    390
Lys Lys Glu Asn Ser Phe Glu Met Gln Lys Gly Asp Gln Asn Pro Gln
                110                 115                 120 att gcg gca cat gtc ata agt gag gcc agc agt aaa aca aca tct gtg    438
Ile Ala Ala His Val Ile Ser Glu Ala Ser Ser Lys Thr Thr Ser Val
                125                 130                 135 tta cag tgg gct gaa aaa gga tac tac acc atg agc aac aac ttg gta    486
Leu Gln Trp Ala Glu Lys Gly Tyr Tyr Thr Met Ser Asn Asn Leu Val
            140                 145                 150 acc ctg gaa aat ggg aaa cag ctg acc gtt aaa aga caa gga ctc tat    534
Thr Leu Glu Asn Gly Lys Gln Leu Thr Val Lys Arg Gln Gly Leu Tyr
        155                 160                 165 tat atc tat gcc caa gtc acc ttc tgt tcc aat cgg gaa gct tcg agt    582
Tyr Ile Tyr Ala Gln Val Thr Phe Cys Ser Asn Arg Glu Ala Ser Ser
170                 175                 180                 185 caa gct cca ttt ata gcc agc ctc tgc cta aag tcc ccc ggt aga ttc    630
Gln Ala Pro Phe Ile Ala Ser Leu Cys Leu Lys Ser Pro Gly Arg Phe
                190                 195                 200 gag aga atc tta ctc aga gct gca aat acc cac agt tcc gcc aaa cct    678
Glu Arg Ile Leu Leu Arg Ala Ala Asn Thr His Ser Ser Ala Lys Pro
                205                 210                 215 tgc ggg caa caa tcc att cac ttg gga gga gta ttt gaa ttg caa cca    726
Cys Gly Gln Gln Ser Ile His Leu Gly Gly Val Phe Glu Leu Gln Pro
                220                 225                 230 ggt gct tcg gtg ttt gtc aat gtg act gat cca agc caa gtg agc cat    774
Gly Ala Ser Val Phe Val Asn Val Thr Asp Pro Ser Gln Val Ser His
            235                 240                 245 ggc act ggc ttc acg tcc ttt ggc tta ctc aaa ctc tgaacagtgt        820
Gly Thr Gly Phe Thr Ser Phe Gly Leu Leu Lys Leu
250                 255                 260
```

```
<210> SEQ ID NO 12
<211> LENGTH: 613
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(603)

<400> SEQUENCE: 12
```

```
tctagataac gggggcaaaa a atg aaa aag aca gct atc gcg att gca gtg     51
                       Met Lys Lys Thr Ala Ile Ala Ile Ala Val
                        1               5                  10 gct ctg gct ggc ttc gct acc gta gcc cag gcc gat gga ggc ggc ata     99
Ala Leu Ala Gly Phe Ala Thr Val Ala Gln Ala Asp Gly Gly Gly Ile
             15                  20                  25 cga aga agc atg tca ggg acg tgg tat ctg aag gcg atg acg gtg gac    147
Arg Arg Ser Met Ser Gly Thr Trp Tyr Leu Lys Ala Met Thr Val Asp
```

```
              30                  35                  40
agg gag ttc cct gag atg aat ctg gaa tcg gtg aca ccc atg acc ctc      195
Arg Glu Phe Pro Glu Met Asn Leu Glu Ser Val Thr Pro Met Thr Leu
            45                  50                  55 acg ctt ctg aag ggg cat aac ctg gaa gcc aag gtc acg atg ctg atc      243
Thr Leu Leu Lys Gly His Asn Leu Glu Ala Lys Val Thr Met Leu Ile
60                  65                  70 agt ggc cgg tgc cag gag gtg aag gcc gtc ctg ggg cgg act aag gag      291
Ser Gly Arg Cys Gln Glu Val Lys Ala Val Leu Gly Arg Thr Lys Glu
 75                  80                  85                  90 agg aag aaa tac acg gcc gac ggg ggc aag cac gtg gca tac atc atc      339
Arg Lys Lys Tyr Thr Ala Asp Gly Gly Lys His Val Ala Tyr Ile Ile
                95                 100                 105 cct tcg gct gtg cgt gac cac gtg atc ttt tac tct gag ggc cag ctc      387
Pro Ser Ala Val Arg Asp His Val Ile Phe Tyr Ser Glu Gly Gln Leu
            110                 115                 120 cat ggg aag ccg gtc cga ggg gtg aag ctc gtg ggc aga gac ccc aag      435
His Gly Lys Pro Val Arg Gly Val Lys Leu Val Gly Arg Asp Pro Lys
        125                 130                 135 aac aac ctg gaa gcc ttg gag gac ttt gag aaa gcc gca gga gcc cgc      483
Asn Asn Leu Glu Ala Leu Glu Asp Phe Glu Lys Ala Ala Gly Ala Arg
    140                 145                 150 gga ctc agc acg gag agc atc ctc atc ccc agg cag agc gaa acc tgc      531
Gly Leu Ser Thr Glu Ser Ile Leu Ile Pro Arg Gln Ser Glu Thr Cys
155                 160                 165                 170 tct cca ggg gat gca tcg atg acc ggt ggt cag cag atg ggt agc gct      579
Ser Pro Gly Asp Ala Ser Met Thr Gly Gly Gln Gln Met Gly Ser Ala
                175                 180                 185 tgg tct cac ccg cag ttc gaa aaa taataagctt                           613
Trp Ser His Pro Gln Phe Glu Lys
            190

<210> SEQ ID NO 13
<211> LENGTH: 613
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(603)

<400> SEQUENCE: 13
tctagataac gggggcaaaa a atg aaa aag aca gct atc gcg att gca gtg       51
                        Met Lys Lys Thr Ala Ile Ala Ile Ala Val
                         1               5                  10 gct ctg gct ggc ttc gct acc gta gcc cag gcc gat ggg gga aga tgg       99
Ala Leu Ala Gly Phe Ala Thr Val Ala Gln Ala Asp Gly Gly Arg Trp
                15                  20                  25 cgt gtg tgt tgg tca ggg acg tgg tat ctg aag gcg atg acg gtg gac      147
Arg Val Cys Trp Ser Gly Thr Trp Tyr Leu Lys Ala Met Thr Val Asp
            30                  35                  40 agg gag ttc ccc gag atg aat ctg gaa tcg gtg aca ccc atg acc ctc      195
Arg Glu Phe Pro Glu Met Asn Leu Glu Ser Val Thr Pro Met Thr Leu
        45                  50                  55 acg cag ctg gat ggg aag aac ctg gaa gcc aag gtc acg atg ctg atc      243
Thr Gln Leu Asp Gly Lys Asn Leu Glu Ala Lys Val Thr Met Leu Ile
    60                  65                  70 agt ggc cgg tgc cag gag gtg aag gcc gtc ctg gag ttg act aat gag      291
Ser Gly Arg Cys Gln Glu Val Lys Ala Val Leu Glu Leu Thr Asn Glu
 75                  80                  85                  90
```

```
ggg gtg aaa tac acg gcc gac ggg ggc aag cac gtg gca tac atc atc      339
Gly Val Lys Tyr Thr Ala Asp Gly Gly Lys His Val Ala Tyr Ile Ile
             95                 100                 105 ccg tcg cgg gtg tct gac cac ttt atc ttt tac tct gag ggc cag ctc      387
Pro Ser Arg Val Ser Asp His Phe Ile Phe Tyr Ser Glu Gly Gln Leu
            110                 115                 120 cat ggg aag ccg gtc cga ggg gtg aag ctc gtg ggc aga gac ccc aag      435
His Gly Lys Pro Val Arg Gly Val Lys Leu Val Gly Arg Asp Pro Lys
            125                 130                 135 aac aac ctg gaa gcc ttg gag gac ttt gag aaa gcc gca gga gcc cgc      483
Asn Asn Leu Glu Ala Leu Glu Asp Phe Glu Lys Ala Ala Gly Ala Arg
140                 145                 150 gga ctc agc acg gag agc atc ctc atc ccc agg cag agc gaa acc tgc      531
Gly Leu Ser Thr Glu Ser Ile Leu Ile Pro Arg Gln Ser Glu Thr Cys
155                 160                 165                 170 tct cca ggg gat gca tcg atg acc ggt ggt cag cag atg ggt agc gct      579
Ser Pro Gly Asp Ala Ser Met Thr Gly Gly Gln Gln Met Gly Ser Ala
                175                 180                 185 tgg tct cac ccg cag ttc gaa aaa taataagctt                           613
Trp Ser His Pro Gln Phe Glu Lys
                190

<210> SEQ ID NO 14
<211> LENGTH: 613
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(603)

<400> SEQUENCE: 14
tctagataac gggggcaaaa a atg aaa aag aca gct atc gcg att gca gtg       51
                        Met Lys Lys Thr Ala Ile Ala Ile Ala Val
                          1               5                  10 gct ctg gct ggc ttc gct acc gta gcg cag gcc gac gca tcg atg acc       99
Ala Leu Ala Gly Phe Ala Thr Val Ala Gln Ala Asp Ala Ser Met Thr
                 15                  20                  25 ggt ggt cag cag atg ggt gcc tca gac gag gag att cag gat gtg cca      147
Gly Gly Gln Gln Met Gly Ala Ser Asp Glu Glu Ile Gln Asp Val Pro
             30                  35                  40 ggg acg tgg tat ctg aag gcg atg acg gtg ggt tct ggg tcg att tgt      195
Gly Thr Trp Tyr Leu Lys Ala Met Thr Val Gly Ser Gly Ser Ile Cys
         45                  50                  55 acg tgt agt gaa tcg gtg aca ccc atg acc ctc acg acc ctg gaa ggg      243
Thr Cys Ser Glu Ser Val Thr Pro Met Thr Leu Thr Thr Leu Glu Gly
 60                  65                  70 ggc aac ctg gaa gcc aag gtc acc atg gtt gtt cgt ggc cgg tgc cag      291
Gly Asn Leu Glu Ala Lys Val Thr Met Val Val Arg Gly Arg Cys Gln
75                  80                  85                  90 gag gtg aag gca gta ctg gag aaa act gac gag ccg ggt aaa tac acg      339
Glu Val Lys Ala Val Leu Glu Lys Thr Asp Glu Pro Gly Lys Tyr Thr
                 95                 100                 105 gcc gac gga ggc aat cac gtg gca tac atc atc agg tcg cac gtg aag      387
Ala Asp Gly Gly Asn His Val Ala Tyr Ile Ile Arg Ser His Val Lys
            110                 115                 120 gac cac tac atc ttt tac tct gag ggc gag gtg atg ggg ttg cct gtc      435
Asp His Tyr Ile Phe Tyr Ser Glu Gly Glu Val Met Gly Leu Pro Val
            125                 130                 135
```

```
cga ggg gtc cag ctc gtt ggc aga gac ccc aag aac aac ctg gaa gcc      483
Arg Gly Val Gln Leu Val Gly Arg Asp Pro Lys Asn Asn Leu Glu Ala
    140                 145                 150 ttg gag gac ttt gag aaa gcc gca gga gcc cgc gga ctc agc acg gag      531
Leu Glu Asp Phe Glu Lys Ala Ala Gly Ala Arg Gly Leu Ser Thr Glu
155                 160                 165                 170 agc atc ctc atc ccc agg cag agc gaa acc tgc tct cca ggg agc gct      579
Ser Ile Leu Ile Pro Arg Gln Ser Glu Thr Cys Ser Pro Gly Ser Ala
                175                 180                 185 tgg tct cac ccg cag ttc gaa aaa taataagctt                           613
Trp Ser His Pro Gln Phe Glu Lys
            190

<210> SEQ ID NO 15
<211> LENGTH: 613
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(603)

<400> SEQUENCE: 15
tctagataac gggggcaaaa a atg aaa aag aca gct atc gcg att gca gtg      51
                        Met Lys Lys Thr Ala Ile Ala Ile Ala Val
                          1               5                  10 gct ctg gct ggc ttc gct acc gta gcg cag gcc gac gca tcg atg acc      99
Ala Leu Ala Gly Phe Ala Thr Val Ala Gln Ala Asp Ala Ser Met Thr
             15                  20                  25 ggt ggt cag cag atg ggt gcc tca gac gag gag att cag gat gtg cca      147
Gly Gly Gln Gln Met Gly Ala Ser Asp Glu Glu Ile Gln Asp Val Pro
         30                  35                  40 ggg acg tgg tat ctg aag gcg atg acg gtg gtt cat ggt gtt cat gat      195
Gly Thr Trp Tyr Leu Lys Ala Met Thr Val Val His Gly Val His Asp
     45                  50                  55 ctt ttt ttg gaa tcg gtg aca ccc atg acc ctc acg acc ctg gaa ggg      243
Leu Phe Leu Glu Ser Val Thr Pro Met Thr Leu Thr Thr Leu Glu Gly
 60                  65                  70 ggc aac ctg gaa gcc aag gtc acc atg ttt ggt aat ggc cgg tgc cag      291
Gly Asn Leu Glu Ala Lys Val Thr Met Phe Gly Asn Gly Arg Cys Gln
75                  80                  85                  90 gag gtg aac gca gta ctg gaa aaa act gac gag ccg ggt aaa tac acg      339
Glu Val Asn Ala Val Leu Glu Lys Thr Asp Glu Pro Gly Lys Tyr Thr
                 95                 100                 105 gcc gac gga ggc aat cac gtg gca tac atc atc agg tcg cac gtg aag      387
Ala Asp Gly Gly Asn His Val Ala Tyr Ile Ile Arg Ser His Val Lys
             110                 115                 120 gac cac tac atc ttt tac tct gag ggc gag cat atg ggg tgg act gtc      435
Asp His Tyr Ile Phe Tyr Ser Glu Gly Glu His Met Gly Trp Thr Val
         125                 130                 135 cga ggg gtc cag ctc gtt ggc aga gac ccc aag aac aac ctg gaa gcc      483
Arg Gly Val Gln Leu Val Gly Arg Asp Pro Lys Asn Asn Leu Glu Ala
     140                 145                 150 ttg gag gac ttt gag aaa gcc gca gga gcc cgc gga ctc agc acg gag      531
Leu Glu Asp Phe Glu Lys Ala Ala Gly Ala Arg Gly Leu Ser Thr Glu
155                 160                 165                 170 agc atc ctc atc ccc agg cag agc gaa acc tgc tct cca ggg agc gct      579
Ser Ile Leu Ile Pro Arg Gln Ser Glu Thr Cys Ser Pro Gly Ser Ala
                175                 180                 185 tgg tct cac ccg cag ttc gaa aaa taataagctt                           613
Trp Ser His Pro Gln Phe Glu Lys
            190
```

Trp Ser His Pro Gln Phe Glu Lys
            190

<210> SEQ ID NO 16
<211> LENGTH: 619
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(609)

<400> SEQUENCE: 16
tctagataac gggggcaaaa a atg aaa aag aca gct atc gcg att gca gtg         51
                        Met Lys Lys Thr Ala Ile Ala Ile Ala Val
                         1               5                   10 gct ctg gct ggc ttc gct acc gta gcg cag gcc gac gca tcg atg acc         99
Ala Leu Ala Gly Phe Ala Thr Val Ala Gln Ala Asp Ala Ser Met Thr
             15                  20                  25 ggt ggt cag cag atg ggt gcc tca gac gag gag att cag gat gtg cca        147
Gly Gly Gln Gln Met Gly Ala Ser Asp Glu Glu Ile Gln Asp Val Pro
         30                  35                  40 ggg acg tgg tat ctg aag gcg atg acg gtg cct gat ttg tct ctg acg        195
Gly Thr Trp Tyr Leu Lys Ala Met Thr Val Pro Asp Leu Ser Leu Thr
     45                  50                  55 ctt cag gct act gcg gaa tcg gtg aca ccc atg acc ctc acg acc ctg        243
Leu Gln Ala Thr Ala Glu Ser Val Thr Pro Met Thr Leu Thr Thr Leu
 60                  65                  70 gaa ggg ggc aac ctg gaa gcc aag gtc acc atg ttt ggt tat ggc cgg        291
Glu Gly Gly Asn Leu Glu Ala Lys Val Thr Met Phe Gly Tyr Gly Arg
 75                  80                  85                  90 tgc cag gag gtg aag gca gta ctg gag aaa act gac gag ccg ggt aaa        339
Cys Gln Glu Val Lys Ala Val Leu Glu Lys Thr Asp Glu Pro Gly Lys
                 95                 100                 105 tac acg gcc gac gga ggc aat cac gtg gca tac atc atc agg tcg cac        387
Tyr Thr Ala Asp Gly Gly Asn His Val Ala Tyr Ile Ile Arg Ser His
            110                 115                 120 gtg aag gac cac tac atc ttt tac tct gag ggc gag ctg atg ggg gtg        435
Val Lys Asp His Tyr Ile Phe Tyr Ser Glu Gly Glu Leu Met Gly Val
        125                 130                 135 ctt gtc cga ggg gtc cag ctc gtt ggc aga gac ccc aag aac aac ctg        483
Leu Val Arg Gly Val Gln Leu Val Gly Arg Asp Pro Lys Asn Asn Leu
    140                 145                 150 gaa gcc ttg gag gac ttt gag aaa gcc gca gga gcc cgc gga ctc agc        531
Glu Ala Leu Glu Asp Phe Glu Lys Ala Ala Gly Ala Arg Gly Leu Ser
155                 160                 165                 170 acg gag agc atc ctc atc ccc agg cag agc gaa acc tgc tct cca ggg        579
Thr Glu Ser Ile Leu Ile Pro Arg Gln Ser Glu Thr Cys Ser Pro Gly
                175                 180                 185 agc gct tgg tct cac ccg cag ttc gaa aaa taataagctt                     619
Ser Ala Trp Ser His Pro Gln Phe Glu Lys
            190                 195

<210> SEQ ID NO 17
<211> LENGTH: 613
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS -continued

<222> LOCATION: (22)..(603)

<400> SEQUENCE: 17

| | | | | | | | | | | | | | | | |
|---|---|---|---|---|---|---|---|---|---|---|---|---|---|---|---|
| tctagataac gagggcaaaa a | atg<br>Met<br>1 | aaa<br>Lys | aag<br>Lys | aca<br>Thr | gct<br>Ala<br>5 | atc<br>Ile | gcg<br>Ala | att<br>Ile | gca<br>Ala | gtg<br>Val<br>10 | | | | | 51 |
| gct<br>Ala | ctg<br>Leu | gct<br>Ala | ggc<br>Gly | ttc<br>Phe<br>15 | gct<br>Ala | acc<br>Thr | gta<br>Val | gcc<br>Ala | cag<br>Gln<br>20 | gcc<br>Ala | gat<br>Asp | gga<br>Gly | gga<br>Gly | gtg<br>Val<br>25 | ggt<br>Gly | 99 |
| aaa<br>Lys | cgt<br>Arg | gga<br>Gly | ctg<br>Leu<br>30 | tca<br>Ser | ggg<br>Gly | acg<br>Thr | tgg<br>Trp | tat<br>Tyr<br>35 | ctg<br>Leu | aag<br>Lys | gcg<br>Ala | atg<br>Met | acg<br>Thr<br>40 | gtg<br>Val | gac<br>Asp | 147 |
| agg<br>Arg | gag<br>Glu | ttc<br>Phe<br>45 | ccc<br>Pro | gag<br>Glu | atg<br>Met | gat<br>Asp | ctg<br>Leu<br>50 | gaa<br>Glu | tcg<br>Ser | gtg<br>Val | aca<br>Thr | ccc<br>Pro<br>55 | atg<br>Met | acc<br>Thr | ctc<br>Leu | 195 |
| acg<br>Thr | gga<br>Gly<br>60 | ctg<br>Leu | gct<br>Ala | ggg<br>Gly | ggt<br>Gly | gac<br>Asp<br>65 | ctg<br>Leu | gaa<br>Glu | gcc<br>Ala | aag<br>Lys | gtc<br>Val<br>70 | aca<br>Thr | atg<br>Met | ctg<br>Leu | atc<br>Ile | 243 |
| agt<br>Ser<br>75 | ggc<br>Gly | cgg<br>Arg | tgc<br>Cys | cag<br>Gln | gag<br>Glu<br>80 | gtg<br>Val | aag<br>Lys | gcc<br>Ala | gtc<br>Val | ctg<br>Leu<br>85 | gag<br>Glu | ggg<br>Gly | act<br>Thr | aat<br>Asn | gag<br>Glu<br>90 | 291 |
| ctg<br>Leu | gat<br>Asp | aaa<br>Lys | tac<br>Tyr<br>95 | acg<br>Thr | gcc<br>Ala | gac<br>Asp | ggg<br>Gly | ggc<br>Gly<br>100 | aag<br>Lys | cac<br>His | gtg<br>Val | gca<br>Ala | tac<br>Tyr<br>105 | atc<br>Ile | atc<br>Ile | 339 |
| cat<br>His | ccg<br>Pro | cat<br>His<br>110 | gtg<br>Val | act<br>Thr | gac<br>Asp | cac<br>His | ttg<br>Leu<br>115 | atc<br>Ile | ttt<br>Phe | tac<br>Tyr | tct<br>Ser | gag<br>Glu<br>120 | ggc<br>Gly | cag<br>Gln | ctc<br>Leu | 387 |
| cat<br>His | ggg<br>Gly<br>125 | aag<br>Lys | ccg<br>Pro | gtc<br>Val | cga<br>Arg | ggg<br>Gly<br>130 | gtg<br>Val | aag<br>Lys | ctc<br>Leu | gtg<br>Val | ggc<br>Gly<br>135 | aga<br>Arg | gac<br>Asp | ccc<br>Pro | aag<br>Lys | 435 |
| aac<br>Asn | aac<br>Asn<br>140 | ctg<br>Leu | gaa<br>Glu | gcc<br>Ala | ttg<br>Leu<br>145 | gag<br>Glu | gac<br>Asp | ttt<br>Phe | gag<br>Glu | aaa<br>Lys<br>150 | gcc<br>Ala | gca<br>Ala | gga<br>Gly | gcc<br>Ala | cgc<br>Arg | 483 |
| gga<br>Gly<br>155 | ctc<br>Leu | agc<br>Ser | acg<br>Thr | gag<br>Glu | agc<br>Ser<br>160 | atc<br>Ile | ctc<br>Leu | atc<br>Ile | ccc<br>Pro | agg<br>Arg<br>165 | cag<br>Gln | agc<br>Ser | gaa<br>Glu | acc<br>Thr | tgc<br>Cys<br>170 | 531 |
| tct<br>Ser | cca<br>Pro | ggg<br>Gly | gat<br>Asp<br>175 | gca<br>Ala | tcg<br>Ser | atg<br>Met | acc<br>Thr | ggt<br>Gly<br>180 | ggt<br>Gly | cag<br>Gln | cag<br>Gln | atg<br>Met | ggt<br>Gly<br>185 | agc<br>Ser | gct<br>Ala | 579 |
| tgg<br>Trp | tct<br>Ser | cac<br>His | ccg<br>Pro<br>190 | cag<br>Gln | ttc<br>Phe | gaa<br>Glu | aaa<br>Lys | taataagctt | | | | | | | | 613 |

<210> SEQ ID NO 18
<211> LENGTH: 613
<212> TYPE: DNA
<213> ORGANISM: Artificial Sequence
<220> FEATURE:
<223> OTHER INFORMATION: Description of Artificial Sequence: Synthetic
    nucleotide sequence
<220> FEATURE:
<221> NAME/KEY: CDS
<222> LOCATION: (22)..(603)

<400> SEQUENCE: 18

| | | | | | | | | | | | | | | | |
|---|---|---|---|---|---|---|---|---|---|---|---|---|---|---|---|
| tctagataac cagggcaaaa a | atg<br>Met<br>1 | aaa<br>Lys | aag<br>Lys | aca<br>Thr | gct<br>Ala<br>5 | atc<br>Ile | gcg<br>Ala | att<br>Ile | gca<br>Ala | gtg<br>Val<br>10 | | | | | 51 |
| gct<br>Ala | ctg<br>Leu | gct<br>Ala | ggc<br>Gly | ttc<br>Phe<br>15 | gct<br>Ala | acc<br>Thr | gta<br>Val | gcc<br>Ala | cag<br>Gln<br>20 | gcc<br>Ala | gat<br>Asp | gga<br>Gly | gga<br>Gly | gtg<br>Val<br>25 | ggt<br>Gly | 99 |
| aga<br>Arg | cgt<br>Arg | gga<br>Gly | ctg<br>Leu | tca<br>Ser | ggg<br>Gly | acg<br>Thr | tgg<br>Trp | tat<br>Tyr | ctg<br>Leu | aag<br>Lys | gcg<br>Ala | atg<br>Met | acg<br>Thr | gtg<br>Val | gac<br>Asp | 147 |

```
            Arg Arg Gly Leu Ser Gly Thr Trp Tyr Leu Lys Ala Met Thr Val Asp
                        30                  35                  40 agg gag tcc ccc gag atg aac ctg gaa tcg gtg aca ccc atg acc ctc                  195
Arg Glu Ser Pro Glu Met Asn Leu Glu Ser Val Thr Pro Met Thr Leu
        45                  50                  55 acg ggg ctg gct ggg ggt gac ctg gaa gcc aag gtc acg atg ctg atc                  243
Thr Gly Leu Ala Gly Gly Asp Leu Glu Ala Lys Val Thr Met Leu Ile
60                  65                  70 agt ggc cgg tgc cag gag gta aag gcc gcc ctg gag ggg act aat gag                  291
Ser Gly Arg Cys Gln Glu Val Lys Ala Ala Leu Glu Gly Thr Asn Glu
    75                  80                  85                  90 ctg gat aaa tac acg gcc gac ggg ggc aag cac gtg gta tac atc atc                  339
Leu Asp Lys Tyr Thr Ala Asp Gly Gly Lys His Val Val Tyr Ile Ile
                95                  100                 105 cat ccg cat gtg act gac cac ttg atc ttt tac tct gag ggc cag ctc                  387
His Pro His Val Thr Asp His Leu Ile Phe Tyr Ser Glu Gly Gln Leu
            110                 115                 120 cat ggg aag ccg gtc cga ggg gtg aag ctc gtg ggc aga gac ccc aag                  435
His Gly Lys Pro Val Arg Gly Val Lys Leu Val Gly Arg Asp Pro Lys
        125                 130                 135 aac aac ctg gaa gcc ttg gag gac ttt gag aaa gcc gca gga gcc cgc                  483
Asn Asn Leu Glu Ala Leu Glu Asp Phe Glu Lys Ala Ala Gly Ala Arg
    140                 145                 150 gga ctc agc acg gag agc atc ctc atc ccc agg cag agc gaa acc tgc                  531
Gly Leu Ser Thr Glu Ser Ile Leu Ile Pro Arg Gln Ser Glu Thr Cys
155                 160                 165                 170 tct cca ggg gat gca tcg atg acc ggt ggt cag cag atg ggt agc gct                  579
Ser Pro Gly Asp Ala Ser Met Thr Gly Gly Gln Gln Met Gly Ser Ala
                175                 180                 185 tgg tct cac ccg cag ttc gaa aaa taataagctt                                       613
Trp Ser His Pro Gln Phe Glu Lys
            190

<210> SEQ ID NO 19
<211> LENGTH: 613
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(603)

<400> SEQUENCE: 19
tctagataac gagggcaaaa a atg aaa aag aca gct atc gcg att gca gtg             51
                        Met Lys Lys Thr Ala Ile Ala Ile Ala Val
                        1               5                   10 gct ctg gct ggc ttc gct acc gta gcc cag gcc gat gga gga gtg ggt                  99
Ala Leu Ala Gly Phe Ala Thr Val Ala Gln Ala Asp Gly Gly Val Gly
            15                  20                  25 aga cgt gga ctg tca ggg acg tgg tat ctg aag gcg atg acg gtg gac                  147
Arg Arg Gly Leu Ser Gly Thr Trp Tyr Leu Lys Ala Met Thr Val Asp
        30                  35                  40 agg gag tcc ccc gag atg aat ctg gaa tcg gtg aca ccc atg acc ctc                  195
Arg Glu Ser Pro Glu Met Asn Leu Glu Ser Val Thr Pro Met Thr Leu
    45                  50                  55 acg ggg ctg gct ggg ggt gac ctg gaa gcc aag gtc acg atg ctg atc                  243
Thr Gly Leu Ala Gly Gly Asp Leu Glu Ala Lys Val Thr Met Leu Ile
60                  65                  70 agt ggc cgg tgc cag gag gtg aag gcc gtc ctg gag ggg act aat gag                  291
Ser Gly Arg Cys Gln Glu Val Lys Ala Val Leu Glu Gly Thr Asn Glu
    75                  80                  85
```

```
                75                  80                  85                  90
ctg gat aaa tac acg gcc gac ggg ggc aag cac gtg gca tac atc atc       339
Leu Asp Lys Tyr Thr Ala Asp Gly Gly Lys His Val Ala Tyr Ile Ile
                 95                  100                 105 cat ccg cat gtg act gac cac ttg atc ttt tac tct gag ggc cag ctc       387
His Pro His Val Thr Asp His Leu Ile Phe Tyr Ser Glu Gly Gln Leu
         110                 115                 120 cat ggg aag ccg gtc cga ggg gtg aag ctc gtg ggc aga gac ccc aag       435
His Gly Lys Pro Val Arg Gly Val Lys Leu Val Gly Arg Asp Pro Lys
         125                 130                 135 aac aac ctg gaa gcc ttg gag gac ttt gag aaa gcc gca gga gcc cgc       483
Asn Asn Leu Glu Ala Leu Glu Asp Phe Glu Lys Ala Ala Gly Ala Arg
         140                 145                 150 gga ctc agc acg gag agc atc ctc atc ccc agg cag agc gaa acc tgc       531
Gly Leu Ser Thr Glu Ser Ile Leu Ile Pro Arg Gln Ser Glu Thr Cys
155                 160                 165                 170 tct cca ggg gat gca tcg atg acc ggt ggt cag cag atg ggt agc gct       579
Ser Pro Gly Asp Ala Ser Met Thr Gly Gly Gln Gln Met Gly Ser Ala
                 175                 180                 185 tgg tct cac ccg cag ttc gaa aaa taataagctt                            613
Trp Ser His Pro Gln Phe Glu Lys
                 190

<210> SEQ ID NO 20
<211> LENGTH: 613
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(603)

<400> SEQUENCE: 20
tctagataac gggggcaaaa a atg aaa aag aca gct atc gcg att gca gtg       51
                       Met Lys Lys Thr Ala Ile Ala Ile Ala Val
                         1               5                   10 gct ctg gct ggc ttc gct acc gta gcc cag gcc gat gga gga gtg ggt       99
Ala Leu Ala Gly Phe Ala Thr Val Ala Gln Ala Asp Gly Gly Val Gly
                15                  20                  25 aga cgt gga ctg tca ggg acg tgg tat ctg aag gcg atg acg gtg gac       147
Arg Arg Gly Leu Ser Gly Thr Trp Tyr Leu Lys Ala Met Thr Val Asp
         30                  35                  40 agg gag ttc ccc gag atg aat ctg gaa tcg gtg aca ccc atg acc ctc       195
Arg Glu Phe Pro Glu Met Asn Leu Glu Ser Val Thr Pro Met Thr Leu
     45                  50                  55 acg ggg ctg gct ggg ggt gac ctg gaa gcc aag gtc acg atg ctg atc       243
Thr Gly Leu Ala Gly Gly Asp Leu Glu Ala Lys Val Thr Met Leu Ile
 60                  65                  70 agt ggc cgg tgc cag gag gtg aag gcc gtc ctg gag ggg act aat gag       291
Ser Gly Arg Cys Gln Glu Val Lys Ala Val Leu Glu Gly Thr Asn Glu
75                  80                  85                  90 ctg gat aaa tac acg gcc gac ggg ggc aag cac gtg gca tac atc atc       339
Leu Asp Lys Tyr Thr Ala Asp Gly Gly Lys His Val Ala Tyr Ile Ile
                 95                  100                 105 cat tcg cat gtg act gac cac ttg atc ttt tac tct gag ggc cag ctc       387
His Ser His Val Thr Asp His Leu Ile Phe Tyr Ser Glu Gly Gln Leu
         110                 115                 120 cat ggg aag ccg gtc cga ggg gtg aag ctc gtg ggc aga gac ccc aag       435
His Gly Lys Pro Val Arg Gly Val Lys Leu Val Gly Arg Asp Pro Lys
         125                 130                 135
```

```
aac aac ctg gaa gcc ttg gag gac ttt gag aaa gcc gca gga gcc cgc     483
Asn Asn Leu Glu Ala Leu Glu Asp Phe Glu Lys Ala Ala Gly Ala Arg
    140                 145                 150 gga ctc agc acg gag agc atc ctc atc ccc agg cag agc gaa acc tgc     531
Gly Leu Ser Thr Glu Ser Ile Leu Ile Pro Arg Gln Ser Glu Thr Cys
155                 160                 165                 170 tct cca ggg gat gca tcg atg acc ggt ggt cag cag atg ggt agc gct     579
Ser Pro Gly Asp Ala Ser Met Thr Gly Gly Gln Gln Met Gly Ser Ala
                175                 180                 185 tgg tct cac ccg cag ttc gaa aaa taataagctt                          613
Trp Ser His Pro Gln Phe Glu Lys
            190

<210> SEQ ID NO 21
<211> LENGTH: 727
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(717)
<220> FEATURE:
<221> NAME/KEY: misc_feature
<222> LOCATION: (571)..(573)
<223> OTHER INFORMATION: amber stop codon

<400> SEQUENCE: 21
tctagataac gggggcaaaa a atg aaa aag aca gct atc gcg att gca gtg      51
                        Met Lys Lys Thr Ala Ile Ala Ile Ala Val
                          1               5                  10 gct ctg gct ggc ttc gct acc gta gcc cag gcc gat gga gga gtg ggt      99
Ala Leu Ala Gly Phe Ala Thr Val Ala Gln Ala Asp Gly Gly Val Gly
                15                  20                  25 aga cgt gga ctg tca ggg acg tgg tat ctg aag gcg atg gcg gtg gac     147
Arg Arg Gly Leu Ser Gly Thr Trp Tyr Leu Lys Ala Met Ala Val Asp
            30                  35                  40 agg gag ttc ccc gag atg aat ctg gaa tcg gtg aca ccc atg acc ctc     195
Arg Glu Phe Pro Glu Met Asn Leu Glu Ser Val Thr Pro Met Thr Leu
        45                  50                  55 acg ggg ctg gct ggg ggt gac ctg gga gtc aag gtc acg atg ctg atc     243
Thr Gly Leu Ala Gly Gly Asp Leu Gly Val Lys Val Thr Met Leu Ile
    60                  65                  70 agt ggc cgg tgc cag gag gtg aag gcc gtc ctg gag ggg act aat gag     291
Ser Gly Arg Cys Gln Glu Val Lys Ala Val Leu Glu Gly Thr Asn Glu
75                  80                  85                  90 ctg gat aaa tac acg gcc gac ggg ggc aag cac gtg gca tac atc atc     339
Leu Asp Lys Tyr Thr Ala Asp Gly Gly Lys His Val Ala Tyr Ile Ile
                95                 100                 105 cat tcg cat gtg act gac cac ttg atc ctt tac tct gag ggc cag ctc     387
His Ser His Val Thr Asp His Leu Ile Leu Tyr Ser Glu Gly Gln Leu
            110                 115                 120 cat ggg aag ccg gtc cga ggg gtg aag ctc gtg ggc aga gac ccc aag     435
His Gly Lys Pro Val Arg Gly Val Lys Leu Val Gly Arg Asp Pro Lys
        125                 130                 135 aac aac ctg gaa gcc ttg gag gac ttt gag aaa gcc gca gga gcc cgc     483
Asn Asn Leu Glu Ala Leu Glu Asp Phe Glu Lys Ala Ala Gly Ala Arg
    140                 145                 150 gga ctc agc acg gag agc atc ctc atc ccc agg cag agc gaa acc tgc     531
Gly Leu Ser Thr Glu Ser Ile Leu Ile Pro Arg Gln Ser Glu Thr Cys
155                 160                 165                 170
```

-continued

| | | |
|---|---|---|
| tct cca ggg agc gct tgg tcc cac ccg cag ttc gaa aaa tag gct agc<br>Ser Pro Gly Ser Ala Trp Ser His Pro Gln Phe Glu Lys Gln Ala Ser<br>                     175                           180                       185 | | 579 |
| ctg gct gaa gct aaa gtt ctg gct aac cgt gaa ctg gac aaa tac ggt<br>Leu Ala Glu Ala Lys Val Leu Ala Asn Arg Glu Leu Asp Lys Tyr Gly<br>            190                         195                       200 | | 627 |
| gtt tcc gac tac tac aaa aac ctc atc aac aac gct aaa acc gtt gaa<br>Val Ser Asp Tyr Tyr Lys Asn Leu Ile Asn Asn Ala Lys Thr Val Glu<br>        205                         210                       215 | | 675 |
| ggt gtt aaa gct ctg atc gac gaa att ctc gca gca ctg ccg taa<br>Gly Val Lys Ala Leu Ile Asp Glu Ile Leu Ala Ala Leu Pro<br>    220                     225                     230 | | 720 |
| taagctt | | 727 |

<210> SEQ ID NO 22
<211> LENGTH: 727
<212> TYPE: DNA
<213> ORGANISM: Artificial Sequence
<220> FEATURE:
<223> OTHER INFORMATION: Description of Artificial Sequence: Synthetic
     nucleotide sequence
<220> FEATURE:
<221> NAME/KEY: CDS
<222> LOCATION: (22)..(717)
<220> FEATURE:
<221> NAME/KEY: misc_feature
<222> LOCATION: (571)..(573)
<223> OTHER INFORMATION: amber stop codon

<400> SEQUENCE: 22

| | | |
|---|---|---|
| tctagataac gagggcaaaa a atg aaa aag aca gct atc gcg att gca gtg<br>                                    Met Lys Lys Thr Ala Ile Ala Ile Ala Val<br>                                       1                  5                       10 | | 51 |
| gct ctg gct ggc ttc gct acc gta gcc cag gcc gat gga gga gag gag<br>Ala Leu Ala Gly Phe Ala Thr Val Ala Gln Ala Asp Gly Gly Glu Glu<br>             15                         20                         25 | | 99 |
| att cag gat gtg tca ggg acg tgg tat ctg aag gcg atg acg gtg gac<br>Ile Gln Asp Val Ser Gly Thr Trp Tyr Leu Lys Ala Met Thr Val Asp<br>            30                        35                       40 | | 147 |
| agg gag ttc cct gag atg aat ctg gaa tcg gtg aca ccc atg acc ctc<br>Arg Glu Phe Pro Glu Met Asn Leu Glu Ser Val Thr Pro Met Thr Leu<br>          45                        50                       55 | | 195 |
| acg acc ctg gaa ggg ggc aac ctg gaa gcc aag gtc acc atg ctg ata<br>Thr Thr Leu Glu Gly Gly Asn Leu Glu Ala Lys Val Thr Met Leu Ile<br>60                       65                       70 | | 243 |
| agt ggc cgg tgc cag gag gtg aag gcc gtc ctg gag aaa act gac gag<br>Ser Gly Arg Cys Gln Glu Val Lys Ala Val Leu Glu Lys Thr Asp Glu<br>75                       80                       85                       90 | | 291 |
| ccg gga aaa tac acg gcc gac ggg ggc aag cac gtg gca tac atc atc<br>Pro Gly Lys Tyr Thr Ala Asp Gly Gly Lys His Val Ala Tyr Ile Ile<br>             95                       100                       105 | | 339 |
| agg tcg cac gtg aag gac cac tac atc ttt tac tct gag ggc cag ctc<br>Arg Ser His Val Lys Asp His Tyr Ile Phe Tyr Ser Glu Gly Gln Leu<br>            110                       115                       120 | | 387 |
| cat ggg aag ccg gtc cga ggg gtg aag ctc gtg ggc aga gac ccc aag<br>His Gly Lys Pro Val Arg Gly Val Lys Leu Val Gly Arg Asp Pro Lys<br>        125                       130                       135 | | 435 |
| aac aac ctg gaa gcc ttg gag gac ttt gag aaa gcc gca gga gcc cgc<br>Asn Asn Leu Glu Ala Leu Glu Asp Phe Glu Lys Ala Ala Gly Ala Arg<br>        140                       145                       150 | | 483 |
| gga ctc agc acg gag agc atc ctc atc ccc agg cag agc gaa acc tgc<br>Gly Leu Ser Thr Glu Ser Ile Leu Ile Pro Arg Gln Ser Glu Thr Cys<br>155                     160                       165                       170 | | 531 |

```
tct cca ggg agc gct tgg tct cac ccg cag ttc gaa aaa tag gct agc    579
Ser Pro Gly Ser Ala Trp Ser His Pro Gln Phe Glu Lys Gln Ala Ser
            175                 180                 185 ctg gct gaa gct aaa gtt ctg gct aac cgt gaa ctg gac aaa tac ggt    627
Leu Ala Glu Ala Lys Val Leu Ala Asn Arg Glu Leu Asp Lys Tyr Gly
        190                 195                 200 gtt tcc gac tac tac aaa aac ctc atc aac aac gct aaa acc gtt gaa    675
Val Ser Asp Tyr Tyr Lys Asn Leu Ile Asn Asn Ala Lys Thr Val Glu
    205                 210                 215 ggt gtt aaa gct ctg atc gac gaa att ctc gca gca ctg ccg            717
Gly Val Lys Ala Leu Ile Asp Glu Ile Leu Ala Ala Leu Pro
220                 225                 230 taataagctt                                                          727

<210> SEQ ID NO 23
<211> LENGTH: 1156
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(1146)
<220> FEATURE:
<221> NAME/KEY: misc_feature
<222> LOCATION: (574)..(576)
<223> OTHER INFORMATION: amber stop codon

<400> SEQUENCE: 23
tctagataac gagggcaaaa a atg aaa aag aca gct atc gcg att gca gtg     51
                        Met Lys Lys Thr Ala Ile Ala Ile Ala Val
                         1               5                  10 gct ctg gct ggc ttc gct acc gta gcg cag gcc gat gca tcg atg acc     99
Ala Leu Ala Gly Phe Ala Thr Val Ala Gln Ala Asp Ala Ser Met Thr
                15                  20                  25 ggt ggt cag cag atg ggt gcc tca gac gag gag att cag gat gtg cca    147
Gly Gly Gln Gln Met Gly Ala Ser Asp Glu Glu Ile Gln Asp Val Pro
         30                  35                  40 ggg acg tgg tat ctg aag gcg atg acg gtg gac agg gag ttc cct gag    195
Gly Thr Trp Tyr Leu Lys Ala Met Thr Val Asp Arg Glu Phe Pro Glu
     45                  50                  55 atg aat ctg gaa tcg gtg aca ccc atg acc ctc acg acc ctg gaa ggg    243
Met Asn Leu Glu Ser Val Thr Pro Met Thr Leu Thr Thr Leu Glu Gly
 60                  65                  70 ggc aac ctg gaa gcc aag gtc acc atg ctg ata agt ggc cgg tgc cag    291
Gly Asn Leu Glu Ala Lys Val Thr Met Leu Ile Ser Gly Arg Cys Gln
 75                  80                  85                  90 gag gtg aag gcc gtc ctg gag aaa act gac gag ccg gga aaa tac acg    339
Glu Val Lys Ala Val Leu Glu Lys Thr Asp Glu Pro Gly Lys Tyr Thr
                 95                 100                 105 gcc gac ggg ggc aag cac gtg gca tac atc atc agg tcg cac gtg aag    387
Ala Asp Gly Gly Lys His Val Ala Tyr Ile Ile Arg Ser His Val Lys
             110                 115                 120 gac cac tac atc ttt tac tct gag ggc gag ctc cac ggg aag ccg gtc    435
Asp His Tyr Ile Phe Tyr Ser Glu Gly Glu Leu His Gly Lys Pro Val
         125                 130                 135 cga ggg gtc cag ctc gtt ggc aga gac ccc aag aac aac ctg gaa gcc    483
Arg Gly Val Gln Leu Val Gly Arg Asp Pro Lys Asn Asn Leu Glu Ala
     140                 145                 150 ttg gag gac ttt gag aaa gcc gca gga gcc cgc gga ctc agc acg gag    531
Leu Glu Asp Phe Glu Lys Ala Ala Gly Ala Arg Gly Leu Ser Thr Glu
155                 160                 165
```

|  |  |
|---|---|
| agc atc ctc atc ccc agg cag agc gaa acc tgc tct cca ggg tag gct<br>Ser Ile Leu Ile Pro Arg Gln Ser Glu Thr Cys Ser Pro Gly Gln Ala<br>175                                180                             185 | 579 |
| ggc ggc ggc tct ggt ggt ggt tct ggc ggc ggc tct gag ggt ggt ggc<br>Gly Gly Gly Ser Gly Gly Gly Ser Gly Gly Gly Ser Glu Gly Gly Gly<br>190                             195                            200 | 627 |
| tct gag ggt ggc ggt tct gag ggt ggc ggc tct gag gga ggc ggt tcc<br>Ser Glu Gly Gly Gly Ser Glu Gly Gly Gly Ser Glu Gly Gly Gly Ser<br>205                           210                          215 | 675 |
| ggt ggc ggc tct ggt tcc ggt gat ttt gat tat gaa aag atg gca aac<br>Gly Gly Gly Ser Gly Ser Gly Asp Phe Asp Tyr Glu Lys Met Ala Asn<br>220                           225                          230 | 723 |
| gct aat aag ggg gct atg acc gaa aat gcc gat gaa aac gcg cta cag<br>Ala Asn Lys Gly Ala Met Thr Glu Asn Ala Asp Glu Asn Ala Leu Gln<br>235                           240                         245                        250 | 771 |
| tct gac gct aaa ggc aaa ctt gat tct gtc gct act gat tac ggt gct<br>Ser Asp Ala Lys Gly Lys Leu Asp Ser Val Ala Thr Asp Tyr Gly Ala<br>                           255                          260                         265 | 819 |
| gct atc gat ggt ttc att ggt gac gtt tcc ggc ctt gct aat ggt aat<br>Ala Ile Asp Gly Phe Ile Gly Asp Val Ser Gly Leu Ala Asn Gly Asn<br>                     270                          275                        280 | 867 |
| ggt gct act ggt gat ttt gct ggc tct aat tcc caa atg gct caa gtc<br>Gly Ala Thr Gly Asp Phe Ala Gly Ser Asn Ser Gln Met Ala Gln Val<br>                  285                          290                        295 | 915 |
| ggt gac ggt gat aat tca cct tta atg aat aat ttc cgt caa tat tta<br>Gly Asp Gly Asp Asn Ser Pro Leu Met Asn Asn Phe Arg Gln Tyr Leu<br>300                           305                          310 | 963 |
| cct tcc ctc cct caa tcg gtt gaa tgt cgc cct ttt gtc ttt ggc gct<br>Pro Ser Leu Pro Gln Ser Val Glu Cys Arg Pro Phe Val Phe Gly Ala<br>315                           320                         325                        330 | 1011 |
| ggt aaa cca tat gaa ttt tct att gat tgt gac aaa ata aac tta ttc<br>Gly Lys Pro Tyr Glu Phe Ser Ile Asp Cys Asp Lys Ile Asn Leu Phe<br>                           335                          340                        345 | 1059 |
| cgt ggt gtc ttt gcg ttt ctt tta tat gtt gcc acc ttt atg tat gta<br>Arg Gly Val Phe Ala Phe Leu Leu Tyr Val Ala Thr Phe Met Tyr Val<br>                 350                          355                        360 | 1107 |
| ttt tct acg ttt gct aac ata ctg cgt aat aag gag tct taataagctt<br>Phe Ser Thr Phe Ala Asn Ile Leu Arg Asn Lys Glu Ser<br>365                           370                          375 | 1156 |

<210> SEQ ID NO 24
<211> LENGTH: 613
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(603)

<400> SEQUENCE: 24

|  |  |
|---|---|
| tctagataac gagggcaaaa a atg aaa aag aca gct atc gcg att gca gtg<br>                                         Met Lys Lys Thr Ala Ile Ala Ile Ala Val<br>                                          1                       5                           10 | 51 |
| gct ctg gct ggc ttc gct acc gta gcc cag gcc gat gga gga gag gag<br>Ala Leu Ala Gly Phe Ala Thr Val Ala Gln Ala Asp Gly Gly Glu Glu<br>                15                           20                           25 | 99 |
| att cag gat gtg tca ggg acg tgg tat ctg aag gcg atg acg gtg gac<br>Ile Gln Asp Val Ser Gly Thr Trp Tyr Leu Lys Ala Met Thr Val Asp<br>              30                            35                           40 | 147 |

```
agg gag ttc cct gag atg aat ctg gaa tcg gtg aca ccc atg acc ctc      195
Arg Glu Phe Pro Glu Met Asn Leu Glu Ser Val Thr Pro Met Thr Leu
             45                  50                  55 acg acc ctg gaa ggg ggc aac ctg gaa gcc aag gtc acc atg ctg ata      243
Thr Thr Leu Glu Gly Gly Asn Leu Glu Ala Lys Val Thr Met Leu Ile
         60                  65                  70 agt ggc cgg tgc cag gag gtg aag gcc gtc ctg gag aaa act gac gag      291
Ser Gly Arg Cys Gln Glu Val Lys Ala Val Leu Glu Lys Thr Asp Glu
 75                  80                  85                  90 ccg gga aaa tac acg gcc gac ggg ggc aag cac gtg gca tac atc atc      339
Pro Gly Lys Tyr Thr Ala Asp Gly Gly Lys His Val Ala Tyr Ile Ile
                 95                 100                 105 agg tcg cac gtg aag gac cac tac atc ttt tac tct gag ggc cag ctc      387
Arg Ser His Val Lys Asp His Tyr Ile Phe Tyr Ser Glu Gly Gln Leu
             110                 115                 120 cat ggg aag ccg gtc cga ggg gtg aag ctc gtg ggc aga gac ccc aag      435
His Gly Lys Pro Val Arg Gly Val Lys Leu Val Gly Arg Asp Pro Lys
         125                 130                 135 aac aac ctg gaa gcc ttg gag gac ttt gag aaa gcc gca gga gcc cgc      483
Asn Asn Leu Glu Ala Leu Glu Asp Phe Glu Lys Ala Ala Gly Ala Arg
140                 145                 150 gga ctc agc acg gag agc atc ctc atc ccc agg cag agc gaa acc tgc      531
Gly Leu Ser Thr Glu Ser Ile Leu Ile Pro Arg Gln Ser Glu Thr Cys
155                 160                 165                 170 tct cca ggg gat gca tcg atg acc ggt ggt cag cag atg ggt agc gct      579
Ser Pro Gly Asp Ala Ser Met Thr Gly Gly Gln Gln Met Gly Ser Ala
                 175                 180                 185 tgg tct cac ccg cag ttc gaa aaa taataagctt                          613
Trp Ser His Pro Gln Phe Glu Lys
             190

<210> SEQ ID NO 25
<211> LENGTH: 613
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(603)

<400> SEQUENCE: 25
tctagataac gagggcaaaa a atg aaa aag aca gct atc gcg att gca gtg      51
                        Met Lys Lys Thr Ala Ile Ala Ile Ala Val
                         1               5                  10 gct ctg gct ggc ttc gct acc gta gcg cag gcc gat gca tcg atg acc      99
Ala Leu Ala Gly Phe Ala Thr Val Ala Gln Ala Asp Ala Ser Met Thr
             15                  20                  25 ggt ggt cag cag atg ggt gcc tca gac gag gag att cag gat gtg cca      147
Gly Gly Gln Gln Met Gly Ala Ser Asp Glu Glu Ile Gln Asp Val Pro
         30                  35                  40 ggg acg tgg tat ctg aag gcg atg acg gtg gac agg gag ttc cct gag      195
Gly Thr Trp Tyr Leu Lys Ala Met Thr Val Asp Arg Glu Phe Pro Glu
     45                  50                  55 atg aat ctg gaa tcg gtg aca ccc atg acc ctc acg acc ctg gaa ggg      243
Met Asn Leu Glu Ser Val Thr Pro Met Thr Leu Thr Thr Leu Glu Gly
 60                  65                  70 ggc aac ctg gaa gcc aag gtc acc atg ctg ata agt ggc cgg tgc cag      291
Gly Asn Leu Glu Ala Lys Val Thr Met Leu Ile Ser Gly Arg Cys Gln
             75                  80                  85                  90
```

| | | | | | | | | | | | | | | |
|---|---|---|---|---|---|---|---|---|---|---|---|---|---|---|
| gag | gtg | aag | gcc | gtc | ctg | gag | aaa | act | gac | gag | ccg | gga | aaa | tac acg |
| Glu | Val | Lys | Ala | Val | Leu | Glu | Lys | Thr | Asp | Glu | Pro | Gly | Lys | Tyr Thr |
|  |  |  |  | 95 |  |  |  |  | 100 |  |  |  |  | 105 |

339

| | | | | | | | | | | | | | | |
|---|---|---|---|---|---|---|---|---|---|---|---|---|---|---|
| gcc | gac | ggg | ggc | aag | cac | gtg | gca | tac | atc | atc | agg | tcg | cac | gtg aag |
| Ala | Asp | Gly | Gly | Lys | His | Val | Ala | Tyr | Ile | Ile | Arg | Ser | His | Val Lys |
|  |  |  | 110 |  |  |  |  | 115 |  |  |  |  | 120 |  |

387

| | | | | | | | | | | | | | | |
|---|---|---|---|---|---|---|---|---|---|---|---|---|---|---|
| gac | cac | tac | atc | ttt | tac | tct | gag | ggc | gag | ctc | cac | ggg | aag | ccg gtc |
| Asp | His | Tyr | Ile | Phe | Tyr | Ser | Glu | Gly | Glu | Leu | His | Gly | Lys | Pro Val |
|  |  | 125 |  |  |  |  | 130 |  |  |  |  | 135 |  |  |

435

| | | | | | | | | | | | | | | |
|---|---|---|---|---|---|---|---|---|---|---|---|---|---|---|
| cga | ggg | gtc | cag | ctc | gtt | ggc | aga | gac | ccc | aag | aac | aac | ctg | gaa gcc |
| Arg | Gly | Val | Gln | Leu | Val | Gly | Arg | Asp | Pro | Lys | Asn | Asn | Leu | Glu Ala |
|  | 140 |  |  |  |  | 145 |  |  |  |  | 150 |  |  |  |

483

| | | | | | | | | | | | | | | |
|---|---|---|---|---|---|---|---|---|---|---|---|---|---|---|
| ttg | gag | gac | ttt | gag | aaa | gcc | gca | gga | gcc | cgc | gga | ctc | agc | acg gag |
| Leu | Glu | Asp | Phe | Glu | Lys | Ala | Ala | Gly | Ala | Arg | Gly | Leu | Ser | Thr Glu |
| 155 |  |  |  |  | 160 |  |  |  |  | 165 |  |  |  | 170 |

531

| | | | | | | | | | | | | | | |
|---|---|---|---|---|---|---|---|---|---|---|---|---|---|---|
| agc | atc | ctc | atc | ccc | agg | cag | agc | gaa | acc | tgc | tct | cca | ggg | agc gct |
| Ser | Ile | Leu | Ile | Pro | Arg | Gln | Ser | Glu | Thr | Cys | Ser | Pro | Gly | Ser Ala |
|  |  |  |  | 175 |  |  |  |  | 180 |  |  |  |  | 185 |

579

| | | | | | | |
|---|---|---|---|---|---|---|
| tgg | tct | cac | ccg | cag | ttc | gaa aaa taataagctt |
| Trp | Ser | His | Pro | Gln | Phe | Glu Lys |
|  |  |  | 190 |  |  |  |

613

```
<210> SEQ ID NO 26
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other

<400> SEQUENCE: 26
tatctgaagg cgatgacggt gnnknnknnk nnknnknnkn nknnknnkga atcggtgaca    60
cccatg                                                              66
```

```
<210> SEQ ID NO 27
<211> LENGTH: 72
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other
<220> FEATURE:
<221> NAME/KEY: modified_base
<222> LOCATION: (49)..(50)
<223> OTHER INFORMATION: a, c, g, t, unknown or other
<220> FEATURE:
<221> NAME/KEY: modified_base
<222> LOCATION: (52)..(53)
<223> OTHER INFORMATION: a, c, g, t, unknown or other

<400> SEQUENCE: 27
tatctgaagg cgatgacggt gnnknnknnk nnknnknnkn nknnknnknn knnkgaatcg      60
gtgacaccca tg                                                         72

<210> SEQ ID NO 28
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
```

```
<220> FEATURE:
<221> NAME/KEY: modified_base
<222> LOCATION: (34)..(35)
<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (46)..(47)
<223> OTHER INFORMATION: a, c, g, t, unknown or other
<220> FEATURE:
<221> NAME/KEY: modified_base
<222> LOCATION: (49)..(50)
<223> OTHER INFORMATION: a, c, g, t, unknown or other

<400> SEQUENCE: 28
tatctgaagg cgatgacgtg gtcannknnk nnknnknnkn nknnknnknn kaattcgctg    60
gaatcggtga caccc                                                    75

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(22)
<223> OTHER INFORMATION: a, c, g, t, unknown or other
<220> FEATURE:
<221> NAME/KEY: modified_base
<222> LOCATION: (24)..(25)
<223> OTHER INFORMATION: a, c, g, t, unknown or other
<220> FEATURE:
<221> NAME/KEY: modified_base
<222> LOCATION: (27)..(28)
<223> OTHER INFORMATION: a, c, g, t, unknown or other

<400> SEQUENCE: 29
tcacctcctg gcaccggccm nnmnnmnnca tggtgacctt ggcttc                  46

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(23)
<223> OTHER INFORMATION: a, c, g, t, unknown or other

<400> SEQUENCE: 30
aaatacacgg ccgacggagg cnnkcacgtg gcatacatca tcag                    44

<210> SEQ ID NO 31
<211> LENGTH: 51
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, c, g, t, unknown or other
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other

<400> SEQUENCE: 31
agctggaccc ctcggacmnn mnnccemnnm nnctcgccct cagagtaaaa g         51

<210> SEQ ID NO 32
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgtcggccg tgtatttacc cggctcgtca gttttctcca gtactgcctt cacctcctgg    60
caccgg                                                              66

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caggatgtgc caggacgtg gtatctgaag gcgatgacg                           39

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gttcttgggg tctctgccaa cgagctggac ccctcggac                          39

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccgcttcact gccccggctg gtcc                                          24

<210> SEQ ID NO 36
```

<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
cttctgttgt ctgttcccgg cttc            24

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ccactcccta tcagtgat            18

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cccttgaacc tcctcgttcg acc            23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gagcctgggg actttccaca ccc            23

<210> SEQ ID NO 40
<211> LENGTH: 364
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 40

Met Lys Lys Thr Ala Ile Ala Ile Ala Val Ala Leu Ala Gly Phe Ala
 1               5                  10                  15

Thr Val Ala Gln Ala Asp Gly Gly Glu Glu Ile Gln Asp Val Ser Gly
                20                  25                  30

Thr Trp Tyr Leu Lys Ala Met Thr Val Asp Arg Glu Phe Pro Glu Met
        35                  40                  45

Asn Leu Glu Ser Val Thr Pro Met Thr Leu Thr Leu Glu Gly Gly
    50                  55                  60

Asn Leu Glu Ala Lys Val Thr Met Leu Ile Ser Gly Arg Cys Gln Glu
65                  70                  75                  80

Val Lys Ala Val Leu Glu Lys Thr Asp Glu Pro Gly Lys Tyr Thr Ala
                85                  90                  95

-continued

```
Asp Gly Gly Lys His Val Ala Tyr Ile Ile Arg Ser His Val Lys Asp
            100                 105                 110
His Tyr Ile Phe Tyr Ser Glu Gly Gln Leu His Gly Lys Pro Val Arg
        115                 120                 125
Gly Val Lys Leu Val Gly Arg Asp Pro Lys Asn Asn Leu Glu Ala Leu
    130                 135                 140
Glu Asp Phe Glu Lys Ala Ala Gly Ala Arg Gly Leu Ser Thr Glu Ser
145                 150                 155                 160
Ile Leu Ile Pro Arg Gln Ser Glu Thr Cys Ser Pro Gly Gln Ala Gly
                165                 170                 175
Gly Gly Ser Gly Gly Gly Ser Gly Gly Gly Ser Glu Gly Gly Gly Ser
            180                 185                 190
Glu Gly Gly Gly Ser Glu Gly Gly Ser Glu Gly Gly Gly Ser Gly
        195                 200                 205
Gly Gly Ser Gly Ser Gly Asp Phe Asp Tyr Glu Lys Met Ala Asn Ala
    210                 215                 220
Asn Lys Gly Ala Met Thr Glu Asn Ala Asp Glu Asn Ala Leu Gln Ser
225                 230                 235                 240
Asp Ala Lys Gly Lys Leu Asp Ser Val Ala Thr Asp Tyr Gly Ala Ala
                245                 250                 255
Ile Asp Gly Phe Ile Gly Asp Val Ser Gly Leu Ala Asn Gly Asn Gly
            260                 265                 270
Ala Thr Gly Asp Phe Ala Gly Ser Asn Ser Gln Met Ala Gln Val Gly
        275                 280                 285
Asp Gly Asp Asn Ser Pro Leu Met Asn Asn Phe Arg Gln Tyr Leu Pro
    290                 295                 300
Ser Leu Pro Gln Ser Val Glu Cys Arg Pro Phe Val Phe Gly Ala Gly
305                 310                 315                 320
Lys Pro Tyr Glu Phe Ser Ile Asp Cys Asp Lys Ile Asn Leu Phe Arg
                325                 330                 335
Gly Val Phe Ala Phe Leu Leu Tyr Val Ala Thr Phe Met Tyr Val Phe
            340                 345                 350
Ser Thr Phe Ala Asn Ile Leu Arg Asn Lys Glu Ser
        355                 360

<210> SEQ ID NO 41
<211> LENGTH: 168
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 41

Met Lys Lys Thr Ala Ile Ala Ile Ala Val Ala Leu Ala Gly Phe Ala
        -20                 -15                 -10
Thr Val Ala Gln Ala Asp Gly Met Thr Val Asp Arg Glu Phe Pro Glu
    -5                  -1   1              5                  10
Met Asn Leu Glu Ser Val Thr Pro Met Thr Leu Thr Thr Leu Glu Gly
                15                  20                  25
Gly Asn Leu Glu Ala Lys Val Thr Met Leu Ile Ser Gly Arg Cys Gln
            30                  35                  40
Glu Val Lys Ala Val Leu Glu Lys Thr Asp Glu Pro Gly Lys Tyr Thr
        45                  50                  55
Ala Asp Gly Gly Lys His Val Ala Tyr Ile Ile Arg Ser His Val Lys
    60                  65                  70                  75
```

Asp His Tyr Ile Phe Tyr Ser Glu Gly Gln Leu His Gly Lys Pro Val
            80                  85                  90

Arg Gly Val Lys Leu Val Gly Arg Asp Pro Lys Asn Asn Leu Glu Ala
            95                 100                 105

Leu Glu Asp Phe Glu Lys Ala Ala Gly Ala Arg Gly Leu Ser Thr Glu
           110                 115                 120

Ser Ile Leu Ile Pro Arg Gln Ser Glu Thr Cys Ser Pro Gly Ser Ala
       125                 130                 135

Trp Ser His Pro Gln Phe Glu Lys
140                 145

<210> SEQ ID NO 42
<211> LENGTH: 412
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 42

Met Lys Lys Thr Ala Ile Ala Ile Ala Val Ala Leu Ala Gly Phe Ala
  1               5                  10                  15

Thr Val Ala Gln Ala Asp Gly Gly Glu Glu Ile Gln Asp Val Ser Gly
             20                  25                  30

Thr Trp Tyr Leu Lys Ala Met Thr Val Asp Arg Glu Phe Pro Glu Met
         35                  40                  45

Asn Leu Glu Ser Val Thr Pro Met Thr Leu Thr Thr Leu Glu Gly Gly
     50                  55                  60

Asn Leu Glu Ala Lys Val Thr Met Leu Ile Ser Gly Arg Cys Gln Glu
 65                  70                  75                  80

Val Lys Ala Val Leu Glu Lys Thr Asp Glu Pro Gly Lys Tyr Thr Ala
                 85                  90                  95

Asp Gly Gly Lys His Val Ala Tyr Ile Ile Arg Ser His Val Lys Asp
            100                 105                 110

His Tyr Ile Phe Tyr Ser Glu Gly Gln Leu His Gly Lys Pro Val Arg
        115                 120                 125

Gly Val Lys Leu Val Gly Arg Asp Pro Lys Asn Asn Leu Glu Ala Leu
    130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Cys Ser Pro Gly Gln Ala Gly
                165                 170                 175

Gly Gly Ser Gly Gly Gly Ser Gly Gly Gly Ser Glu Gly Gly Gly Ser
            180                 185                 190

Glu Gly Gly Gly Ser Glu Gly Gly Gly Ser Glu Gly Gly Gly Ser Gly
        195                 200                 205

Gly Gly Ser Gly Ser Gly Asp Phe Asp Tyr Glu Lys Met Ala Asn Ala
    210                 215                 220

Asn Lys Gly Ala Met Thr Glu Asn Ala Val Thr Pro Gln Pro Glu Glu
225                 230                 235                 240

Gln Lys Glu Arg Lys Thr Thr Glu Met Gln Ser Pro Met Gln Pro Val
                245                 250                 255

Asp Gln Ala Ser Leu Pro Gly His Cys Arg Glu Pro Pro Pro Trp Glu
            260                 265                 270

Asn Glu Ala Thr Glu Arg Ile Tyr His Phe Val Val Gly Gln Met Val

-continued

```
                275                 280                 285
Tyr Tyr Gln Cys Val Gln Gly Tyr Arg Ala Leu His Arg Gly Pro Ala
290                 295                 300

Glu Ser Val Cys Lys Met Thr His Gly Lys Thr Arg Trp Thr Gln Pro
305                 310                 315                 320

Gln Leu Ile Cys Thr Gly Glu Met Glu Thr Ser Gln Phe Pro Gly Glu
                325                 330                 335

Glu Lys Pro Gln Ala Ser Pro Glu Gly Arg Pro Ser Glu Thr Ser
                340                 345                 350

Cys Leu Val Thr Thr Thr Asp Phe Gln Ile Gln Thr Glu Met Ala Ala
                355                 360                 365

Thr Met Glu Thr Ser Ile Phe Thr Thr Glu Tyr Gln Val Ala Val Ala
370                 375                 380

Gly Cys Val Phe Leu Leu Ile Ser Val Leu Leu Ser Gly Leu Thr
385                 390                 395                 400

Trp Gln Arg Arg Gln Arg Lys Ser Arg Thr Ile
                405                 410

<210> SEQ ID NO 43
<211> LENGTH: 261
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 43

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220
```

```
Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 44
<211> LENGTH: 194
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 44

Met Lys Lys Thr Ala Ile Ala Ile Ala Val Ala Leu Ala Gly Phe Ala
1               5                   10                  15

Thr Val Ala Gln Ala Asp Gly Gly Gly Ile Arg Arg Ser Met Ser Gly
            20                  25                  30

Thr Trp Tyr Leu Lys Ala Met Thr Val Asp Arg Glu Phe Pro Glu Met
        35                  40                  45

Asn Leu Glu Ser Val Thr Pro Met Thr Leu Thr Leu Leu Lys Gly His
    50                  55                  60

Asn Leu Glu Ala Lys Val Thr Met Leu Ile Ser Gly Arg Cys Gln Glu
65                  70                  75                  80

Val Lys Ala Val Leu Gly Arg Thr Lys Glu Arg Lys Lys Tyr Thr Ala
                85                  90                  95

Asp Gly Gly Lys His Val Ala Tyr Ile Ile Pro Ser Ala Val Arg Asp
            100                 105                 110

His Val Ile Phe Tyr Ser Glu Gly Gln Leu His Gly Lys Pro Val Arg
        115                 120                 125

Gly Val Lys Leu Val Gly Arg Asp Pro Lys Asn Asn Leu Glu Ala Leu
    130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Cys Ser Pro Gly Asp Ala Ser
                165                 170                 175

Met Thr Gly Gly Gln Gln Met Gly Ser Ala Trp Ser His Pro Gln Phe
            180                 185                 190

Glu Lys

<210> SEQ ID NO 45
<211> LENGTH: 194
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 45

Met Lys Lys Thr Ala Ile Ala Ile Ala Val Ala Leu Ala Gly Phe Ala
1               5                   10                  15

Thr Val Ala Gln Ala Asp Gly Gly Arg Trp Arg Val Cys Trp Ser Gly
            20                  25                  30

Thr Trp Tyr Leu Lys Ala Met Thr Val Asp Arg Glu Phe Pro Glu Met
        35                  40                  45

Asn Leu Glu Ser Val Thr Pro Met Thr Leu Thr Gln Leu Asp Gly Lys
```

```
            50                  55                  60
Asn Leu Glu Ala Lys Val Thr Met Leu Ile Ser Gly Arg Cys Gln Glu
 65                  70                  75                  80

Val Lys Ala Val Leu Glu Leu Thr Asn Glu Gly Val Lys Tyr Thr Ala
                 85                  90                  95

Asp Gly Gly Lys His Val Ala Tyr Ile Ile Pro Ser Arg Val Ser Asp
                100                 105                 110

His Phe Ile Phe Tyr Ser Glu Gly Gln Leu His Gly Lys Pro Val Arg
                115                 120                 125

Gly Val Lys Leu Val Gly Arg Asp Pro Lys Asn Asn Leu Glu Ala Leu
130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Cys Ser Pro Gly Asp Ala Ser
                165                 170                 175

Met Thr Gly Gly Gln Gln Met Gly Ser Ala Trp Ser His Pro Gln Phe
                180                 185                 190

Glu Lys
```

<210> SEQ ID NO 46
<211> LENGTH: 194
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 46

```
Met Lys Lys Thr Ala Ile Ala Ile Ala Val Ala Leu Ala Gly Phe Ala
 1               5                  10                  15

Thr Val Ala Gln Ala Asp Ala Ser Met Thr Gly Gly Gln Gln Met Gly
                 20                  25                  30

Ala Ser Asp Glu Glu Ile Gln Asp Val Pro Gly Thr Trp Tyr Leu Lys
                 35                  40                  45

Ala Met Thr Val Gly Ser Gly Ser Ile Cys Thr Cys Ser Glu Ser Val
 50                  55                  60

Thr Pro Met Thr Leu Thr Thr Leu Glu Gly Gly Asn Leu Glu Ala Lys
 65                  70                  75                  80

Val Thr Met Val Val Arg Gly Arg Cys Gln Glu Val Lys Ala Val Leu
                 85                  90                  95

Glu Lys Thr Asp Glu Pro Gly Lys Tyr Thr Ala Asp Gly Gly Asn His
                100                 105                 110

Val Ala Tyr Ile Ile Arg Ser His Val Lys Asp His Tyr Ile Phe Tyr
                115                 120                 125

Ser Glu Gly Glu Val Met Gly Leu Pro Val Arg Gly Val Gln Leu Val
130                 135                 140

Gly Arg Asp Pro Lys Asn Asn Leu Glu Ala Leu Glu Asp Phe Glu Lys
145                 150                 155                 160

Ala Ala Gly Ala Arg Gly Leu Ser Thr Glu Ser Ile Leu Ile Pro Arg
                165                 170                 175

Gln Ser Glu Thr Cys Ser Pro Gly Ser Ala Trp Ser His Pro Gln Phe
                180                 185                 190

Glu Lys
```

<210> SEQ ID NO 47

<211> LENGTH: 194
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 47

```
Met Lys Lys Thr Ala Ile Ala Ile Ala Val Ala Leu Ala Gly Phe Ala
 1               5                  10                  15

Thr Val Ala Gln Ala Asp Ala Ser Met Thr Gly Gly Gln Gln Met Gly
            20                  25                  30

Ala Ser Asp Glu Glu Ile Gln Asp Val Pro Gly Thr Trp Tyr Leu Lys
        35                  40                  45

Ala Met Thr Val Val His Gly Val His Asp Leu Phe Leu Glu Ser Val
    50                  55                  60

Thr Pro Met Thr Leu Thr Thr Leu Glu Gly Gly Asn Leu Glu Ala Lys
65                  70                  75                  80

Val Thr Met Phe Gly Asn Gly Arg Cys Gln Glu Val Asn Ala Val Leu
                85                  90                  95

Glu Lys Thr Asp Glu Pro Gly Lys Tyr Thr Ala Asp Gly Gly Asn His
            100                 105                 110

Val Ala Tyr Ile Ile Arg Ser His Val Lys Asp His Tyr Ile Phe Tyr
        115                 120                 125

Ser Glu Gly Glu His Met Gly Trp Thr Val Arg Gly Val Gln Leu Val
    130                 135                 140

Gly Arg Asp Pro Lys Asn Asn Leu Glu Ala Leu Glu Asp Phe Glu Lys
145                 150                 155                 160

Ala Ala Gly Ala Arg Gly Leu Ser Thr Glu Ser Ile Leu Ile Pro Arg
                165                 170                 175

Gln Ser Glu Thr Cys Ser Pro Gly Ser Ala Trp Ser His Pro Gln Phe
            180                 185                 190

Glu Lys
```

<210> SEQ ID NO 48
<211> LENGTH: 196
<212> TYPE: PRT
<213> ORGANISM: Artificial Sequence
<220> FEATURE:
<223> OTHER INFORMATION: Description of Artificial Sequence: Synthetic protein sequence

<400> SEQUENCE: 48

```
Met Lys Lys Thr Ala Ile Ala Ile Ala Val Ala Leu Ala Gly Phe Ala
 1               5                  10                  15

Thr Val Ala Gln Ala Asp Ala Ser Met Thr Gly Gly Gln Gln Met Gly
            20                  25                  30

Ala Ser Asp Glu Glu Ile Gln Asp Val Pro Gly Thr Trp Tyr Leu Lys
        35                  40                  45

Ala Met Thr Val Pro Asp Leu Ser Leu Thr Leu Gln Ala Thr Ala Glu
    50                  55                  60

Ser Val Thr Pro Met Thr Leu Thr Thr Leu Glu Gly Gly Asn Leu Glu
65                  70                  75                  80

Ala Lys Val Thr Met Phe Gly Tyr Gly Arg Cys Gln Glu Val Lys Ala
                85                  90                  95

Val Leu Glu Lys Thr Asp Glu Pro Gly Lys Tyr Thr Ala Asp Gly Gly
            100                 105                 110
```

```
Asn His Val Ala Tyr Ile Ile Arg Ser His Val Lys Asp His Tyr Ile
        115                 120                 125

Phe Tyr Ser Glu Gly Glu Leu Met Gly Val Leu Val Arg Gly Val Gln
        130                 135                 140

Leu Val Gly Arg Asp Pro Lys Asn Asn Leu Glu Ala Leu Glu Asp Phe
145                 150                 155                 160

Glu Lys Ala Ala Gly Ala Arg Gly Leu Ser Thr Glu Ser Ile Leu Ile
                165                 170                 175

Pro Arg Gln Ser Glu Thr Cys Ser Pro Gly Ser Ala Trp Ser His Pro
                180                 185                 190

Gln Phe Glu Lys
        195

<210> SEQ ID NO 49
<211> LENGTH: 194
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 49

Met Lys Lys Thr Ala Ile Ala Ile Ala Val Ala Leu Ala Gly Phe Ala
 1               5                  10                  15

Thr Val Ala Gln Ala Asp Gly Val Gly Lys Arg Gly Leu Ser Gly
                20                  25                  30

Thr Trp Tyr Leu Lys Ala Met Thr Val Asp Arg Glu Phe Pro Glu Met
            35                  40                  45

Asp Leu Glu Ser Val Thr Pro Met Thr Leu Thr Gly Leu Ala Gly Gly
        50                  55                  60

Asp Leu Glu Ala Lys Val Thr Met Leu Ile Ser Gly Arg Cys Gln Glu
 65                 70                  75                  80

Val Lys Ala Val Leu Glu Gly Thr Asn Glu Leu Asp Lys Tyr Thr Ala
                85                  90                  95

Asp Gly Gly Lys His Val Ala Tyr Ile Ile His Pro His Val Thr Asp
                100                 105                 110

His Leu Ile Phe Tyr Ser Glu Gly Gln Leu His Gly Lys Pro Val Arg
            115                 120                 125

Gly Val Lys Leu Val Gly Arg Asp Pro Lys Asn Asn Leu Glu Ala Leu
        130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Cys Ser Pro Gly Asp Ala Ser
                165                 170                 175

Met Thr Gly Gly Gln Gln Met Gly Ser Ala Trp Ser His Pro Gln Phe
                180                 185                 190

Glu Lys

<210> SEQ ID NO 50
<211> LENGTH: 194
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 50

Met Lys Lys Thr Ala Ile Ala Ile Ala Val Ala Leu Ala Gly Phe Ala
```

```
                1               5                  10                 15
Thr Val Ala Gln Ala Asp Gly Gly Val Gly Arg Arg Gly Leu Ser Gly
                20                 25                 30

Thr Trp Tyr Leu Lys Ala Met Thr Val Asp Arg Glu Ser Pro Glu Met
            35                 40                 45

Asn Leu Glu Ser Val Thr Pro Met Thr Leu Thr Gly Leu Ala Gly Gly
         50                 55                 60

Asp Leu Glu Ala Lys Val Thr Met Leu Ile Ser Gly Arg Cys Gln Glu
 65                 70                 75                 80

Val Lys Ala Ala Leu Glu Gly Thr Asn Glu Leu Asp Lys Tyr Thr Ala
                85                 90                 95

Asp Gly Gly Lys His Val Val Tyr Ile Ile His Pro His Val Thr Asp
                100                105                110

His Leu Ile Phe Tyr Ser Glu Gly Gln Leu His Gly Lys Pro Val Arg
            115                120                125

Gly Val Lys Leu Val Gly Arg Asp Pro Lys Asn Asn Leu Glu Ala Leu
         130                135                140

Glu Asp Phe Glu Lys Ala Ala Gly Ala Arg Gly Leu Ser Thr Glu Ser
145                150                155                160

Ile Leu Ile Pro Arg Gln Ser Glu Thr Cys Ser Pro Gly Asp Ala Ser
                165                170                175

Met Thr Gly Gly Gln Gln Met Gly Ser Ala Trp Ser His Pro Gln Phe
            180                185                190

Glu Lys

<210> SEQ ID NO 51
<211> LENGTH: 194
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 51

Met Lys Lys Thr Ala Ile Ala Ile Ala Val Ala Leu Ala Gly Phe Ala
  1               5                  10                 15

Thr Val Ala Gln Ala Asp Gly Gly Val Gly Arg Arg Gly Leu Ser Gly
                20                 25                 30

Thr Trp Tyr Leu Lys Ala Met Thr Val Asp Arg Glu Ser Pro Glu Met
            35                 40                 45

Asn Leu Glu Ser Val Thr Pro Met Thr Leu Thr Gly Leu Ala Gly Gly
         50                 55                 60

Asp Leu Glu Ala Lys Val Thr Met Leu Ile Ser Gly Arg Cys Gln Glu
 65                 70                 75                 80

Val Lys Ala Val Leu Glu Gly Thr Asn Glu Leu Asp Lys Tyr Thr Ala
                85                 90                 95

Asp Gly Gly Lys His Val Ala Tyr Ile Ile His Pro His Val Thr Asp
                100                105                110

His Leu Ile Phe Tyr Ser Glu Gly Gln Leu His Gly Lys Pro Val Arg
            115                120                125

Gly Val Lys Leu Val Gly Arg Asp Pro Lys Asn Asn Leu Glu Ala Leu
         130                135                140

Glu Asp Phe Glu Lys Ala Ala Gly Ala Arg Gly Leu Ser Thr Glu Ser
145                150                155                160

Ile Leu Ile Pro Arg Gln Ser Glu Thr Cys Ser Pro Gly Asp Ala Ser
```

165                 170                 175
Met Thr Gly Gly Gln Gln Met Gly Ser Ala Trp Ser His Pro Gln Phe
            180                 185                 190

Glu Lys

<210> SEQ ID NO 52
<211> LENGTH: 194
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 52

Met Lys Lys Thr Ala Ile Ala Ile Ala Val Ala Leu Ala Gly Phe Ala
 1               5                  10                  15

Thr Val Ala Gln Ala Asp Gly Gly Val Gly Arg Arg Gly Leu Ser Gly
            20                  25                  30

Thr Trp Tyr Leu Lys Ala Met Thr Val Asp Arg Glu Phe Pro Glu Met
        35                  40                  45

Asn Leu Glu Ser Val Thr Pro Met Thr Leu Thr Gly Leu Ala Gly Gly
     50                  55                  60

Asp Leu Glu Ala Lys Val Thr Met Leu Ile Ser Gly Arg Cys Gln Glu
65                  70                  75                  80

Val Lys Ala Val Leu Glu Gly Thr Asn Glu Leu Asp Lys Tyr Thr Ala
                85                  90                  95

Asp Gly Gly Lys His Val Ala Tyr Ile Ile Ser His Val Thr Asp
            100                 105                 110

His Leu Ile Phe Tyr Ser Glu Gly Gln Leu His Gly Lys Pro Val Arg
        115                 120                 125

Gly Val Lys Leu Val Gly Arg Asp Pro Lys Asn Asn Leu Glu Ala Leu
    130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Cys Ser Pro Gly Asp Ala Ser
                165                 170                 175

Met Thr Gly Gly Gln Gln Met Gly Ser Ala Trp Ser His Pro Gln Phe
            180                 185                 190

Glu Lys

<210> SEQ ID NO 53
<211> LENGTH: 232
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 53

Met Lys Lys Thr Ala Ile Ala Ile Ala Val Ala Leu Ala Gly Phe Ala
 1               5                  10                  15

Thr Val Ala Gln Ala Asp Gly Gly Val Gly Arg Arg Gly Leu Ser Gly
            20                  25                  30

Thr Trp Tyr Leu Lys Ala Met Ala Val Asp Arg Glu Phe Pro Glu Met
        35                  40                  45

Asn Leu Glu Ser Val Thr Pro Met Thr Leu Thr Gly Leu Ala Gly Gly
     50                  55                  60

```
Asp Leu Gly Val Lys Val Thr Met Leu Ile Ser Gly Arg Cys Gln Glu
 65                  70                  75                  80

Val Lys Ala Val Leu Glu Gly Thr Asn Glu Leu Asp Lys Tyr Thr Ala
                 85                  90                  95

Asp Gly Gly Lys His Val Ala Tyr Ile Ile His Ser His Val Thr Asp
            100                 105                 110

His Leu Ile Leu Tyr Ser Glu Gly Gln Leu His Gly Lys Pro Val Arg
        115                 120                 125

Gly Val Lys Leu Val Gly Arg Asp Pro Lys Asn Asn Leu Glu Ala Leu
130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Cys Ser Pro Gly Ser Ala Trp
                165                 170                 175

Ser His Pro Gln Phe Glu Lys Gln Ala Ser Leu Ala Glu Ala Lys Val
            180                 185                 190

Leu Ala Asn Arg Glu Leu Asp Lys Tyr Gly Val Ser Asp Tyr Tyr Lys
        195                 200                 205

Asn Leu Ile Asn Asn Ala Lys Thr Val Glu Gly Val Lys Ala Leu Ile
210                 215                 220

Asp Glu Ile Leu Ala Ala Leu Pro
225                 230

<210> SEQ ID NO 54
<211> LENGTH: 232
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 54

Met Lys Lys Thr Ala Ile Ala Ile Ala Val Ala Leu Ala Gly Phe Ala
  1               5                  10                  15

Thr Val Ala Gln Ala Asp Gly Gly Glu Glu Ile Gln Asp Val Ser Gly
                 20                  25                  30

Thr Trp Tyr Leu Lys Ala Met Thr Val Asp Arg Glu Phe Pro Glu Met
         35                  40                  45

Asn Leu Glu Ser Val Thr Pro Met Thr Leu Thr Thr Leu Glu Gly Gly
     50                  55                  60

Asn Leu Glu Ala Lys Val Thr Met Leu Ile Ser Gly Arg Cys Gln Glu
 65                  70                  75                  80

Val Lys Ala Val Leu Glu Lys Thr Asp Glu Pro Gly Lys Tyr Thr Ala
                 85                  90                  95

Asp Gly Gly Lys His Val Ala Tyr Ile Ile Arg Ser His Val Lys Asp
            100                 105                 110

His Tyr Ile Phe Tyr Ser Glu Gly Gln Leu His Gly Lys Pro Val Arg
        115                 120                 125

Gly Val Lys Leu Val Gly Arg Asp Pro Lys Asn Asn Leu Glu Ala Leu
130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Cys Ser Pro Gly Ser Ala Trp
                165                 170                 175

Ser His Pro Gln Phe Glu Lys Gln Ala Ser Leu Ala Glu Ala Lys Val
            180                 185                 190
```

-continued

```
Leu Ala Asn Arg Glu Leu Asp Lys Tyr Gly Val Ser Asp Tyr Tyr Lys
            195                 200                 205

Asn Leu Ile Asn Asn Ala Lys Thr Val Glu Gly Val Lys Ala Leu Ile
            210                 215                 220

Asp Glu Ile Leu Ala Ala Leu Pro
225                 230

<210> SEQ ID NO 55
<211> LENGTH: 375
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 55

Met Lys Lys Thr Ala Ile Ala Ile Ala Val Ala Leu Ala Gly Phe Ala
 1               5                  10                  15

Thr Val Ala Gln Ala Asp Ala Ser Met Thr Gly Gly Gln Gln Met Gly
            20                  25                  30

Ala Ser Asp Glu Glu Ile Gln Asp Val Pro Gly Thr Trp Tyr Leu Lys
        35                  40                  45

Ala Met Thr Val Asp Arg Glu Phe Pro Glu Met Asn Leu Glu Ser Val
    50                  55                  60

Thr Pro Met Thr Leu Thr Thr Leu Glu Gly Gly Asn Leu Glu Ala Lys
65                  70                  75                  80

Val Thr Met Leu Ile Ser Gly Arg Cys Gln Glu Val Lys Ala Val Leu
                85                  90                  95

Glu Lys Thr Asp Glu Pro Gly Lys Tyr Thr Ala Asp Gly Gly Lys His
            100                 105                 110

Val Ala Tyr Ile Ile Arg Ser His Val Lys Asp His Tyr Ile Phe Tyr
        115                 120                 125

Ser Glu Gly Glu Leu His Gly Lys Pro Val Arg Gly Val Gln Leu Val
    130                 135                 140

Gly Arg Asp Pro Lys Asn Asn Leu Glu Ala Leu Glu Asp Phe Glu Lys
145                 150                 155                 160

Ala Ala Gly Ala Arg Gly Leu Ser Thr Glu Ser Ile Leu Ile Pro Arg
                165                 170                 175

Gln Ser Glu Thr Cys Ser Pro Gly Gln Ala Gly Gly Ser Gly Gly
            180                 185                 190

Gly Ser Gly Gly Gly Ser Glu Gly Gly Ser Glu Gly Gly Gly Ser
        195                 200                 205

Glu Gly Gly Gly Ser Glu Gly Gly Ser Gly Gly Ser Gly Ser
    210                 215                 220

Gly Asp Phe Asp Tyr Glu Lys Met Ala Asn Ala Asn Lys Gly Ala Met
225                 230                 235                 240

Thr Glu Asn Ala Asp Glu Asn Ala Leu Gln Ser Asp Ala Lys Gly Lys
                245                 250                 255

Leu Asp Ser Val Ala Thr Asp Tyr Gly Ala Ala Ile Asp Gly Phe Ile
            260                 265                 270

Gly Asp Val Ser Gly Leu Ala Asn Gly Asn Gly Ala Thr Gly Asp Phe
        275                 280                 285

Ala Gly Ser Asn Ser Gln Met Ala Gln Val Gly Asp Gly Asp Asn Ser
    290                 295                 300

Pro Leu Met Asn Asn Phe Arg Gln Tyr Leu Pro Ser Leu Pro Gln Ser
```

```
                                305                 310                 315                 320
Val Glu Cys Arg Pro Phe Val Phe Gly Ala Gly Lys Pro Tyr Glu Phe
                    325                 330                 335

Ser Ile Asp Cys Asp Lys Ile Asn Leu Phe Arg Gly Val Phe Ala Phe
                340                 345                 350

Leu Leu Tyr Val Ala Thr Phe Met Tyr Val Phe Ser Thr Phe Ala Asn
            355                 360                 365

Ile Leu Arg Asn Lys Glu Ser
        370                 375

<210> SEQ ID NO 56
<211> LENGTH: 194
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 56

Met Lys Lys Thr Ala Ile Ala Ile Ala Val Ala Leu Ala Gly Phe Ala
  1               5                  10                  15

Thr Val Ala Gln Ala Asp Gly Gly Glu Ile Gln Asp Val Ser Gly
             20                  25                  30

Thr Trp Tyr Leu Lys Ala Met Thr Val Asp Arg Glu Phe Pro Glu Met
             35                  40                  45

Asn Leu Glu Ser Val Thr Pro Met Thr Leu Thr Thr Leu Glu Gly Gly
 50                  55                  60

Asn Leu Glu Ala Lys Val Thr Met Leu Ile Ser Gly Arg Cys Gln Glu
 65                  70                  75                  80

Val Lys Ala Val Leu Glu Lys Thr Asp Glu Pro Gly Lys Tyr Thr Ala
                 85                  90                  95

Asp Gly Gly Lys His Val Ala Tyr Ile Ile Arg Ser His Val Lys Asp
                100                 105                 110

His Tyr Ile Phe Tyr Ser Glu Gly Gln Leu His Gly Lys Pro Val Arg
            115                 120                 125

Gly Val Lys Leu Val Gly Arg Asp Pro Lys Asn Asn Leu Glu Ala Leu
130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Cys Ser Pro Gly Asp Ala Ser
                165                 170                 175

Met Thr Gly Gly Gln Gln Met Gly Ser Ala Trp Ser His Pro Gln Phe
            180                 185                 190

Glu Lys

<210> SEQ ID NO 57
<211> LENGTH: 194
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 57

Met Lys Lys Thr Ala Ile Ala Ile Ala Val Ala Leu Ala Gly Phe Ala
  1               5                  10                  15

Thr Val Ala Gln Ala Asp Ala Ser Met Thr Gly Gly Gln Gln Met Gly
             20                  25                  30
```

```
Ala Ser Asp Glu Glu Ile Gln Asp Val Pro Gly Thr Trp Tyr Leu Lys
        35                  40                  45

Ala Met Thr Val Asp Arg Glu Phe Pro Glu Met Asn Leu Glu Ser Val
 50                  55                  60

Thr Pro Met Thr Leu Thr Thr Leu Glu Gly Gly Asn Leu Glu Ala Lys
 65                  70                  75                  80

Val Thr Met Leu Ile Ser Gly Arg Cys Gln Glu Val Lys Ala Val Leu
                 85                  90                  95

Glu Lys Thr Asp Glu Pro Gly Lys Tyr Thr Ala Asp Gly Gly Lys His
            100                 105                 110

Val Ala Tyr Ile Ile Arg Ser His Val Lys Asp His Tyr Ile Phe Tyr
        115                 120                 125

Ser Glu Gly Glu Leu His Gly Lys Pro Val Arg Gly Val Gln Leu Val
    130                 135                 140

Gly Arg Asp Pro Lys Asn Asn Leu Glu Ala Leu Glu Asp Phe Glu Lys
145                 150                 155                 160

Ala Ala Gly Ala Arg Gly Leu Ser Thr Glu Ser Ile Leu Ile Pro Arg
                165                 170                 175

Gln Ser Glu Thr Cys Ser Pro Gly Ser Ala Trp Ser His Pro Gln Phe
            180                 185                 190

Glu Lys

<210> SEQ ID NO 58
<211> LENGTH: 158
<212> TYPE: PRT
<213> ORGANISM: Homo sapiens

<400> SEQUENCE: 58

His His Leu Leu Ala Ser Asp Glu Glu Ile Gln Asp Val Ser Gly Thr
 1               5                  10                  15

Trp Tyr Leu Lys Ala Met Thr Val Asp Arg Glu Phe Pro Glu Met Asn
             20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Cys Gln Glu Val
 50                  55                  60

Lys Ala Val Leu Glu Lys Thr Asp Glu Pro Gly Lys Tyr Thr Ala Asp
 65                  70                  75                  80

Gly Gly Lys His Val Ala Tyr Ile Ile Arg Ser His Val Lys Asp His
                 85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 59
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      6xHis tag

<400> SEQUENCE: 59

His His His His His His
 1               5
```

MUTEINS OF HUMAN TEAR LIPOCALIN

CROSS-REFERENCE TO RELATED APPLICATIONS

This application is a National Stage application of PCT/EP2004/009447, filed Aug. 24, 2004, which claims priority from International Application No. PCT/EP20043/009404, filed Aug. 25, 2003.

FIELD

The present invention relates to novel muteins derived from tear lipocalin or a homologue thereof. In particular, the invention relates to a mutein of human tear lipocalin. The invention also refers to a corresponding nucleic acid molecule encoding such a mutein and to a method for its generation. The invention further refers to a method for producing such a mutein. Finally, the invention is directed to a pharmaceutical composition comprising such a lipocalin mutein as well as to various use of the mutein.

BACKGROUND

The members of the lipocalin protein family (Pervaiz, S., and Brew, K. (1987) *FASEB J.* 1, 209-214) are typically small, secreted proteins which are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signaling, and the synthesis of prostaglandins. The lipocalins have also been implicated in the regulation of the immune response and the mediation of cell homoeostasis (reviewed, for example, in Flower, D. R. (1996) *Biochem. J.* 318, 1-14 and Flower, D. R. et al. (2000) *Biochim. Biophys. Acta* 1482, 9-24).

The lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. One end of the barrel is sterically blocked by the N-terminal peptide segment that runs across its bottom as well as three peptide loops connecting the β-strands. The other end of the β-barrel is open to the solvent and encompasses a target-binding site, which is formed by four peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350).

Human tear pre-albumin, now called tear lipocalin (TLPC), was originally described as a major protein of human tear fluid (approximately one third of the total protein content) but has recently also been identified in several other secretory tissues including prostate, nasal mucosa and tracheal mucosa. Homologous proteins have been found in rat, pig, dog and horse. Tear lipocalin is an unusual lipocalin member because of its high promiscuity for relative insoluble lipids and binding characteristics that differ from other members of this protein family (reviewed in Redl, B. (2000) *Biochim. Biophys. Acta* 1482, 241-248). A remarkable number of lipophilic compounds of different chemical classes such as fatty acids, fatty alcohols, phospholipids, glycolipids and cholesterol are endogenous ligands of this protein. Interestingly, in contrast to other lipocalins the strength of ligand (target) binding correlates with the length of the hydrocarbon tail both for alkyl amides and fatty acids. Thus, tear lipocalin binds most strongly the least soluble lipids (Glasgow, B. J. et al. (1995) *Curr. Eye Res.* 14, 363-372; Gasymov, O. K. et al. (1999) *Biochim. Biophys. Acta* 1433, 307-320).

The precise biological function of human tear lipocalin has not been fully elucidated so far and is still a matter of controversy. In tear fluid, it appears to be most important for the integrity of the tear film by removing lipids from the mucous surface of the eye to the liquid phase (reviewed in Gasymov, O. K. et al. (1999), supra). However, it displays additional activities in vitro that are very unusual among lipocalins, namely inhibition of cystein proteinases as well as non-specific endonuclease activity (van't Hof, W. et al. (1997) *J. Biol. Chem.* 272, 1837-1841; Yusifov, T. N. et al. (2000) *Biochem. J.* 347, 815-819). Recently, it has been demonstrated that tear lipocalin is able to bind several lipid peroxidation products in vitro resulting in the hypothesis that it might function as a physiological oxidative-stress-induced scavenger of potentially harmful lipophilic molecules (Lechner, M. et al. (2001) *Biochem. J.* 356, 129-135).

Proteins, which selectively bind to their corresponding targets by way of non-covalent interaction, play a crucial role as reagents in biotechnology, medicine, bioanalytics as well as in the biological and life sciences in general. Antibodies, i.e. immunoglobulins, are a prominent example of this class of proteins. Despite the manifold needs for such proteins in conjunction with recognition, binding and/or separation of ligands/targets, almost exclusively immunoglobulins are currently used. The application of other proteins with defined ligand-binding characteristics, for example the lectins, has remained restricted to special cases.

Rather recently, members of the lipocalin family have become subject of research concerning proteins having defined ligand-binding properties. The PCT publication WO 99/16873 discloses the class of so-called ANTICALINS®; i.e. polypeptides of the lipocalin family with mutated amino acid positions in the region of the four peptide loops, which are arranged at the end of the cylindrical β-barrel structure encompassing the binding pocket, and which correspond to those segments in the linear polypeptide sequence comprising the amino acid positions 28 to 45, 58 to 69, 86 to 99, and 114 to 129 of the bilin-binding protein of *Pieris brassicae*. The PCT publication WO 00/75308 discloses muteins of the bilin-binding protein, which specifically bind digoxigenin, whereas the International Patent Applications WO 03/029463 and WO 03/029471 relate to muteins of the human neutrophil gelatinase-associated lipocalin and apolipoprotein D, respectively. In order to further improve and fine tune ligand affinity, specificity as well as folding stability of a lipocalin variant various approaches using different members of the lipocalin family have been proposed (Skerra, A. (2001) *Rev. Mol. Biotechnol.* 74, 257-275; Schlehuber, S., and Skerra, A. (2002) *Biophys. Chem.* 96, 213-228), such as the replacement of additional amino acid residues.

However, for various applications it could also be advantageous to have more than one binding site per molecule available—either the natural binding pocket plus an engineered additional (protein)-binding site or two different engineered binding sites. For example, it could be considered to use lipocalin muteins as adapter or linker molecules which may be attached to a given binding partner via binding site I, whereas binding site II is used for screening/selection purposes or the like. One possibility to achieve this goal is the use of fusion proteins comprising two lipocalin muteins of same or different binding specificity, which are coupled to each other by a peptide linker. Such fusion proteins, also called "duocalins", are described in WO 99/16873 and also by Schlehuber, S., and Skerra, A. (2001), *Biol. Chem.* 382, 1335-1342, for example.

Recently high-affinity histamine-binding proteins have been identified in the saliva of *Rhipicephalus appendiculatus* ticks (Paesen, G. C. et al. (1999) *Mol. Cell* 3, 661-671). These proteins sequester histamine at the wound site, outcompeting histamine receptors for the ligand in order to suppress inflammation during blood feeding. The crystal structure of these histamine-binding proteins has revealed a lipocalin fold novel in containing two binding sites for histamine having different binding affinities. The sites, one of which is a typical lipocalin binding site, are orthogonally arranged and highly rigid, forming an unusually polar internal surface that specifically complements the molecular properties of histamine. A related protein termed SHBP, which is secreted by a rodent- and cattle-feeding tick, binds both histamine and serotonin at the two different binding sites (Sangamnatdej, S. et al. (2002) *Insect Mol. Biol.* 11, 79-86). The high-affinity binding site lies perpendicular to the long axis of the β-barrel leading to distortions in the protein structure compared with other lipocalins. Thus, it appears as if such a binding site cannot be engineered in any given lipocalin. On the other hand, since the binding sites are rather buried in the core of the β-barrel there appear to be sterical limitations with regard to ligand size.

Thus, there remains a need for the generation of binding proteins that uses different binding sites and/or alternative lipocalin scaffolds, simply for the reason to have more options for practical realisation.

BRIEF SUMMARY OF THE INVENTION

Accordingly, it is an object of the invention to provide alternative lipocalin muteins having binding affinity to a given target.

This object is accomplished by a lipocalin mutein having the features of the independent claims as well as the method for its generation.

In one embodiment such a lipocalin mutein is a mutein derived from a polypeptide of tear lipocalin or a homologue thereof, wherein the mutein comprises at least two mutated amino acid residues at any sequence position in the N-terminal peptide stretch and the three peptide loops BC, DE, and FG (cf. FIG. 2) arranged at the end of the β-barrel structure that is located opposite to the natural lipocalin binding pocket, wherein said tear lipocalin or homologue thereof has at least 60% sequence homology with human tear lipocalin, and wherein the mutein binds a given target with detectable affinity.

In more illustrative terms, this embodiment is based on the finding of the inventors that amino acids in the three loops at the closed end of the internal ligand binding site of a tear lipocalin and/or the N-terminal peptide stretch of the tear lipocalin (cf. FIG. 1) can be mutated in order to obtain lipocalin muteins that bind a given target with determinable affinity. Thus, the invention provides a structurally new class of lipocalin muteins with antibody-like binding properties. This means that these muteins can be used in the same way for the generation of new binding proteins with a predetermined specificity as the class of the above mentioned so-called Anticalins® (lipocalin muteins which are derived from the proteins of the lipocalin family such as the bilin-binding protein of *Pieris brassicae*, in which amino acid positions in the four peptide loops positioned at the open end of the ligand binding site are mutated). For this reason, these new lipocalin muteins of the present invention are also considered to belong to these lipocalin muteins designated ANTICALINS®.

In another embodiment, a mutein of the invention is also a mutein derived from a polypeptide of tear lipocalin or a homologue thereof, wherein the mutein comprises at least two mutated amino acid residues at any sequence position in the four peptide loops AB, CD, EF, and GH (cf. FIG. 2) encompassing the natural lipocalin binding pocket, wherein said tear lipocalin or homologue thereof has at least 60% sequence homology with human tear lipocalin, and wherein the mutein binds a given target with detectable affinity. Accordingly, this embodiment provides for a new class of scaffold in which amino acids in the four loops at the open end of the ligand binding site of the lipocalins can be mutated for the generation of binding molecules against a desired target.

In yet another embodiment the invention relates to a mutein derived from a polypeptide of tear lipocalin or a homologue thereof, wherein the mutein comprises at least two mutated amino acid residues at any sequence position in the N-terminal region and the three peptide loops BC, DE, and FG arranged at the end of the β-barrel structure that is located opposite to the natural lipocalin binding pocket, wherein the mutein comprises at least two mutated amino acid residues at any sequence position in the four peptide loops AB, CD, EF, and GH encompassing the natural lipocalin binding pocket, wherein said tear lipocalin or homologue thereof has at least 60% sequence homology with human tear lipocalin, and wherein the mutein binds at least one given target with detectable affinity.

Thus, the invention also provides for the first time a monomeric lipocalin mutein (ANTICALIN®) that due to the presence of two binding sites can have binding specifity for two given ligands. Such a bispecific molecule can be considered to be functionally equivalent to a bispecific antibody molecule such as a bispecific diabody. However, compared to a bispecific diabody (or antibody fragment in general), this new class of bispecific lipocalin muteins (ANTICALINS®) has the advantage that it is composed only of one polypeptide chain whereas a diabody consists of two polypeptide chains that are non-covalently associated with each other.

DETAILED DESCRIPTION

A bispecific lipocalin mutein of this new class of binding proteins may be used as an adapter molecule. For example, when having binding affinity to two different receptors, such a bispecific lipocalin molecule can cross-link these receptors. An example of such a lipocalin mutein (ANTICALIN®) would be a mutein, wherein the first binding site binds to an apoptose receptor such as the CD95 (also known as Fas or Apo 1 receptor) and the second binding site can bind to a cell surface receptor, which is expressed on the same cell. Binding of such a bispecific mutein in a bicellular manner may result in mutual cross-linking of the CD95 apoptose receptor and the second cell surface receptor target antigen, which can effectively induce apoptosis of the cells (cf. Jung, G. et al. (2001) *Cancer Res.* 61, 1846-1848). However such a bispecific mutein may also have only binding affinity for one given target. Such a mutein may be useful as a molecular storage for drugs that are to be slowly released into the blood stream.

The term "mutagenesis" as used herein means that the experimental conditions are chosen such that the amino acid naturally occurring at a given sequence position of the lipocalin used can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of (the respective segment) of the wild type protein. Such an insertion of deletion may be introduced independently from each other in any of the peptide segments that can be subjected to mutagenesis in the invention. In one exemplary embodiment of the invention, an insertion of several mutations is introduced in the loop AB of the selected lipocalin scaffold (cf. Examples 2 and 28, respectively). The term "random mutagenesis" means that no predetermined single amino acid (mutation) is present at a certain sequence position but that at least two amino acids can be incorporated into a selected sequence position during mutagenesis with a certain probability.

Such experimental conditions can, for example, be achieved by incorporating codons with a degenerate base composition into a nucleotide acid encoding the respective lipocalin employed. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of a mutein. It is also possible, as described by Wang, L., et al. (2001) *Science* 292, 498-500, or Wang, L., and Schultz, P. G. (2002) *Chem. Commun.* 1, 1-11, to use "artificial" codons such as UAG which are usually recognized as stop codons in order to insert other unusual amino acids, for example o-methyl-L-tyrosine or p-aminophenylalanine.

The term "tear lipocalin" as used herein is not limited to the human tear lipocalin (SWISS-PROT Data Bank Accession Number M90424) but is intended to include all polypeptides having the structurally conversed lipocalin fold as well as a sequence homology or a sequence identity with respect to the amino acid sequence of the human tear lipocalin of at least 60%. The term lipocalin fold is used in its regular meaning as used, e.g., in Flower, D. R. (1996), supra, to describe the typical three-dimensional lipocalin structure with a conformationally conserved β-barrel as a central motif made of a cylindrically closed β-sheet of eight antiparallel strands, wherein the open end of the barrel the β-strands are connected by four loops in a pairwise manner so that the binding pocket is formed (see also FIG. 2).

The definition of the peptide loops as used in the present invention is also in accordance with the regular meaning of the term lipocalin fold and is as follows and also illustrated in FIG. 2: The peptide loop (segment) AB connects the β-strands A and B of the cylindrically closed β-sheet, the peptide loop CD connects the β-strands C and D, the peptide loop EF connects the β-strands E and F, the peptide loop GH connects the β-strands G and H, the peptide loop BC connects the β-strands B and C, the loop DE connects the β-strands D and E, and the loop FG connects the β-strands F and G. As can be seen from FIG. 2 the loops AB, CD, EF and GH form the known binding site of the lipocalins (which was therefore called the open end), whereas, as found in the present invention, the loops BC, DE and FG can be used together with the N-terminal peptide stretch to form a second binding site which is located at the closed end of the β-barrel.

In accordance with the above, the term "tear lipocalin" includes structural homologues, already identified or yet to be isolated, from other species which have an amino acid sequence homology or sequence identity of more than about 60%. The term "homology" as used herein in its usual meaning and includes identical amino acids as well as amino acids which are regarded to be conservative substitutions (for example, exchange of a glutamate residue by a aspartate residue) at equivalent positions in the linear amino acid sequence of two proteins that are compared with each other. The term "sequence identity" or "identity" as used in the present invention means the percentage of pair-wise identical residues—following homology alignment of a sequence of a polypeptide of the present invention with a sequence in question—with respect to the number of residues in the longer of these two sequences.

The percentage of sequence homology or sequence identity is determined herein using the program BLASTP, version blastp 2.2.5 (Nov. 16, 2002; cf. Altschul, S. F. et al. (1997) *Nucl. Acids Res.* 25, 3389-3402). The percentage of homology is based on the alignment of the entire polypeptide sequences (matrix: BLOSUM 62; gap costs: 11.1; cutoff value set to $10^{-3}$) including the propeptide sequences, using the human tear lipocalin as reference in a pairwise comparison. It is calculated as the percentage of numbers of "positives" (homologous amino acids) indicated as result in the BLASTP program output divided by the total number of amino acids selected by the program for the alignment. It is noted in this connection that this total number of selected amino acids can differ from the length of the tear lipocalin (176 amino acids including the propeptide) as it is seen in the following.

Examples of homologues proteins are Von Ebners gland protein 1 of *Rattus norvegicus* (VEGP protein; SWISS-PROT Data Bank Accession Numbers P20289) with a sequence homology of ca. 70% (125 positives/178 positions including the propeptide; when the 18 residues long propeptides containing 13 "positives" are not taken into account: 112 positives/160, resulting also in an homology of ca. 70%), Von Ebners gland protein 2 of *Rattus norvegicus* (VEG protein 2; SWISS-PROT Data Bank Accession Numbers P41244) with a sequence homology of ca. 71% (127 positives/178 including the propeptide; when the 18 residues long propeptides are not taken into account: 114 positives/160, the homology is determined to be also ca. 71%), Von Ebners gland protein 2 of *Sus scrofra* (pig) (LCN1; SWISS-PROT Data Bank Accession Numbers P53715) with a sequence homology of about 74% (131 positives/176 positions including the propeptide; when the 18 residues long propeptides containing 16 "positives" are not taken into account: 115 positives/158, resulting in an homology of ca. 73%), or the Major allergen Can f1 precursor of dog (ALL 1, SWISS-PROT Data Bank Accession Numbers 018873) with a sequence homology of ca. 70%, (122 positives/174 positions, or 110 positives/156=ca. 70% homology, when the propeptides with 12 positives are excluded) as determined with the program BLASTP as explained above. Such a structural homologue of the tear lipocalin can be derived from any species, i.e. from prokaryotic as well as from eukaryotic organisms. In case of eukaryotic organisms, the structural homologue can be derived from invertebrates as well as vertebrates such as mammals (e.g., human, monkey, dog, rat or mouse) or birds or reptiles.

In case a protein other than tear lipocalin is used in the present invention, the definition of the mutated sequence positions given for tear lipocalin can be assigned to the other lipocalin with the help of published sequence alignments or alignments methods which are available to the skilled artisan. A sequence alignment can, for example, be carried out as explained in WO 99/16873 (cf. FIG. 3 therein), using an published alignment such as the one in FIG. 1 of Redl, B. (2000) *Biochim. Biophys. Acta* 1482, 241-248. If the three-dimensional structure of the lipocalins are available structural superpositions can also be used for the determination of those sequence positions that are to be subjected to mutagenesis in the present invention. Other methods of structural analysis such as multidimensional nuclear magnetic resonance spectroscopy can also be employed for this purpose.

The homologue of tear lipocalin can also be a mutein protein of tear lipocalin itself, in which amino acid substitutions are introduced at positions other than the positions selected in the present invention. For example, such a mutein can be a protein in which positions at the solvent exposed surface of the β-barrel are mutated compared to the wild type sequence of the tear lipocalin in order to increase the solubility or the stability of the protein.

In general, the term "tear lipocalin" includes all proteins that have a sequence homology or sequence identity of more than 60%, 70% 80%, 85%, 90%, or 95% in relation to the human tear lipocalin (SWISS-PROT Data Bank Accession Number M90424).

In one preferred embodiment of the invention the mutein as disclosed herein is derived from human tear lipocalin. In other preferred embodiments the mutein is derived from the VEGP protein, VEG protein 2, LCN 1, or ALL 1 protein.

If the binding site at the closed end of the β-barrel is used, the mutein according to the invention typically comprises mutations at any two or more of the sequence positions in the peptide segments corresponding to the sequence positions 7-14, 41-49, 69-77, and 87-98 of the linear polypeptide sequence of human tear lipocalin. The positions 7-14 are part of the N-terminal peptide stretch, the positions 41-49 are comprised in the BC loop, the positions 60-77 are comprised in the DE loop and the positions 87-98 are comprised in the FG loop.

In more specific embodiments of those muteins the mutations are introduced at those sequence positions, which correspond to the positions 8, 9, 10, 11, 12, 13, 43, 45, 47, 70, 72, 74, 75, 90, 92, 94, and 97 of human tear lipocalin. Usually, such a mutein comprises mutations at 5-10 or 12-16 or all 17 of the sequence positions.

In case the binding site at the open end of the β-barrel is subjected to mutagenesis a lipocalin mutein according to the invention comprises mutations at any two or more of the sequence positions in the peptide segments corresponding to the sequence positions 24-36, 53-66, 79-84, and 103-110 of the linear polypeptide sequence of human tear lipocalin. The positions 24-36 are comprised in the AB loop, the positions 53-66 are comprised in the CD loop, the positions 69-77 are comprised in the EF loop and the positions 103-110 are comprised in the GH loop. In one embodiment of the invention, an insertion of 1 to 6 amino acid residues, preferably of 2 to 4 amino acid residues, is introduced into the peptide segment hat is formed by the sequence positions corresponding to sequence positions 24-36 of human tear lipocalin. This insertion can be included at any position within this segment. In one exemplary embodiment, this insertion is introduced between sequence positions 24 and 25 of human tear lipocalin. However, it is also noted again that the introduction of a stretch of at least two amino acids into a peptide segment that is part of the binding sites used here, is not limited to the segment comprising residues 24-26 but can be included in any segment participating in the formation of one of the two binding sites chosen herein.

Accordingly, a mutein having two binding sites comprises mutations at any two or more of the sequence positions in the peptide segments corresponding to the sequence positions 7-14, 41-49, 69-77, and 87-97 of the linear polypeptide sequence of human tear lipocalin and additional mutations at any two or more of the sequence positions in the peptide segments corresponding to the sequence positions 24-36, 53-66, 79-84, and 103-110 of the linear polypeptide sequence of human tear lipocalin.

In this respect it is noted that the number of the segments (loops) defined above which are used for mutagenesis can vary (the N-terminal peptide stretch is included in the meaning of the term segment or loop). It is not necessary to mutate all four of these segments all together of each of the two binding sites, for example in a concerted mutagenesis. But it is also possible to introduce mutations only in one, two or three segments of each binding site in order to generate a mutein having detectable affinity to a given target. Therefore, it is possible to subject, for example, only two or three segments at the closed end of the β-barrel to mutagenesis if a binding molecule with only one engineered binding site is wanted. If this molecule is then wanted to have binding affinity towards a second target, sequence positions in any of the four loops of the second binding site can then be mutated. It is also possible, however, to mutate peptide loops of both binding sites, even if a given target is to be bound by one of the binding site only.

The lipocalin muteins of the invention may comprise the wild type (natural) amino acid sequence outside the mutated segments. On the other hand, the lipocalin muteins disclosed herein may also contain amino acid mutations outside the sequence positions subjected to mutagenesis as long as those mutations do not interfere with the binding activity and the folding of the mutein. Such mutations can be accomplished very easily on DNA level using established standard methods (Sambrook, J. et al. (1989) *Molecular Cloning: A Laboratory Manual*, 2nd Ed., Cold Spring Harbor Laboratory Press, Cold Spring Harbor, N.Y.). Possible alterations of the amino acid sequence are insertions or deletions as well as amino acid substitutions. Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence.

Such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target (cf. Examples 17-19 and 24). In one embodiment, a mutation is introduced in at least one of the sequence positions (of the lipocalin framework) that correspond to sequence positions 21, 50, 51 and 83 of the linear polypeptide sequence of human tear lipocalin. Furthermore, mutations can be introduced in order to modulate certain characteristics of the mutein such as to improve folding stability or water solubility or to reduce aggregation tendency, if necessary.

The lipocalin muteins of the invention are able to bind the desired target with detectable affinity, i.e. with an affinity constant of preferably at least $10^5$ $M^{-1}$. Lower affinities are generally no longer measurable with common methods such as ELISA and therefore of secondary importance. Especially preferred are lipocalin muteins, which bind the desired target with an affinity of at least $10^6$ $M^{-1}$, corresponding to a dissociation constant of the complex of 1 µM. The binding affinity of a mutein to the desired target can be measured by a multitude of methods such as fluorescence titration, competition ELISA or surface plasmon resonance.

It is clear to the skilled person that complex formation is dependent on many factors such as concentration of the binding partners, the presence of competitors, ionic strength of the buffer system etc. Selection and enrichment is generally performed under conditions allowing the isolation of lipocalin muteins having an affinity constant of at least $10^5$ $M^{-1}$ to the target.

However, the washing and elution steps can be carried out under varying stringency. A selection with respect to the kinetic characteristics is possible as well. For example, the selection can be performed under conditions, which favor complex formation of the target with muteins that show a slow dissociation from the target, or in other words a low $k_{off}$ rate.

A tear lipocalin mutein of the invention may be used for complex formation with a given target. The target may be a non-natural target/ligand. The target (ligand) may be any chemical compound in free or conjugated form which exhibits features of an immunological hapten, a hormone such as steroid hormones or any biopolymer or fragment thereof, for example, a protein or protein domain, a peptide, an oligodeoxynucleotide, a nucleic acid, an oligo- or polysaccharide or conjugates thereof. In a preferred embodiment of the invention the target is a protein. The protein can be any globular soluble protein or a receptor protein, for example, a transmembrane protein involved in cell signaling, a component of the immune systems such as an MHC molecule or cell surface receptor that is indicative of a specific disease. The mutein may also be able to bind only fragments of a protein. For example, a mutein can bind to a domain of a cell surface receptor, when it is part of the receptor anchored in the cell membrane as well as to the same domain in solution, if this domain can be produced as a soluble protein as well. However the invention is by no means limited to muteins that only bind such macromolecular targets. But it is also possible to obtain muteins of tear lipocalin by means of mutagenesis which show specific binding affinity to ligands of low(er) molecular weight such as biotin, fluorescein or digoxigenin.

A tear lipocalin mutein of the invention typically exists as monomeric protein. However, it is also possible that an inventive lipocalin mutein is able to spontaneously dimerise or oligomerise. Although the use of lipocalin muteins that form stable monomers is usually preferred due to the simplified handling of the protein, for example, the use of lipocalin muteins that form stable homodimers or multimers can even be preferred here since such multimers can provide for a (further) increased affinity and/or avidity to a given target. Furthermore, oligomeric forms of the lipocalin mutein may have prolonged serum half-life.

For some applications, it is useful to employ the muteins of the invention in a labeled form. Accordingly, the invention is also directed to lipocalin muteins which are conjugated to a label selected from the group consisting of enzyme labels, radioactive labels, colored labels, fluorescent labels, chromogenic labels, luminescent labels, haptens, digoxigenin, biotin, metal complexes, metals, and colloidal gold. The mutein may also be conjugated to an organic molecule. The term "organic molecule" as used herein preferably denotes an organic molecule comprising at least two carbon atoms, but preferably not more than seven rotatable carbon bonds, having a molecular weight in the range between 100 and 2000 Dalton, preferably 1000 Dalton, and optionally including one or two metal atoms.

In general, it is possible to label the lipocalin mutein with any appropriate chemical substance or enzyme, which directly or indirectly generates a detectable compound or signal in a chemical, physical or enzymatic reaction. An example for a physical reaction is the emission of fluorescence upon irradiation or the emission of X-rays when using a radioactive label. Alkaline phosphatase, horseradish peroxidase or β-galactosidase are examples of enzyme labels which catalyze the formation of chromogenic reaction products. In general, all labels commonly used for antibodies (except those exclusively used with the sugar moiety in the Fc part of immunoglobulins) can also be used for conjugation to the muteins of the present invention. The muteins of the invention may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The lipocalin muteins of the invention may, however, also be conjugated with therapeutically active nucleic acids such as antisense nucleic acid molecules, small interfering RNAs, micro RNAs or ribozymes. Such conjugates can be produced by methods well known in the art.

For several applications of the muteins disclosed herein it may be advantageous to use them in the form of fusion proteins. In preferred embodiments, the inventive lipocalin mutein is fused at its N-terminus or its C-terminus to a protein, a protein domain or a peptide such as a signal sequence and/or an affinity tag.

The fusion partner may confer new characteristics to the inventive lipocalin mutein such as enzymatic activity or binding affinity for other molecules. Examples of suitable fusion proteins are alkaline phosphatase, horseradish peroxidase, gluthation-S-transferase, the albumin-binding domain of protein G, protein A, antibody fragments, oligomerization domains, lipocalin muteins of same or different binding specificity (which results in the formation of "duocalins", cf. Schlehuber, S., and Skerra, A. (2001), *Biol. Chem.* 382, 1335-1342), or toxins. In particular, it may be possible to fuse a lipocalin mutein of the invention with a separate enzyme active site such that both "components" of the resulting fusion protein together act on a given therapeutic target. The binding domain of the lipocalin mutein attaches to the disease-causing target, allowing the enzyme domain to abolish the biological function of the target. If two bispecific lipocalin muteins of the inventions (i.e. each of them has two binding sites) are combined into a "duocalin", a tetravalent molecule is formed. If for example a duocalin is generated from only one mutein having two binding sites that specifically bind biotin, a tetravalent molecule (homodimer) comparable to streptavidin (which is a homotetramer, in which each monomer binds one biotin molecule) can be obtained. Due to expected avidity effects such a mutein might be a useful analytical tool in methods that make use of the detection of biotin groups. A lipocalin mutein that spontaneously forms homodimers or -multimers can, of course, also be used for such a purpose.

Affinity tags such as the STREP-TAG® or STREP-TAG® II (strepavidin tag used for detection or purification of recombinant proteins) (Schmidt, T. G. M. et al. (1996) *J. Mol. Biol.* 255, 753-766), the myc-tag, the FLAG-tag, the His$_6$-tag or the HA-tag or proteins such as glutathione-S-transferase also allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable fusion partners for a lipocalin mutein of the invention as well.

The term "fusion protein" as used herein also comprises lipocalin muteins according to the invention containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences is known in the art. A preferred signal sequence for secretion a polypeptide into the periplasm of *E. coli* is the OmpA-signal sequence.

The present invention also relates to nucleic acid molecules (DNA and RNA) comprising nucleotide sequences coding for muteins as described herein. Since the degeneracy of the genetic code permits substitutions of certain codons by other codons specifying the same amino acid, the invention is not limited to a specific nucleic acid molecule encoding a fusion protein of the invention but includes all nucleic acid molecules comprising nucleotide sequences encoding a functional fusion protein.

In one preferred embodiment of the nucleic acid molecule of invention its sequence is derived from the coding sequence of human tear lipocalin. In other preferred embodiments the nucleic acid is derived from the VEGP protein, VEG protein 2, LCN 1 or ALL 1 protein In another preferred embodiment the nucleic acid sequence encoding a mutein according to the invention comprises mutations at any two or more of the sequence positions in the peptide segments corresponding to the sequence positions 7-14, 43-49, 70-77, and 87-97 of the linear polypeptide sequence of human tear lipocalin with the sequence positions corresponding to the positions 8, 9, 10, 11, 12, 13, 43, 45, 47, 70, 72, 74, 75, 90, 92, 94, and 97 of human tear lipocalin being particularly preferred.

In a further preferred embodiment the nucleic acid sequence encoding a mutein according to the invention comprises mutations at any two or more of the sequence positions in the peptide segments corresponding to the sequence positions 24-36, 53-66, 79-84, and 103-110 of the linear polypeptide sequence of human tear lipocalin.

Also preferred are nucleic acid molecules encoding a mutein of the invention comprising mutations at any two or more of the sequence positions in the peptide segments corresponding to the sequence positions 7-14, 43-49, 70-77, and 87-97 of the linear polypeptide sequence of human tear lipocalin mutations and additional mutations at any two or more of the sequence positions in the peptide segments corresponding to the sequence positions 24-36, 53-66, 79-84, and 103-110 of the linear polypeptide sequence of human tear lipocalin.

The invention as disclosed herein also includes nucleic acid molecules encoding TLPC muteins, which comprise additional mutations outside the segments of experimental mutagenesis. Such mutations are often tolerated or can even prove to be advantageous, for example if they contribute to an improved folding efficiency, protein stability or ligand binding affinity of the mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5'non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention comprises a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be comprised in a vector or any other cloning vehicles, such as plasmids, phagemids, phage, baculovirus, cosmids or artificial chromosomes. In a preferred embodiment, the nucleic acid molecule is comprised in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (reviewed, e.g., in Kay, B. K. et al. (1996) *Phage Display of Peptides and Proteins—A Laboratory Manual*, 1st Ed., Academic Press, New York N.Y.; Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein of the invention, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding lipocalin muteins of the invention, and in particular a cloning vector containing the coding sequence of such a lipocalin mutein can be transformed into a host cell capable of expressing the gene. Transformation can be performed using standard techniques (Sambrook, J. et al. (1989), supra). Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g. HeLa cells or CHO cells) or primary mammalian cells.

The invention also relates to a method for the generation of a mutein according to the invention or a fusion protein thereof, comprising:
(a) subjecting a nucleic acid molecule encoding a tear lipocalin or a homologue thereof, wherein said tear lipocalin or homologue thereof has at least 60% sequence homology with human tear lipocalin, to mutagenesis at two or more different codons, resulting in one or more mutein nucleic acid molecules(s);
(b) expressing the one or more mutein nucleic acid molecule(s) obtained in (a) in a suitable expression system, and
(c) enriching at least one mutein having a detectable binding affinity for a given target by means of selection and/or isolation.

In further embodiments of this method, the nucleic acid molecule can be individually subjected to mutagenesis at two or more different codons (i.e., usually nucleotide triplets) in any one, two, three or all four above-mentioned peptide segments arranged at either end of the β-barrel structure. Accordingly, it is sufficient to exchange only one base in a codon if this exchange results in a change of the encoded amino acid.

In the method of generation a mutein or a fusion protein thereof is obtained starting from the nucleic acid encoding tear lipocalin or a homologue thereof, which is subjected to mutagenesis and introduced into a suitable bacterial or eukaryotic host organism by means of recombinant DNA technology (as already outlined above).

The coding sequence of, for example, human tear lipocalin (Redl, B. et al. (1992) *J. Biol. Chem.* 267, 20282-20287) can serve as a starting point for mutagenesis of the peptide segments selected in the present invention. For the mutagenesis of the amino acids in the N-terminal peptide stretch and the three peptide loops BC, DE, and FG at the end of the β-barrel structure that is located opposite to the natural lipocalin binding pocket as well as the four peptide loops AB, CD, EF, and GH encompassing said binding pocket, the person skilled in the art has at his disposal the various established standard methods for site-directed mutagenesis (Sambrook, J. et al. (1989), supra). A commonly used technique is the introduction of mutations by means of PCR (polymerase chain reaction) using mixtures of synthetic oligonucleotides, which bear a degenerate base composition at the desired sequence positions. The use of nucleotide building blocks with reduced base pair specificity, as for example inosine, is another option for the introduction of mutations into a chosen sequence segment. A further possibility is the so-called triplet-mutagenesis. This method uses mixtures of different nucleotide triplets each of which codes for one amino acid for the incorporation into the coding sequence.

One possible strategy for introducing mutations in the selected regions of the respective polypeptides is based on the use of four oligonucleotides, each of which is partially derived from one of the corresponding sequence segments to be mutated (cf. FIG. 3). When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a lipocalin peptide library. For example, the first oligonucleotide corresponds in its sequence—apart from the mutated positions—to the coding strand for the peptide segment to be mutated at the most N-terminal position of the lipocalin polypeptide. Accordingly, the second oligonucleotide corresponds to the non-coding strand for the second sequence segment following in the polypeptide sequence. The third oligonucleotide corresponds in turn to the coding strand for the corresponding third sequence segment. Finally, the fourth oligonucleotide corresponds to the non-coding strand for the fourth sequence segment. A polymerase chain reaction can be performed with the respective first and second oligonucleotide and separately, if necessary, with the respective third and fourth oligonucleotide.

The amplification products of both of these reactions can be combined by various known methods into a single nucleic acid comprising the sequence from the first to the fourth sequence segments, in which mutations have been introduced at the selected positions. To this end, both of the products can for example be subjected to a new polymerase chain reaction using flanking oligonucleotides as well as one or more mediator nucleic acid molecules, which contribute the sequence between the second and the third sequence segment. This procedure is schematically reproduced in FIG. 3. In the choice of the number and arrangement within the sequence of the oligonucleotides used for the mutagenesis, the person skilled in the art has numerous alternatives at his disposal.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning (Sambrook, J. et al. (1989), supra). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755.

An embodiment of the phage display technique (reviewed in Kay, B. K. et al. (1996), supra; Lowman, H. B. (1997) supra or Rodi, D. J., and Makowski, L. (1999), supra) using temperent M13 phage is given as an example of a selection method according to the invention. However, it is noted that other temperent phage such as f1 or lytic phage such as T7 may be employed as well. For the exemplary selection method, M13 phagemids (cf. also above) are produced which allow the expression of the mutated lipocalin nucleic acid sequence as a fusion protein with a signal sequence at the N-terminus, preferably the OmpA-signal sequence, and with the capsid protein pIII of the phage M13 or fragments thereof capable of being incorporated into the phage capsid at the C-terminus. The C-terminal fragment ΔpIII of the phage capsid protein comprising amino acids 217 to 406 of the wild type sequence is preferably used to produce the fusion proteins. Especially preferred is a C-terminal fragment of pIII, in which the cysteine residue at position 201 is missing or is replaced by another amino acid.

The fusion protein may comprise additional components such as an affinity tag, which allows the immobilization and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

For example, the phagemid vector pTLPC7 (FIG. 4) can be used for the construction of a phage library encoding human tear lipocalin muteins. The inventive nucleic acid molecules coding for the mutated peptide segments are inserted into the vector using the BstXI restriction sites. Recombinant vectors are then transformed into a suitable host strain such as *E. coli* XL1-Blue. The resulting library is subsequently superinfected in liquid culture with an appropriate M13-helper phage in order to produce functional phage. The recombinant phagemid displays the lipocalin mutein on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying a F- or F'-plasmid. During or after infection gene expression of the fusion protein comprised of the lipocalin mutein and the capsid protein pIII can be induced, for example by addition of anhydrotetracycline. The induction conditions are chosen such that a substantial fraction of the phage obtained displays at least one lipocalin mutein on their surface. Various methods are known for isolating the phage, such as precipitation with polyethylene glycol. Isolation typically occurs after an incubation period of 6-8 hours.

The isolated phage are then subjected to a selection process by incubating them with a given target, wherein the target is present in a form allowing at least a temporary immobilization of those phage displaying muteins with the desired binding activity. Several immobilization methods are known in the art. For example, the target can be conjugated with a carrier protein such as serum albumin and be bound via this carrier to a protein-binding surface such as polystyrene. Microtiter plates suitable for ELISA techniques or so-called "immunosticks" are preferred. Alternatively, conjugates of the target can also be implemented with other binding groups such as biotin. The target can then be immobilized on surfaces, which will selectively bind this group, such as microtiter plates or paramagnetic particles coated with avidin or streptavidin.

For example, the phage particles are captured by binding to the respective target immobilized on the surface. Unbound phage particles are subsequently removed by iterative washing. For the elution of bound phage, free target (ligand) molecules can be added to the samples as a competitor. Alternatively, elution can also be achieved by adding proteases or under moderately denaturing conditions, e.g. in the presence of acids, bases, detergents or chaotropic salts. A preferred method is the elution using buffers having pH 2.2, followed by neutralization of the solution. The eluted phage may then be subjected to another selection cycle. Preferably, selection is continued until at least 0.1% of the clones comprise lipocalin muteins with detectable affinity for the respective target. Depending on the complexity of the library employed 2-8 cycles are required to this end.

For the functional analysis of the selected lipocalin muteins, an *E. coli* host strain is infected with the phagemids obtained and phagemid DNA is isolated using standard techniques (Sambrook, J. et al. (1989), supra). The mutated sequence fragment or the entire lipocalin mutein nucleic acid sequence can be sub-cloned in any suitable expression vector. The recombinant lipocalin muteins obtained can be purified from their host organism or from a cell lysate by various methods known in the art such as gel filtration or affinity chromatography.

However, the selection of lipocalin muteins can also be performed using other methods well known in the art. Furthermore, it is possible to combine different procedures. For example, clones selected or at least enriched by phage display can subsequently be subjected to a colony-screening assay in order to directly isolate a particular lipocalin mutein with detectable binding affinity for a given target. Additionally, instead of generating a single phage library comparable methods can be applied in order to optimize a mutein with respect to its affinity or specificity for the desired target by repeated, optionally limited mutagenesis of its coding nucleic acid sequence.

Once a mutein with affinity to a given target have been selected, it is additionally possible to subject such a mutein to further mutagenesis in order to select variants of even higher affinity from the new library thus obtained. The affinity muturation can be achieved by site specific mutation based on rational design or a random mutation One possible approach for affinity maturation is the use of error-prone PCR, which results in point mutations over a selected range of sequence positions of the lipocalin mutein (cf. Example 17). The error prone PCR can be carried out in accordance with any known protocol such as the one described by Zaccolo et al. (1996) *J. Mol. Biol.* 255, 589-603. Other methods of random mutagenesis that are suitable for affinity maturation include random insertion/deletion (RID) mutagenesis as described by Murakami, H et al. (2002) *Nat. Biotechnol.* 20, 76-81 or nonhomologous random recombination (NRR) as described by Bittker, J. A et al. (2002) *Nat. Biotechnol.* 20, 1024-1029. Affinity maturation can also be carried out according to the procedure described in WO 00/75308 or Schlehuber, S. et al. (2000) *J. Mol. Biol.* 297, 1105-1120, where muteins of the bilin-binding protein having high affinity to digoxigenin were obtained.

The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then isolated from this host organism or its culture. It is also possible to produce a protein in vitro, for example by use of an in vitro translation system.

When producing the mutein in vivo a nucleic acid encoding a mutein of the invention is introduced into a suitable bacterial or eukaryotic host organism by means of recombinant DNA technology (as already outlined above). For this purpose, the host cell is first transformed with a cloning vector comprising a nucleic acid molecule encoding a mutein of the invention using established standard methods (Sambrook, J. et al. (1989), supra). The host cell is then cultured under conditions, which allow expression of the heterologous DNA and thus the synthesis of the corresponding polypeptide. Subsequently, the polypeptide is recovered either from the cell or from the cultivation medium. Since many lipocalins comprise intramolecular disulfide bonds, it can be preferred to direct the polypeptide to a cell compartment having an oxidizing redox-milieu using an appropriate signal sequence. Such an oxidizing environment is provided in the periplasm of Gram-negative bacteria such as *E. coli* or in the lumen of the endoplasmatic reticulum of eukaryotic cells and usually favors the correct formation of the disulfide bonds. It is, however, also possible to generate a mutein of the invention in the cytosol of a host cell, preferably *E. coli*. In this case, the polypeptide can, for instance, be produced in form of inclusion bodies, followed by renaturation in vitro. A further option is the use of specific host strains having an oxidizing intracellular milieu, which thus allow the production of the native protein in the cytosol.

However, a mutein of the invention may not necessarily be generated or produced only by use of genetic engineering. Rather, a lipocalin mutein can also be obtained by chemical synthesis such as Merrifield solid phase polypeptide synthesis. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (reviewed, e.g., in Lloyd-Williams, P. et al. (1997) *Chemical Approaches to the Synthesis of Peptides and Proteins*. CRC Press, Boca Raton, Fields, G. B., and Colowick, S. P. (1997) *Solid-Phase Peptide Synthesis*. Academic Press, San Diego, or Bruckdorfer, T. et al. (2004) *Curr. Pharm. Biotechnol.* 5, 29-43).

The invention also relates to a pharmaceutical composition comprising at least one inventive mutein or a fusion protein thereof and a pharmaceutically acceptable excipient.

The lipocalin muteins according to the invention can be administered via any parenteral or non-parenteral (enteral) route that is therapeutically effective for proteinaceous drugs. Parenteral application methods comprise, for example, intracutaneous, subcutaneous, intramuscular or intravenous injection and infusion techniques, e.g. in the form of injection solutions, infusion solutions or tinctures, as well as aerosol installation and inhalation, e.g. in the form of aerosol mixtures, sprays or powders. Non-parenteral delivery modes are, for instance, orally, e.g. in the form of pills, tablets, capsules, solutions or suspensions, or rectally, e.g. in the form of suppositories. The muteins of the invention can be administered systemically or topically in formulations containing conventional non-toxic pharmaceutically acceptable excipients or carriers, additives and vehicles as desired.

In a preferred embodiment of the present invention the pharmaceutical is administered parenterally to a mammal, and in particular to humans, with aerosol installation being one of the most preferable application method, taking advantage of the low molecular weight of the muteins.

Accordingly, the muteins of the present invention can be formulated into compositions using pharmaceutically acceptable ingredients as well as established methods of preparation (Gennaro, A. L. and Gennaro, A. R. (2000) *Remington: The Science and Practice of Pharmacy,* 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatin capsules or suppositories, for example, lactose, talc, stearic acid and its salts, fats, waxes, solid or liquid polyols, natural and hardened oils. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

As is evident from the above disclosure, a mutein of the present invention or a fusion protein or a conjugate thereof can be employed in many applications. In general, such a mutein can be used in all applications antibodies are used, except those with specifically rely on the glycosylation of the Fc part.

A mutein of the invention can also be used for the targeting of a compound to a preselected site. For such a purpose the mutein is contacted with the compound of interest in order to allow complex formation. Then the complex comprising the mutein and the compound of interest are delivered the preselected site. This use is in particular suitable, but not restricted to, for delivering a drug (selectively) to the site such an infected body part or organ which is supposed to be treated with the drug.

Another use of the inventive muteins is the binding/detection of a given target or target molecule, comprising contacting the mutein with a test sample supposed to contain said target, and detecting of the mutein/target complex by a suitable signal. A mutein can also be used for the separation of a given target, comprising contacting the mutein with a sample supposed to contain said target in order to allow complex formation, and separating the mutein/target complex from the sample. In such uses the complex comprising the mutein and the target may be immobilized on any suitable solid phase.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By so doing, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of the invention, which binds, for example, tissue- or tumor-specific cellular surface molecules can be generated. Such a mutein may, for example, be employed in conjugated form or as a fusion protein for "tumor imaging" or directly for cancer therapy.

Another related and preferred use of a mutein described herein is target validation, i.e. the analysis whether a polypeptide assumed to be involved in the development or progress of a disease or disorder is indeed somehow causative of that disease or disorder. This use for validating a protein as a pharmacological drug target takes advantage of the ability of a mutein of the present invention to specifically recognize a surface area of a protein in its native conformation, i.e. to bind to a native epitope. In this respect, it is to be noted that this ability has been reported only for a limited number of recombinant antibodies. However, the use of an inventive mutein for validation of a drug target is not limited to the detection of proteins as targets, but also includes the detection of protein domains, peptides, nucleic acid molecules, organic molecules or metal complexes.

BRIEF DESCRIPTION OF THE DRAWINGS

The invention is further illustrated by the following Figures and Examples, in which:

FIG. 1 shows the polypeptide sequence of mature human tear lipocalin (SWISS-PROT Data Bank Accession Number M90424, 158 amino acids, cf. also Redl B. (2000) *Biochim. Biophys. Acta*, supra). In this respect, it is noted that a human protein that was modified as follows was used in the following examples for the generation of lipocalin muteins. First, the first four N-terminal amino acid residues of the deposited sequence of human tear lipocalin (HHLL) (Residues 1-4 of SEQ ID NO: 58) were deleted. Second, the last two C-terminal amino acid residues (SD) were also deleted. Third, the wild type sequence at sequence positions 5 to 7 (ASD) was changed to GGD. These changes are reflected in the attached sequence listings, in which the amino acids GGD are indicated as first three residues of the used tear lipocalin. The four segments (AB, CD, EF and GH) at the open end of the β2-barrel in which amino acids are exchanged are marked below the sequence of TLPC by double underlining. The segments BC, DE and FG and the N-terminal peptide stretch in which mutations are introduced to create a binding site at the closed end of the β-barrel are marked in bold and single underlining. The sequences positions of TLPC that are mutated in the examples are additionally labeled with asterisks.

FIG. 2 schematically illustrates the characteristic features of the lipocalin fold (according to Flower, D. R. (1996), supra). The eight β-strands of the antiparallel β-sheet which form the β-barrel) are shown as arrows and labeled A to H (a ninth β-strand, designated I which is additionally present in some lipocalins, is also schematically shown). The hydrogen-bonded connection of two strands is indicated by a pair of dotted lines between them. The connecting loops are shown as solid curved lines. The two ends of the β-barrel are topologically distinct. One end has four β-hairpins (loops AB, CD, EF and GH), the opening of the known ligand binding site of the lipocalins is here and called the open end. The other end of the β-barrel has three loops (BC, DE and FG), which together with the N-terminal polypeptide region build the closed end and are used in the present invention to introduce an alternative binding site. The parts which form the three main structurally conserved regions (SCRs) of the fold, SCR1, SCR2 and SCR3, are marked as boxes.

FIG. 3 schematically shows a strategy for the concerted mutagenesis of 17 selected amino acid positions in the modified TLPC by repeated polymerase chain reaction (PCR). For the sequence near the N-terminus and for each of the three peptide loops BC, DE, and FG, respectively, in which the amino acids are to be mutated, an oligodeoxynucleotide was synthesized, (SEQ ID NO: 3, SEQ ID NO: 4, SEQ ID NO: 5, and SEQ ID NO: 6), bearing random nucleotides as indicated in the sequence listing. Due to the composition chosen, from the altogether three possible stop codons only the amber stop codon, TAG, was allowed at the mutated codons, which is translated as glutamine in the E. coli supE strains XL1-blue (Bullock et al. (1987) BioTechniques 5, 376-378) or TG1 (Sambrook et al., supra). For certain applications, for example gene expression in other bacterial strains or organisms, such a nonsense codon can be substituted by a glutamine-encoding codon, e.g., by site-directed mutagenesis. A nucleic acid fragment with 159 base pairs was amplified (PCR No. 1, A) with the respective primers SEQ ID NO: 3 and SEQ ID NO: 4 using the pTLPC6 plasmid-DNA (SEQ ID NO: 2) as a template. In another PCR, a nucleic acid fragment with 123 base pairs was amplified (PCR no. 1, B) with the primers SEQ ID NO: 5 and SEQ ID NO: 6, respectively, also using pTLPC6 as template. The mixture of both PCR products served as a template in another amplification (PCR No. 2) with the two 5'-biotinylated flanking PCR primers, namely SEQ ID NO: 7 and SEQ ID NO: 8, and a mediating primer SEQ ID NO: 9, resulting in the amplification of a DNA fragment of 341 base pairs. This fragment comprising a mixture of all 17 mutated codons was subsequently cloned into the vector pTPLC7 using the two BstXI restriction sites, the special arrangement of which led to two non-compatible overhanging DNA ends enabling a particularly efficient ligation. The ligation efficiency could be improved by purification of the digested PCR-fragment by paramagnetic streptavidin coated beads. The amino acid substitution Glu104Gln as well as the silent mutations in the codon for Ala-3 of the ompA signal sequence, in the codon for Ala21 and His106 were previously accomplished during the construction of pTLPC6 in order to introduce both of the BstX1 restriction sites into the TLPC coding sequence.

FIG. 4 shows a schematic drawing of the vector pTLPC7 encoding a fusion protein comprised of the OmpA signal sequence (OmpA), a modified TLPC with the amino acid substitutions Ala5Asp, Ser6Gly, Asp7Gly, Cys101Ser, and Glu104Gln (for the TLPC cDNA, see Redl et al., supra) and a truncated form of the M13 coat protein pIII, comprising amino acids 217 to 406 (pIII). Gene expression is under the control of the tetracycline promoter/operator (tet$^{p/O}$) system. Transcription is terminated at the lipoprotein transcription terminator ($t_{lpp}$). The vector further comprises an origin of replication (ori), the intergenic region of the filamentous phage fl (fl-IG), the ampicillin resistance gene (bla) coding for □-lactamase and the tetracycline repressor gene (tetR). An amber stop codon, which is partially translated into Gln in SupE amber suppressor host strain, is located between the TLPC coding region and the coding region for the truncated phage coat protein pIII. Both the BstXI-restriction sites used for the cloning of the mutated gene cassette and the restriction sites flanking the structural gene are labeled. The nucleic acid sequence of a XbaI-HindIII segment of pTLPC7 is shown together with the encoded amino acid sequence in the sequence listing as SEQ ID NO: 1 (nucleic acid) and SEQ ID NO: 40 (protein). The vector sequence outside this region is identical with that of pASK75, the complete nucleotide sequence of which is given in the German patent publication DE 44 17 598 A1.

FIG. 5 shows a schematic drawing of the vector pTLPC6. pTLPC6 encodes a fusion protein comprised of the OmpA signal sequence, a modified TLPC according to FIG. 1, and the STREP-TAG® II affinity tag. Otherwise, the vector is identical to pTLPC7. The nucleic acid sequence of a XbaI-HindIII segment of pTLPC6 is shown together with the encoded amino acid sequence in the sequence listing as SEQ ID NO: 2. The vector sequence outside this region is identical with that of pASK75, the complete nucleotide sequence of which is given in the German patent publication DE 44 17 598 A1.

FIG. 6 schematically shows a strategy for the concerted mutagenesis of 17 or 19 selected amino acid positions in the modified TLPC by repeated polymerase chain reaction (PCR). For randomization of loop AB three forward oligodeoxynucleotides were synthesized (SEQ ID NO: 26, SEQ ID NO: 27, and SEQ ID NO: 28), which differs in length coding for a randomized loop AB as well as an extension by two and four amino acids, respectively) and one reverse oligodeoxynucleotide for loop CD (SEQ ID NO: 29). Furthermore a pair of two oligodeoxynucleotides was synthesized (SEQ ID NO: 30, and SEQ ID NO: 31) for the peptide loops EF and GH, respectively. These oligonucleotides are bearing random nucleotides as indicated in the sequence listing in which the amino acids are to be mutated. Three nucleic acid fragments with 142, 148, and 154 base pairs were amplified (PCR No. 1, A) with the respective primers SEQ ID NO: 26, SEQ ID NO: 27, SEQ ID NO: 28, and SEQ ID NO: 29 using the pTLPC12 plasmid-DNA (FIG. 7, SEQ ID NO: 23) as a template. In another PCR, a nucleic acid fragment with 119 base pairs was amplified (PCR No. 1, B) with the primers SEQ ID NO: 30 and SEQ ID NO: 31, respectively, also using pTLPC12 as template. The mixture of PCR fragment B resulting from PCR No. 1B with each of the three PCR fragments A resulting from PCR No. 1A (varying in length of loop AB) served as templates in another amplification (PCR No. 2) employing the two 5'-biotinylated flanking PCR primers given as SEQ ID NO: 33 and SEQ ID NO: 34 together with a mediating primer SEQ ID NO: 32. This PCR resulted in an amplification of DNA fragments consisting of 336, 342, and 348 base pairs in size which comprises nearly the whole structural gene of tear lipocalin with either 17 (for loop AB and loop AB extended by 4 amino acids) or 19 (for loop AB extended by 2 amino acids) mutated codons. The fragments were subsequently cloned into the vector pTPLC12 using the two BstXI restriction sites, the special arrangement of which led to two non-compatible overhanging DNA ends enabling a particularly efficient ligation. The ligation efficiency could be improved by purification of the digested PCR-fragment by paramagnetic streptavidin coated beads. The amino acid substitution Ser14Pro and Lys114Gln as well as the silent mutations in the codon for Met21, Val110, and in the codon for Val116 were previously accomplished during the construction of pTLPC12 in order to introduce both of the BstXI restriction sites into the TLPC coding sequence.

FIG. 7 shows a schematic drawing of the vector pTLPC12 encoding a fusion protein comprised of the OmpA signal sequence (OmpA), a T7 detection tag (T7), a modified TLPC with the amino acid substitutions Ser14Pro, Lys114Gm, Cys101Ser, and Glu104Gln (for the TLPC cDNA, see Redl et al., supra) and a truncated form of the M13 coat protein pIII, comprising amino acids 217 to 406 (pIII). Gene expression is under the control of the tetracycline promoter/operator ($tet^{p/O}$) system. Transcription is terminated at the lipoprotein transcription terminator ($t_{lpp}$). The vector further comprises an origin of replication (ori), the intergenic region of the filamentous phage fl (fl-IG), the ampicillin resistance gene (bla) coding for β-lactamase and the tetracycline repressor gene (tetR). An amber stop codon, which is partially translated into Gin in SupE amber suppressor host strain, is located between the TLPC coding region and the coding region for the truncated phage coat protein pIII. Both the BstXI-restriction sites used for the cloning of the mutated gene cassette and the restriction sites flanking the structural gene are labeled. The nucleic acid sequence of a XbaI-HindIII segment of pTLPC12 is shown together with the encoded amino acid sequence in the sequence listing as SEQ ID NO: 23 (nucleic acid) and SEQ ID NO: 55 (protein). The vector sequence outside this region is identical with that of pASK75, the complete nucleotide sequence of which is given in the German patent publication DE 44 17 598 A1.

FIG. 8 shows a schematic drawing of the expression vector pTLPC8. pTLPC8 codes for a fusion protein of the OmpA signal sequence with a modified tear lipocalin according to (FIG. 4) followed by the T7 detection tag (T7) and the C-terminal STREP-TAG® II. A relevant segment of the nucleic acid sequence of pTLPC8 is reproduced together with the encoded amino acid sequence in the sequence listing as SEQ ID NO: 24. The segment begins with the XbaI restriction site and ends with the HindIII restriction site. The vector elements outside this region are identical with the vector pASK75, the complete nucleotide sequence of which is exhibited in the German patent publication DE 44 17 598 A1.

FIG. 9 shows a graphical representation of the data from Example 6, in which binding measurements with TLPC mutein and the prescribed target rhuVEGF165 as well as the unrelated target BSA were performed by ELISA. Binding of TLPC mutein S69.4 O13 (filled circles) to rhuVEGF165 immobilized on the ELISA plate was compared with the interaction of the muteins with BSA (open circles) as control (also immobilized on the ELISA plate). The TLPC muteins bound rhuVEGF165 in a concentration-dependent manner, whereas no significant binding signals to the unrelated target (open circles) were detectable.

FIG. 10 shows a graphical representation of the data from Example 10, in which binding measurements of the TLPC mutein S76.1 H10 Monomer with the prescribed target hCD22 as well as the unrelated targets hIgG1, HSA and hCD33-Fc were performed by ELISA. Binding of the immobilized TLPC mutein S76.1 H10 Monomer to hCD22 (closed squares) was compared with the interaction of the mutein with hIgG1 (open triangles), HSA (open circles) and hCD33-Fc (open diamonds). The TLPC mutein binds hCD22 in a concentration-dependent manner, whereas no significant binding signals were detectable to the unrelated targets.

FIG. 11 shows a graphical representation of the data from Example 10, in which binding measurements of the TLPC mutein S76.1 H10 Dimer with the prescribed target hCD22 as well as the unrelated targets hIgG1, HSA and hCD33-Fc were performed by ELISA. Binding of the immobilized TLPC mutein S76.1 H10 Dimer to hCD22 (closed circles) was compared with the interaction of the mutein with hIgG1 (open triangles), HSA (open squares) and hCD33-Fc (open diamonds). The TLPC mutein binds hCD22 in a concentration-dependent manner, whereas no significant binding signals were detectable to the unrelated targets.

FIG. 12 shows a graphical representation of the data from Example 14, in which binding measurements with the TLPC mutein S67.7 C6 and the prescribed target CD25 as well as the unrelated targets capture mAb, HSA, FCS and captured human IgG Fc-fragment were performed by ELISA. Binding of the TLPC mutein S67.7 C6 (closed circle) to CD25-Fc (immobilized on the ELISA plate via a capture mAb) was compared with the interaction of the mutein with capture mAb (open circle) as control (also immobilized on the ELISA plate). The TLPC mutein S67.7 C6 binds CD25 in a concentration-dependent manner, whereas no significant binding signal to the unrelated target capture mAb (open symbol) was detectable. A control binding curve is only shown for this unrelated target, but similar results were obtained for the other control targets tested.

FIG. 13 shows a schematic drawing of the mammalian transfection vector CD25-pcDNA 3.1Zeo(+). This vector codes for the complete cDNA sequence of human CD25 according to NCBI ACCESSION NM_000417 [gi: 4557666]. A relevant segment of the nucleic acid sequence of human CD25 is reproduced together with the encoded amino acid sequence in the sequence listing as SEQ ID NO: 10 (nucleic acid) and SEQ ID NO: 42 (protein). The segment begins with a HindIII restriction site and ends with the XhoI restriction site. The vector elements outside this region are identical with those of the vector pcDNA3.1 Zeo(+) (Invitrogen).

FIG. 14 shows the staining of CHO cells expressing human CD25 with fluorescein labeled TLPC mutein S67.7 C6. CHO cells transfected with the expression vector CD25-pcDNA3.1Zeo(+) (CHO-CD25; upper panels) or the parental vector pcDNA3.1Zeo(+) (CHO; lower panels) were incubated with the CD25-specific mutein S67.7 C6 labeled with fluorescein at an equimolar ratio (left panels; histograms with solid lines) or FITC-labeled CD25-specific mAb (right panels; histograms with solid lines). In parallel, these cell lines were incubated with the recombinant wild type TLPC encoded by pTLPC8 labeled with fluorescein at equimolar ratio (left panels; histograms with broken lines) or FITC-labeled IgG1 (right panels; histograms with broken lines), both as controls. Both the CD25-specific mutein S67.7 C6 and the CD25-specific mAb show significant staining of the CHO cell line expressing human CD25 while no significant staining of the mock-transfected CHO cell line occurs. The controls wild type TLPC and IgG1 show no significant binding to both cell lines tested.

FIG. 15 shows a schematic drawing of pTLPC9. This vector codes for a fusion protein of the OmpA signal sequence, a modified tear lipocalin according to FIG. 1, the STREP-TAG® II and an albumin-binding domain (abd) of protein G from *Streptococcus* (Kraulis et al. (1996) FEBS Lett. 378, 190-194). An amber stop codon has been introduced between the Strep-tag® II and the C-terminal albumin binding domain to allow soluble expression of the TLPC mutein without the ABD when employing a non-supressor E. coli strain. A relevant segment of the nucleic acid sequence of pTLPC9 is reproduced together with the encoded amino acid sequence in the sequence listing as SEQ ID NO: 22. The segment begins with an XbaI restriction site and ends with the HindIII restriction site. The vector elements outside this region are identical with those of the vector pASK75, the complete nucleotide sequence of which is exhibited in the German patent publication DE 44 17 598 A1.

FIG. 16 shows a graphical representation of the data from Example 21, in which binding measurements with the monomeric fraction of TLPC mutein F92.8 M1.2 E15 and the prescribed target CD25 as well as the unrelated targets capture mAb, HSA, FCS and captured human IgG Fc-fragment were performed by ELISA. Binding of the monomeric fraction of TLPC mutein F92.8 M1.2 E15 (closed circle) to CD25-Fc (immobilized on the ELISA plate via a capture mAb) was compared with the interaction of the mutein with capture mAb (open circle) as control (also immobilized on the ELISA plate). The monomeric fraction of TLPC mutein F92.8 M1.2 E15 binds CD25 in a concentration-dependent manner, whereas no significant binding signal to the unrelated target capture mAb (open symbol) was detectable. A control binding curve is only shown for this unrelated target, but similar results were obtained for the other control targets tested.

FIG. 17 shows a graphical representation of the data from Example 21, in which binding measurements with the dimeric fraction of TLPC mutein F92.8 M1.2 E15 and the prescribed target CD25 as well as the unrelated targets capture mAb, HSA, FCS and captured human IgG Fc fragment were performed by ELISA. Binding of the dimeric fraction of TLPC mutein F92.8 M1.2 E15 (closed circle) to CD25-Fc (immobilized on the ELISA plate via a capture mAb) was compared with the interaction of the mutein with capture mAb (open circle) as control (also immobilized on the ELISA plate). The dimeric fraction of TLPC mutein F92.8 M1.2 E15 binds CD25 in a concentration-dependent manner, whereas no significant binding signal to the unrelated target capture mAb (open symbol) was detectable. A control binding curve is only shown for this unrelated target, but similar results were obtained for the other control targets tested.

FIG. 18 shows a schematic drawing of the mammalian transfection vector CD154-pcDNA 3.1 Zeo(+). This vector codes for the complete cDNA sequence of human CD 154 according to NCBI ACCESSION BC_074950 [gi: 49902361]. A relevant segment of the nucleic acid sequence of human CD154 is reproduced together with the encoded amino acid sequence in the sequence listing as SEQ ID NO: 11 (nucleic acid) and SEO ID NO: 43 (protein). The segment begins with a XhoI restriction site and ends with the ApaI restriction site. The vector elements outside this region are identical with those of the vector pcDNA3.1Zeo(+) (Invitrogen).

FIG. 19 shows the staining of CHO cells expressing human CD25 with fluorescein labeled TLPC mutein F92.8 M1.2 E15. CHO cells transfected with the expression vector CD25-pcDNA3.1Zeo(+) (CHO-CD25; upper panels) or the expression vector CD154-pcDNA3.1Zeo(+) (CHO-CD154; lower panels) were incubated with the affinity-improved CD25-specific mutein F92.8 M1.2 E15 labeled with fluorescein at a twofold molar ratio (left panels; histograms with solid lines) or FITC-labeled CD25-specific mAb (right panels; histograms with solid lines). In parallel, these cell lines were incubated with the recombinant wild type TLPC encoded by pTLPC8 labeled with fluorescein at twofold molar ratio (left panels; histograms with broken lines) or FITC-labeled IgG1 (right panels; histograms with broken lines), both as controls. Both the affinity-improved CD25-specific mutein F92.8 M1.2 E1S and the CD25-specific mAb show significant staining of the CHO cell line expressing human CD25 while no significant staining of the CHO cell line expressing human CD154 occurs. The controls wild type TLPC and IgG1 show no significant binding to both cell lines tested.

FIG. 20 shows a graphical representation of the data from Example 26, in which binding measurements with the TLPC muteins S99.3 H24, S99.3 C13 and S99.4 F15, respectively, and the prescribed target CD25 as well as the unrelated targets capture mAb, HSA, FCS and captured human IgG Fc-fragment were performed by ELISA. Binding of the TLPC muteins S99.3 H24 (closed circle), S99.3 C13 (closed square) and S99.4 F15 (closed triangle, respectively) to CD25-Fc (immobilized on the ELISA plate via a capture mAb) was compared with the interaction of the respective muteins with capture mAb (open circle, open square and open triangle, respectively) as control (also immobilized on the ELISA plate). The TLPC muteins S99.3 H24, S99.3 C13 and S99.4 F15 bind CD25 in a concentration-dependent manner, whereas no significant binding signal to the unrelated target capture mAb (open symbols) was detectable. Control binding curves are only shown for this unrelated target, but similar results were obtained for the other control targets tested.

FIG. 21 shows a schematic drawing of the expression vector pTLPC14. pTLPC14 codes for a fusion protein of the OmpA signal sequence, a T7 detection tag (T7) with a modified tear lipocalin according to (FIG. 7) followed by the C-terminal STREP-TAG® II. A relevant segment of the nucleic acid sequence of pTLPC14 is reproduced together with the encoded amino acid sequence in the sequence listing as SEQ ID NO: 25. The segment begins with the XbaI restriction site and ends with the HindIII restriction site. The vector elements outside this region are identical with the vector pASK75, the complete nucleotide sequence of which is exhibited in the German patent publication DE 44 17 598 A1.

FIG. 22 shows a graphical representation of the data from Example 30, in which binding measurements of the TLPC monomeric as well as dimeric fraction of mutein S100.1 I08 with the prescribed target hCD33-Fc as well as the unrelated target hCD22 were performed by ELISA. Binding of the TLPC mutein S100.1 I08 to hCD33-Fc (closed circles; closed triangles) was compared with the interaction with hCD22 (open circles; open triangles). The TLPC mutein binds hCD33-Fc in a concentration-dependent manner, whereas no significant binding signals were detectable to the unrelated target.

FIG. 23 shows a graphical representation of the data from Example 30, in which binding measurements of the TLPC mutein S101.2 A20 with the prescribed target hCD33-Fc as well as the unrelated targets hCD22 and hIgG1 were performed by ELISA. Binding of the TLPC mutein S101.2 A20 to hCD33-Fc (closed circles) was compared with the interaction of the mutein with hIgG1 (open circles) and hCD22 (open triangles). The TLPC mutein binds hCD33-Fc in a concentration-dependent manner, whereas no significant binding signals were detectable to the unrelated targets.

FIG. 24 shows a graphical representation of the data from Example 30, in which binding measurements of the monomeric as well as dimeric fraction of the TLPC mutein S101.2 O08 with the prescribed target hCD33-Fc as well as the unrelated targets hCD22 and hIgG1 were performed by ELISA. Binding of the TLPC mutein S101.2 O08 to hCD33-Fc (closed circles; closed squares) was compared with the interaction of the mutein with hIgG1 (open triangles; open diamonds) and hCD22 (open circles; open squares). The TLPC mutein binds hCD33-Fc in a concentration-dependent manner, whereas no significant binding signals were detectable to the unrelated targets.

FIG. 25 shows a sensorgram of binding measurements from example 31 in which the binding signal measured in RU (=response units) is plotted against the time. During injection the TLPC mutein S100.1 I08 associates with the prescribed target hCD33-Fc. After injection the surface is washed with running buffer and the mutein dissociates from its target. Association rate and dissociation rate constants ($k_{on}$ and $k_{off}$) were determined using the BIAevaluation software 3.1.

FIG. 26 shows a sensorgram of binding measurements from example 31 in which the binding signal measured in RU (=response units) is plotted against the time. During injection the TLPC mutein S101.2 A20 associates with the prescribed target hCD33-Fc. After injection the surface is washed with running buffer and the mutein dissociates from its target. Association rate and dissociation rate constants ($k_{on}$ and $k_{off}$) were determined using the BIAevaluation software 3.1.

FIG. 27 shows a sensorgram of binding measurements from example 31 in which the binding signal measured in RU (=response units) is plotted against the time. During injection the TLPC mutein S101.2 O08 associates with the prescribed target hCD33-Fc. After injection the surface is washed with running buffer and the mutein dissociates from its target. Association rate and dissociation rate constants ($k_{on}$ and $k_{off}$) were determined using the BIAevaluation software 3.1.

EXAMPLES

Example 1

Generation of a Library with 10 Billion Independent TLPC Muteins

Unless otherwise indicated, established recombinant genetic methods were used, for example as described in Sambrook et al. (supra).

Figures 1, 2:
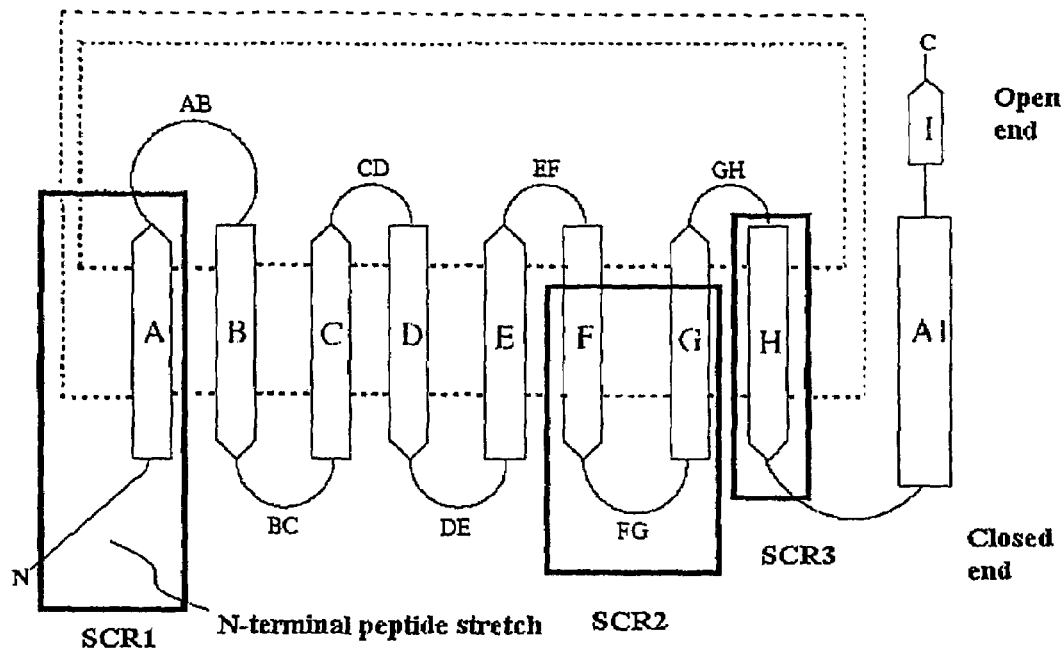
FIG. 1 shows the polypeptide sequence of mature human tear lipocalin (SWISS-PROT Data Bank Accession Number M90424) (SEQ ID NO: 58).
FIG. 2 schematically depicts the structure of the lipocalin fold.
Figure 3:
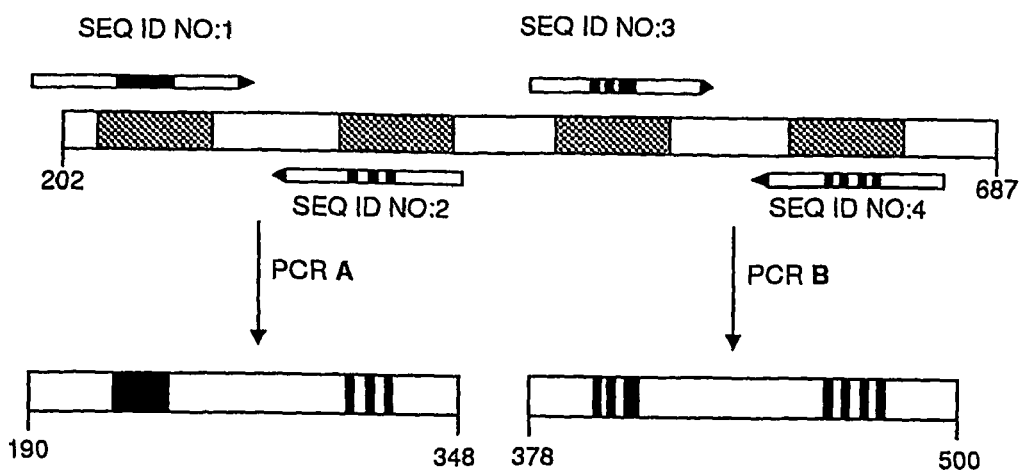
FIG. 3 schematically illustrates the generation of the library of tear lipocalin muteins randomized at the closed end of the β-barrel at the nucleic acid level.
Figure 3:
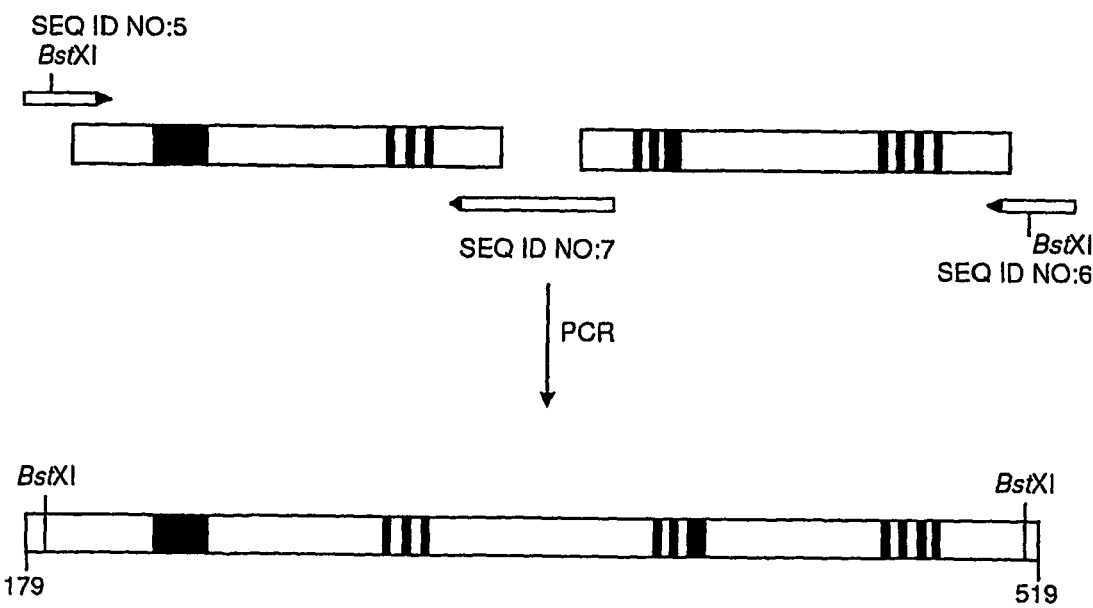
Figure 5:
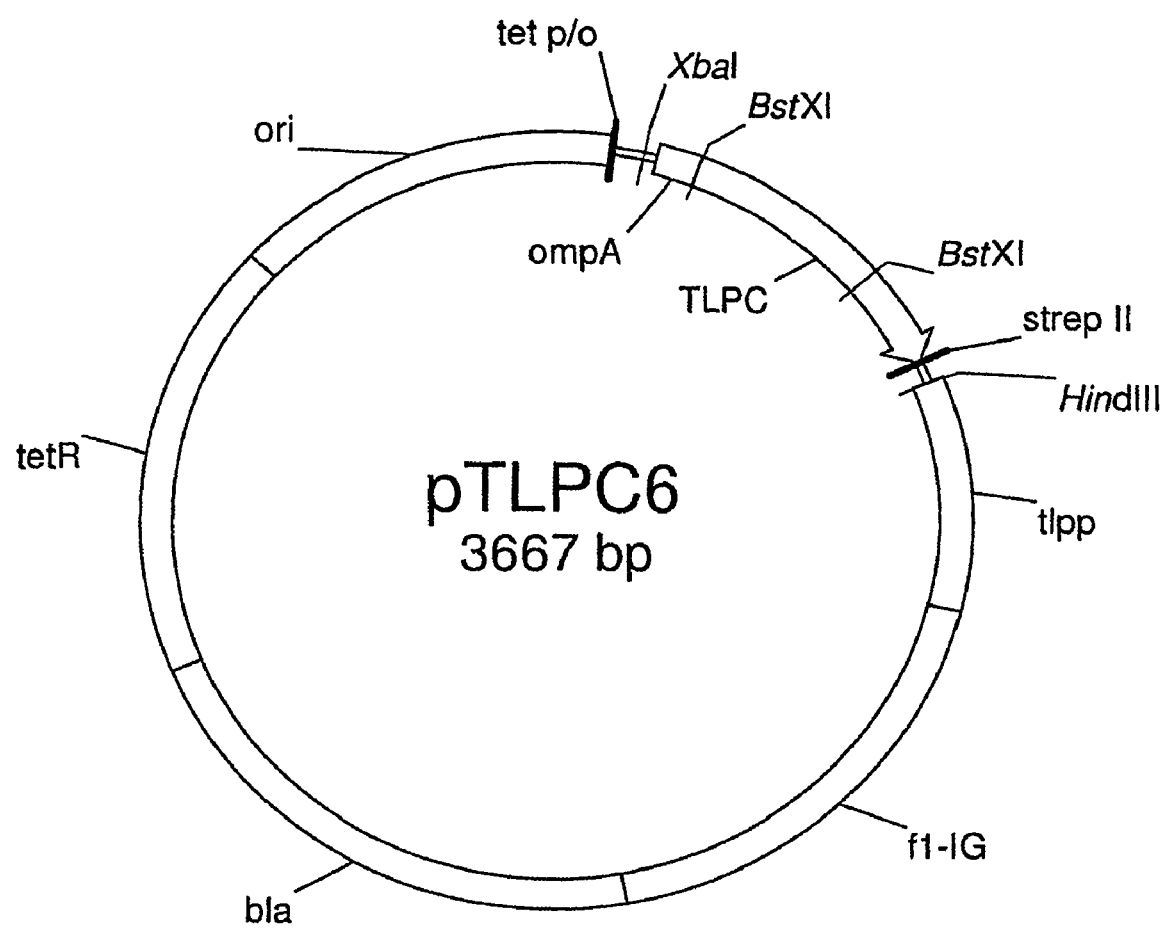
FIG. 5 schematically depicts the phasmid vector pTLPC6.

A random library of TLPC with high complexity was prepared by concerted mutagenesis of in total 17 selected amino acid positions near the N-terminus and in the peptide loops BC, DE, and FG using PCR in multiple steps according to FIG. 3. The PCR reactions were performed in a volume of 100 µl in both of the first amplification steps (PCR No. 1, A and B), wherein 10 ng pTLPC6 plasmid-DNA (FIG. 5, SEQ ID NO: 2) was employed as template together with 50 pmol of each pair of primers (SEQ ID NO: 3 and SEQ ID NO: 4 or SEQ ID NO: 5 and SEQ ID NO: 6, respectively), which were synthesized according to the conventional phosphoramidite method. In addition, the reaction mixture contained 10 µl 10×Taq buffer (100 mM Tris/HCl pH 9.0, 500 mM KCl, 15 mM MgCl$_2$, 1% v/v Triton X-100) and 2 µl dNTP-Mix (10 mM DATP, dCTP, dGTP, dTTP). After bringing to volume with water, 5 U Taq DNA-polymerase (5 U/µl, Promega) were added and 20 cycles of 1 minute at 94° C., 1 minute at 62° C. and 1.5 minutes at 72° C. were carried out in a thermocycler with a heated lid (Eppendorf), followed by an incubation for 5 minutes at 60° C. for final extension. The desired amplification products were isolated by preparative agarose gel electrophoresis from GTQ Agarose (Roth) using the Jetsorb DNA extraction kit (Genomed).

For the subsequent amplification step a 2000 µl mixture was prepared, wherein approximately 1000 fmol of both of these respective fragments were used as templates, in the presence of 1000 pmol of each of the assembly primers SEQ ID NO: 7, SEQ ID NO: 8 and 20 pmol of the mediating primer SEQ ID NO: 9. Both assembly primers had a biotin group at their 5'-ends allowing the purification of the PCR-product after BstXI cleavage via streptavidin-coated paramagnetic beads. Additionally, 200 µl 10×Taq buffer, 40 µl dNTP-Mix (10 mM DATP, dCTP, dGTP, dTTP), 100 u Taq DNA-polymerase (5 U/µl, Promega) and water were added to bring the mixture to the final volume of 2000 µl. The mixture was divided into 100 µl aliquots and PCR was performed with 20 cycles of 1 minute at 94° C., 1 minute at 60° C., 1.5 minutes at 72° C., followed by a subsequent incubation for 5 minutes at 60° C. The PCR product was purified using the E.Z.N.A. Cycle-Pure Kit (PeqLab).

For cloning purposes, this fragment representing the library of TPLC muteins in nucleic acid form was first cut with the restriction enzyme BstXI (Promega) according to the instructions of the manufacturer and then purified by preparative agarose gel electrophoresis as described above, resulting in a double stranded DNA-fragment of 303 nucleotides in size. DNA-fragments not or incompletely digested were removed via their 5'-biotin tags using streptavidin-coated paramagnetic beads (Merck).

Therefore, 200 µl of the commercially available suspension of the paramagnetic particles in a concentration of 10 mg/ml were washed three times with 100 µl TE-buffer. The particles were then drained and mixed with 100 pmol of the DNA-fragment in 100 µl TE-buffer for 15 minutes at room temperature. The paramagnetic particles were collected at the wall of the Eppendorf vessel with the aid of a magnet and the supernatant containing the purified DNA fragment was recovered for further use in the following ligation reaction.

The DNA of the vector pTLPC7 (FIG. 4) was cut with BstXI as described above and the larger of the two resulting fragments (3907 bp) was purified by preparative agarose gel electrophoresis. For the ligation reaction, 5.99 µg (30 pmol) of the PCR fragment and 77.3 µg (30 pmol) of the vector fragment were incubated in the presence of 833 Weiss Units of T4 DNA ligase (Promega) in a total volume of 8330 µl (50 mM Tris/HCl pH 7.8, 10 mM MgCl$_2$, 10 mM DTT, 1 mM ATP, 50 µg/ml BSA) for 24 h at 16° C. The DNA in the ligation mixture was then precipitated by adding 208 µl yeast tRNA (10 mg/ml solution in H$_2$O (Roche)), 8330 µl 5 M ammonium acetate, and 33.3 ml ethanol. Incubation at RT for 1 h was followed by centrifugation (30 minutes, 16000 g, 4° C.). The precipitate washed with 5 ml ethanol (70% v/v, RT), centrifuged (10 minutes, 16000 g, 4° C.), and air dried until the DNA pellet appeared glossy and uncolored. Finally, the DNA was dissolved to a final concentration of 200 µg/ml in a total volume of 416.5 µl water.

The preparation of electrocompetent *E. coli* XL1-Blue (Bullock et al., supra) was carried out according to the methods described by Tung and Chow (*Trends Genet.* 11 (1995), 128-129) and by Hengen (*Trends Biochem. Sci.* 21 (1996), 75-76). 1 l LB-medium was adjusted to an optical density at 600 nm of OD$_{600}$=0.08 by addition of a stationary XL1-Blue overnight culture and was incubated at 140 rpm and 26° C. in a 2 l Erlenmeyer flask. After reaching an OD$_{600}$=0.6, the culture was cooled for 30 minutes on ice and subsequently centrifuged for 15 minutes at 4000 g and 4° C. The cells were washed twice with 500 ml ice-cold 10% w/v glycerol and finally re-suspended in 2 ml of ice-cold GYT-medium (10% w/v glycerol, 0.125% w/v yeast extract, 0.25% w/v tryptone). The cells were then aliquoted (200 µl), shock-frozen in liquid nitrogen and stored at −80° C.

The Micro Pulser system (BioRad) was used in conjunction with cuvettes from the same vendor (electrode separation 2 mm) for electroporation. All steps were carried out at room temperature employing pre-chilled cuvettes at a temperature of −20° C. Each 10 µl of the DNA solution (2 µg) was mixed with 100 µl of the cell suspension, incubated for 1 minute on ice, and transferred to the pre-chilled cuvette. Electroporation was performed (5 ms, 12.5 kV/cm) and the suspension was immediately diluted in 2 ml SOC-medium, followed by incubation for 60 minutes at 37° C. and 140 rpm. Afterwards, the culture was diluted in 412×YT-medium containing 100 µg/ml ampicillin (2 YT/Amp) resulting in an $OD_{550}$ of 0.26. By employing a total of 78.61 µg ligated DNA about $1.0 \times 10^{10}$ transformants were obtained in 42 electroporation runs. The transformants were further used for preparation of phagemids coding for the library of the TLPC muteins as fusion proteins as described in Example 7 of the PCT application WO 03/029471 or Example 1 of the PCT application WO 99/16873.

Example 2

Generation of a Library with 10 Billion Independent TLPC Muteins

Figure 6:
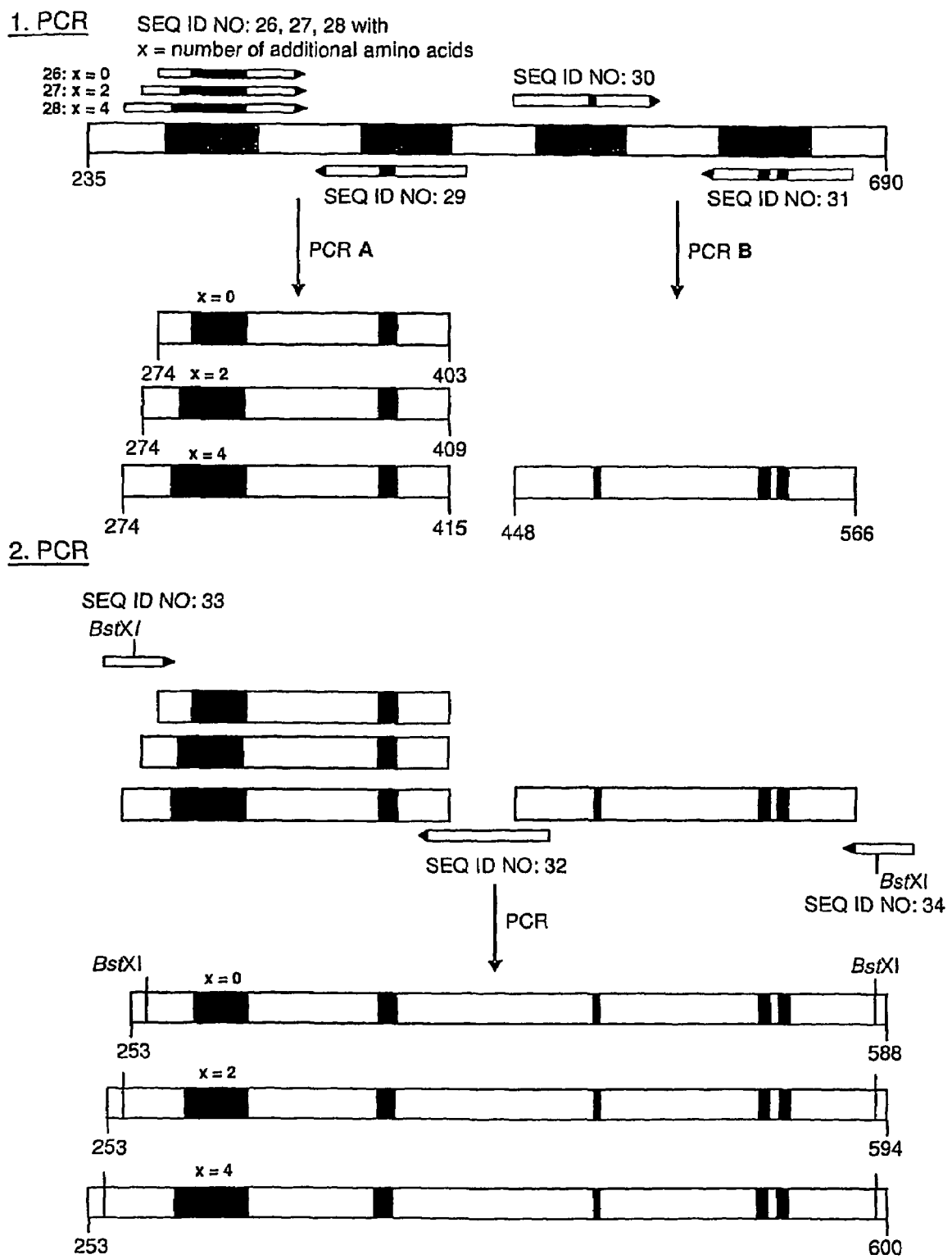
FIG. 6 schematically illustrates the generation of the library of tear lipocalin muteins randomized at the open end of the β-barrel at the nucleic acid level.
Figure 7:
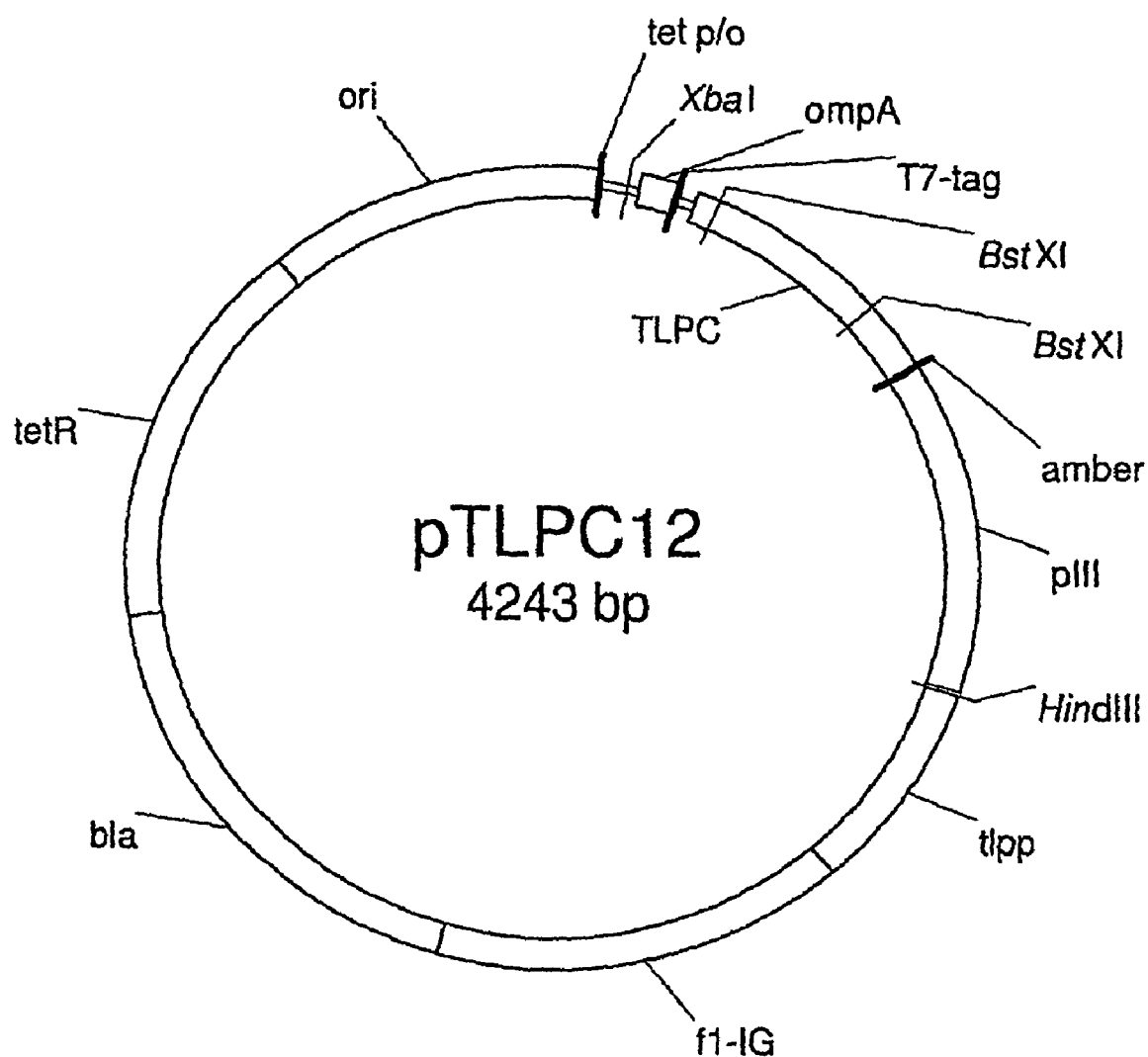
FIG. 7 schematically depicts the phagemid vector pTLPC12.

A second random library of TLPC with high complexity was prepared by concerted mutagenesis of selected amino acid positions in the four peptide loops AB, CD, EF as well as GH encompassing the natural lipocalin binding pocket at the open end of the lipocalin using PCR in multiple steps according to FIG. 6. In loop AB a length variation was introduced by insertion of either two or four amino acids using the same PCR strategy as described in Example 1, but employing two different oligodeoxynucleotides (SEQ ID NO: 27 and SEQ ID NO: 28) for preparation of the fragments from PCR A, comprising six or twelve additional random nucleotides for the insertion of two or four amino acids. In order to stabilize loop AB bearing the four amino acid insertion, the N-terminal and C-terminal anchor positions were fixed by the amino acid substitutions V24W, D25S and M31N, N32S encoded by the oligonucleotide SEQ ID NO: 28. The PCR reactions were performed in the same way as described in Example 1 except that in a first amplification step (PCR No. 1), pTLPC12 plasmid-DNA (FIG. 7, SEQ ID NO: 23) was employed as a template together with the primers SEQ ID NO: 26 and SEQ ID NO: 29 to amplify the unextended loop AB, SEQ ID NO: 27 and SEQ ID NO: 29 for the extension by 2 amino acids, or SEQ ID NO: 28 and SEQ ID NO: 29 for the extension by 4 amino acids. This PCR resulted in an amplification of DNA fragments consisting of 336, 342, and 348 base pairs in size which comprises nearly the whole structural gene of tear lipocalin with either 17 (for loop AB unextended and loop AB extended by 4 amino acids) or 19 (for loop AB extended by 2 amino acids) mutated codons. In PCR No. 1B the oligonucleotides SEQ ID NO: 30 and SEQ ID NO: 31 were employed in order to amplify PCR-fragment B. The desired amplification products were isolated by preparative agarose gel electrophoresis from GTQ Agarose (Roth) using the Wizard SV Gel and PCR Clean-Up System (Promega).

For assembly of the PCR fragments A and B in a subsequent amplification step (PCR No. 2), each of the PCR-fragments A was mixed with PCR-fragment B in a separate 1000 µl mixture, wherein approximately 500 fmol of both of these respective fragments were used as templates, in the presence of 500 pmol of each of the assembly primers SEQ ID NO: 33, SEQ ID NO: 34 and 10 pmol of the mediating primer SEQ ID NO: 32. The PCR products were purified using the Wizard SV Gel and PCR Clean-Up System (Promega).

For cloning purposes, this fragments representing the library of TPLC muteins in nucleic acid form were first cut with the restriction enzyme BstXI (Promega) according to the instructions of the manufacturer and then purified as described above, resulting in double stranded DNA-fragments of 299, 305 and 311 nucleotides in size. DNA-fragments not or incompletely digested were removed via their 5'-biotin tags using streptavidin-coated paramagnetic beads (Merck) as described in Example 1.

For subsequent ligation of the TLPC muteins from above a 3944 fragment was prepared and purified from the DNA of the vector pTLPC12 (FIG. 7) as described in Example 1. For the ligation reaction, 1.97 µg (10 pmol) of each PCR fragment and 84 µg (30 pmol) of the vector fragment were incubated in the presence of 840 Weiss Units of T4 DNA ligase (Promega) in a total volume of 8400 µl (50 mM Tris/HCl pH 7.8, 10 mM $MgCl_2$, 10 mM DTT, 1 mM ATP, 50 µg/ml BSA) for 38 h at 16° C. The DNA in the ligation mixture was then precipitated by adding 210 µl yeast tRNA (10 mg/ml solution in $H_2O$ (Roche)), 8400 µl 5 M ammonium acetate, and 33.6 ml ethanol. Further processing was performed according to Example 1 and finally, the DNA was dissolved to a final concentration of 200 µg/ml in a total volume of 420 µl water.

The preparation and transformation of electrocompetent *E. coli* XL1-Blue (Bullock et al., supra) was carried out according to Example 1. By employing a total of 85.97 µg ligated DNA about $0.6 \times 10^{10}$ transformants were obtained in altogether 42 electroporation runs. The transformants were further used for preparation of phagemids according to the description in Example 7 of the PCT application WO 03/029471 or Example 1 of the PCT application WO 99/16873.

Example 3

Phagemid Presentation and Selection of TLPC Muteins Against VEGF Employing High Binding Polystyrol Multiwell Plates For selection of TLPC muteins, $2 \times 10^{12}$ to $1 \times 10^{13}$ phagemids of the library obtained in Example 1 were used. In brief, the phagemids were centrifuged (21460×g, 4° C., 20 min) and resuspended in 1 ml PBS (4 mM $KH_2PO_4$, 16 mM $Na_2HPO_4$, 115 mM NaCl, pH 7.4) containing 50 mM benzamidine. PBS containing 6% w/v bovine serum albumin (BSA; Roth) and 0.3% Tween 20 was used as blocking buffer. Prior to the incubation with the target protein, phagemids from the library were incubated in bovine serum albumine-blocked polystyrol wells 2 times for 15 minutes for the depletion of phagemids representing multi-reactive or misfolded lipocalin mutein. Recombinant human vascular endothelial growth factor (165 aminoacids, rhuVEGF165) produced in insect cells (R&D Systems) was coated on the polystyrole plates with a concentration of 2.5 µg/ml. After incubation of the blocked phagemids in the coated and blocked wells, adsorbed phagemids were eluted chemically. The adsorbed phagemids were treated with 300 µl 0.1 M glycine/HCl pH 2.2 per respective well for 10 minutes followed by immediate neutralization of the pH of each elution fraction by mixing it with an appropriate amount of 0.5 M Tris. Beginning with the second enrichment cycle, only half of the combined phagemid solutions was used for phagemid amplification. After each cycle of selection the titers of the phagemid input, the eighth wash fraction and the eluted phagemids were determined by spot titration. In brief, serial dilutions of the phagemid solution were mixed with *E. coli* XL1-Blue cells and incubated for 30 min at 37° C. Aliquots of the infected cells were "spottet" on LB/Amp agar plates and incubated over night at 37° C. On the next day, the colonies per spot were counted and the titers of the phagemid solutions (cfu/ml) determined. The phagemid amplification was performed at 22° C.

Four further selection rounds against rhuVEGF165 were carried out in this way employing the preparation of amplified phagemids from the respective previous enrichment cycle with the exception that only about $1 \times 10^{11}$ phagemids were utilized beginning with the second enrichment cycle.

Example 4

Identification of VEGF-Binding TLPC Muteins by Use of a High-Throughput ELISA Screening Method For the analytical production of the TLPC muteins equipped with a C-terminal T7 detection tag (Novagen) followed by a STREP-TAG® II affinity tag and their characterization by high-throughput ELISA screening, the vector pTLPC8 (FIG. 8, SEQ ID NO: 24) was constructed. The gene cassette containing the TLPC scaffold between the two BstXI cleavage sites was subcloned from the vector pTLPC7 (FIG. 4, SEQ ID NO: 1) into pTLPC8.

For this purpose the plasmid DNA was isolated from the mixture of the *E. coli* clones obtained by infection with the phagemids from Example 3 eluted as a result of the last selection cycle, using the Plasmid Miniprep Spin kit (Genomed). The DNA was cut with the restriction enzyme BstXI and the smaller of the two fragments was purified by preparative agarose-gel electrophoresis. The DNA of the vector pTLPC8 was likewise cut with BstXI and the larger of the two fragments (3397 bp) was isolated in the same way.

For the ligation, each 50 fmol of the two DNA-fragments were mixed with 3 Weiss Units T4 DNA ligase (Promega) in a total volume of 20 µl (30 mM Tris/HCl pH 7.8, 10 mM MgCl$_2$, 10 mM DTT, 1 mM ATP), followed by incubation for 2 h at 22° C. *E. coli* TG1-F (*E. coli* K12 TG1, which had lost its episome) was transformed with 5 µl of this ligation mixture according to the CaCl$_2$-method (Sambrook et al., supra) and plated on LB/Amp agar plates (diameter: 14 cm).

Single *E. coli* colonies obtained after the transformation harbouring the respective TLPC plasmids coding for the TLPC muteins were picked from these agar plates into 70 µl per well 2×YT/Amp in flat bottom 384 well plates (Greiner) by means of an automated colony picker (Genetix) and grown overnight at 37° C. at 700 rpm on a benchtop shaker (Bühler) in a humidified incubator (MMM Medcenter) at 60% relative humidity (rH). The cultures were diluted 1:100 into 100 µl 2×YT/Amp in round bottom 96 well plates (Nunc) by means of a 96 pin replicating head (Genetix) and grown for about 1 h at 37° C. and 60% rH, followed by an incubation for 3 h at 22° C. and 60% rH, both at 700 rpm, until the OD$_{550}$ reached approximately 0.6. The 384 well plates were kept as "master" plates at −80° C. after adding 25 µl 60% v/v glycerol to each well.

Recombinant TLPC muteins were produced in the 96 well plates by adding 20 µl per well of 1.2 µg/ml anhydrotetracyclin in 2×YT (obtained by diluting a 2 mg/ml stock solution 1:1667 in 2×YT; final concentration 0.2 µg/ml) to the bacterial cultures and incubation overnight at 22° C. and 700 rpm at 60% rH. Afterwards, 40 µl of lysis buffer (400 mM Na-borate, pH 8.0, 320 mM NaCl, 4 mM EDTA, 0.3% w/v lysozyme) was added to each well and the plate was incubated for 1 h at 22° C. and 700 rpm at 60% rH. To minimize non-specific binding interactions in the subsequent ELISA experiment, obtained crude cell extracts were supplemented with 40 µl/well PBS containing 10% w/v BSA and 0.05% v/v Tween 20 (final concentration 2% w/v BSA) for 1 h at 22° C. and 700 rpm at 60% rH.

For complex formation between the TLPC muteins and the immobilized proteins, the wells were incubated with 10 µl of the cell extract from above for 1 hour at room temperature. Subsequently, plates were washed again five times and 10 µl of an anti-T7 monoclonal antibody-HRP-conjugate (Amersham), diluted 1:5000 in PBST/0.05 containing 0.5% w/v non-fat dry milk powder (Vitalia), was added to each well and incubated for 1 hour at room temperature. Plates were again washed five times and 10 µl of the fluorogenic HRP-substrate QUANTABLU™ (Fluorogenic peroxidase substrate used for peroxidase detection) (Pierce) was added to detect bound TPLC muteins by means of the attached anti-T7 monoclonal antibody-HRP-conjugate. After 45 minutes at room temperature fluorescence was excited at a wavelength of 320 nm (±12.5 nm) and measured at 430 nm (±17.5 nm) in a GENios-Plus plate reader (Tecan).

For complex formation between the TLPC muteins and the immobilized proteins, the wells were incubated with 10 µl of the cell extract from above for 1 hour at room temperature. Subsequently, plates were washed again five times and 10 µl of an anti-T7 monoclonal antibody-HRP-conjugate (Amersham), diluted 1:5000 in PBST/0.05 containing 0.5% w/v non-fat dry milk powder (Vitalia), was added to each well and incubated for 1 hour at room temperature. Plates were again washed five times and 10 µl of the fluorogenic HRP-substrate QuantaBlu™ (Pierce) was added to detect bound TPLC muteins by means of the attached anti-T7 monoclonal antibody-HRP-conjugate. After 45 minutes at room temperature fluorescence was excited at a wavelength of 320 nm (±12.5 nm) and measured at 430 nm (±17.5 nm) in a GENiosPlus plate reader (Tecan).

A selection of 183 TLPC muteins showed significantly higher binding signals on the prescribed target protein (rhuVEGF165) compared to the unrelated control protein (HSA) and were subsequently subjected to a secondary high-throughput ELISA screening experiment. Therefore, these clones were transferred from the 384 well master plates described above onto LB/Amp agar, and grown overnight at 37° C. 100 µl 2×YT/Amp in round bottom 96 well plates (Nunc) was inoculated with single colonies from these agar plates and grown overnight at 37° C. at 700 rpm and 60% rH. The cultures were diluted 1:100 into 100 µl 2×YT/Amp in round bottom 96 well plates (Nunc) and production of recombinant TLPC muteins as well as preparation of the bacterial lysates was performed as described above.

For the detection of target-specificity of the TLPC muteins, wells of black Fluotrac 600 ELISA plates (Greiner; 384 well) were coated overnight at 4° C. with 20 µl of a solution of rhuVEGF165 (insect cells, 1 µg/ml), or, as controls rhu-VEGF165 produced in *Escherichia coli* (ReliaTech GmbH, 1 µg/ml), recombinant mouse VEGF (rmVEGF164) produced in insect cells (ReliaTech GmbH, 1 µg/ml), HSA, 3% w/v non-fat skimmed milk powder and StrepTactin (IBA, 10 µg/ml) as well as a conjugate of RNaseA (Fluka, 10 µg/ml) and digoxigenin in PBS.

This conjugate was prepared by reacting RNaseA at a twofold molar ratio of digoxigenin-3-O-methyl-carbonyl-ε-amidocaproic acid-N-hydroxy-succinimide ester (DIG-NHS; Roche) according to the instructions of the manufacturer. Excess reactant was removed from the RNaseA-conjugate by means of size exclusion chromatography using a HiTrap column (Amersham) according to the instructions of the manufacturer employing PBS as running buffer.

After overnight incubation, the plates were washed as described above and blocked by the addition of 100 µl/well PBST/0.05 containing 2% w/v BSA at the conditions described above, followed again by washing of the plates. 10 µl of the blocked bacterial lysates of the selected TLPC muteins mentioned above were transferred to each of the wells coated with either rhuVEGF165 or the control proteins and incubated for 1 h at ambient temperature. Bound TPLC muteins were detected with anti-T7 monoclonal antibody-HRP-conjugate and the fluorogenic HRP-substrate QUANT-ABLU™ as described above.

A selection of 36 TLPC muteins were confirmed on rhuVEGF165 (insect cells) and additionally showed high signals on rhuVEGF165 (E. coli) and rmVEGF164 (insect cells), but did not show binding on unrelated control proteins (HSA or milk powder).

TLPC muteins with the highest binding signals on the prescribed target rhuVEGF165 versus the control proteins were selected for sequence analysis. Therefore, 4 ml LB/Amp were inoculated with 40 µl of the glycerol stock from the respective well of the 384 well master plate and cultured for subsequent isolation of the plasmid DNA as described at the beginning of this example. The DNA sequence of the TLPC gene cassette was elucidated by using the oligodeoxynucleotide SEQ ID NO: 37 as primer on an automated Genetic Analyzer system (Applied Biosystems) according to the instructions of the manufacturer employing the Big Dye Terminator Cycle Sequencing Kit (Applied Biosystems).

Six unique sequences of six sequenced clones carried a functional insert. The one with the best binding values was named S69.4 O13. The nucleotide sequence of this clone was translated into the amino acid sequence (SEQ ID NO: 12 (nucleic acid) and SEQ ID NO: 44 (protein) in the sequence listing) and those amino acids deviating from the modified TLPC encoded by pTLPC8 and the wild-type Tlpc, respectively, are given in Table 1. The clone S69.4 O13 was chosen for the determination of its binding affinity for rhuVEGF 165 as described in Example 6.

TABLE 1

Sequence characteristics of anti-rhuVEGF165 TLPC muteins

| Pos Numbering according to wild-type Tlpc | Pos (Numbering according to the experimentally used truncated Tlpc | TLPC (4001) | S69.4 O13 |
|---|---|---|---|
| 8 | 4 | Glu | Gly |
| 9 | 5 | Glu | Ile |
| 10 | 6 | Ile | Arg |
| 11 | 7 | Gln | Arg |
| 12 | 8 | Asp | Ser |
| 13 | 9 | Val | Met |
| 43 | 39 | Thr | Leu |
| 45 | 41 | Glu | Lys |
| 47 | 43 | Gly | His |
| 69 | 65° | Glu | Gly |
| 70 | 66 | Lys | Arg |
| 72 | 68 | Asp | Lys |
| 74 | 70 | Pro | Arg |
| 75 | 71 | Gly | Lys |
| 90 | 86 | Arg | Pro |
| 92 | 88 | His | Ala |
| 94 | 90 | Lys | Arg |
| 97 | 93 | Tyr | Val |

°This amino acid substitution arose from accidental mutation outside the randomized positions.

Example 5

Production of the TLPC Mutein

For the preparative production of the mutein S69.4 O13 described in Example 4, the E. coli K12 strain JM83 harbouring the expression vector pTLPC8 (FIG. 8, SEQ D NO: 24) encoding this mutein was used for the periplasmatic production via shake flask expression in an appropriate culture volume of LB-Ampicillin medium according to the protocol described in Schlehuber, S. et al. (J. Mol. Biol. (2000), 297, 1105-1120).

When larger amounts of material were needed, the E. coli K12 strain W3110 harbouring the expression vector pTLPC8 encoding this mutein was used for the periplasmatic production via fermenter cultivation in a 0.75 l or 10 l bioreactor based on the protocol described in Schiweck, W., and Skerra, A. (Proteins (1995) 23, 561-565). Fermentation was carried out at 25° C. The oxygen concentration was maintained at 30% saturation. In a 0.75 l bioreactor, oxygen saturation was kept at 30% via controlling the stirrer speed up to 1500 rpm. In a 10 l reactor, stirrer speed was kept at 480 rpm while supply of air and pure oxygen was regulated automatically. In fed batch phase 50% w/v Glucose was supplied stepwise starting with 17.5 ml/h up to 50 ml/h at OD=22.5.

The mutein was purified from the periplasmic fraction in a single step chromatographic protocol with Strep-Tactin Superflow (IBA) using a column of appropriate bed volume and suitable equipment according to the manufacturers' recommendations.

Gel filtration was carried out with Superdex 75 material (Amersham Pharmacia Biotech) using a column of appropriate bed volume and suitable equipment according to the manufacturers' recommendations. The monomeric fractions were pooled and used for the further characterizations steps.

Example 6

Measurement of the Affinity of the TLPC Muteins for VEGF in ELISA

The affinity of the TLPC muteins for VEGF was measured as follows. In brief, a dilution series of the mutein S69.4 O13 obtained as described in Example 5 was tested in an ELISA assay for binding to rhuVEGF165 and the control protein BSA.

For this purpose, the wells of a black Fluotrac 600 microtiter plate (Greiner; 384 well) were coated with 1 µg/ml rhuVEGF165(insect cells) and 10 µg/ml BSA (Roth) O/N at 4° C. and blocked with 2% w/v BSA in PBST/0.1. After a washing step, a subsequent blocking step with 3% w/v milk powder in PBST and another washing step, a dilution series of the mutein S69.4 O13 in PBST covering an appropriate concentration range was incubated for 1 h at RT in the coated and blocked wells. Bound mutein was subsequently detected via anti-T7 monoclonal antibody-HRP-conjugate and the fluorogenic HRP-substrate QUANTABLU® as described above. After an appropriate incubation time at room temperature, fluorescence was excited at a wavelength of 320 nm (±12.5 nm) and measured at 430 nm (±17.5 nm) in a GENiosPlus plate reader.

The curve was fitted by non-linear least squares regression with the help of the computer program Kaleidagraph (Synergy software) according to the equation $[P \cdot L] = ([P]_t [L]_t) / (K_D + [P]_t)$. Thereby $[P]_t$ is the total concentration of immobilized target (in relative fluorescence units), $[L]_t$ is the concentration of the applied TLPC mutein, respectively, $[P \cdot L]$ is the concentration of the formed complex (in relative fluorescence units, rFU), and $K_D$ is the apparent dissociation constant.

Figure 9:
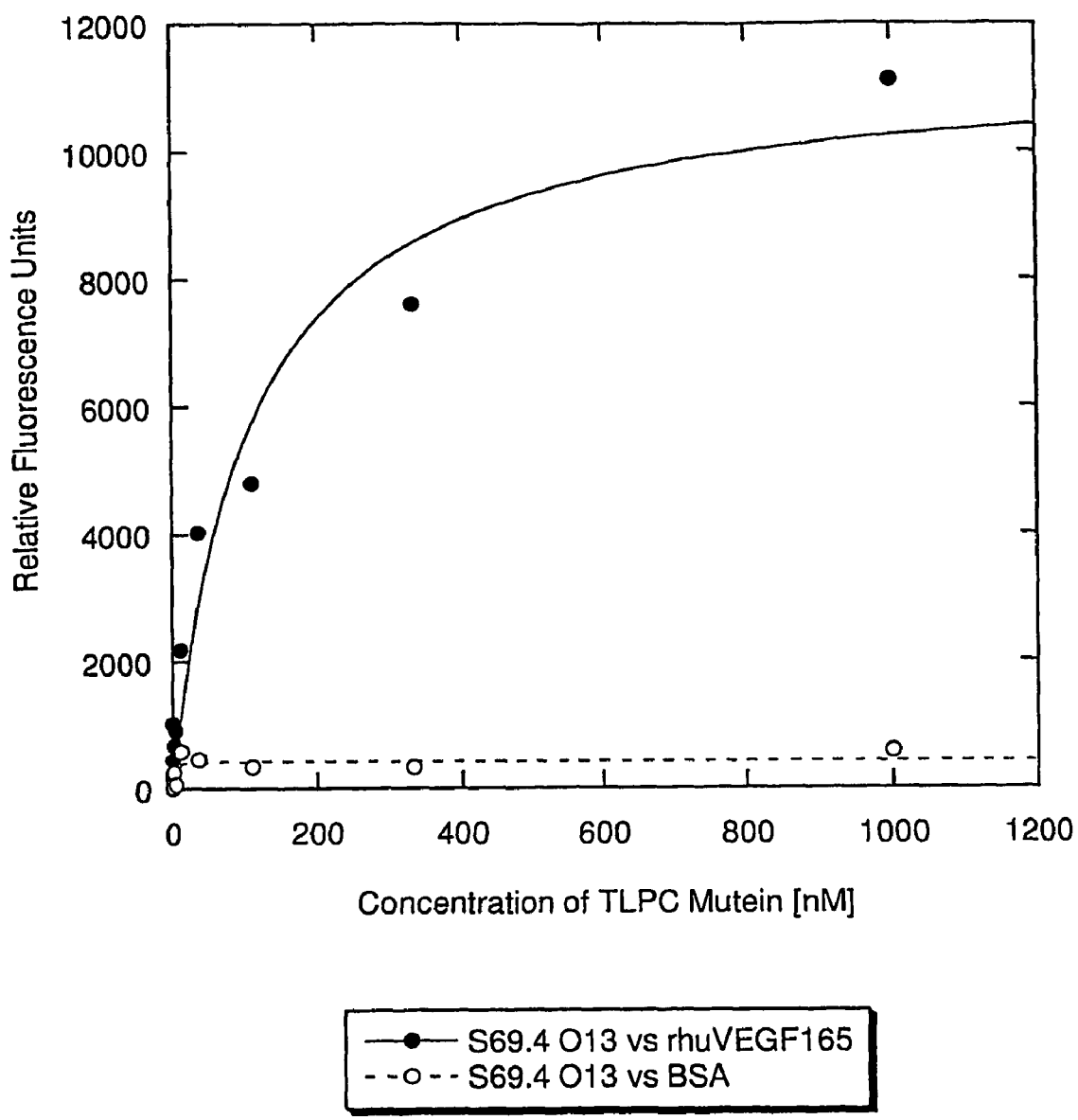
FIG. 9 depicts the binding of the TLPC mutein S69.4 O13 to rhuVEGF165 in an ELISA.

The resulting binding curves versus rhuVEGF165 and BSA are depicted in FIG. 9. The values obtained for the apparent dissociation constants of the complex between the TLPC mutein S69.4 O13 and the prescribed target protein rhuVEGF165 were identified as 109±34 nM (Table 2). No measurable binding activity was obtained for the control protein BSA.

TABLE 2

Affinity binding constants of the TLPC mutein and rhuVEGF165

| TLPC mutein | $K_D$[nM] rhuVEGF165 | $K_D$[nM]BSA |
|---|---|---|
| VEGF S69.4-O13 | 109 ± 34 | —* |

*No detectable binding activity

Example 7

Phagemid Presentation and Selection of TPLC Muteins Against the Extracellular Domain of Human hCD22 Employing Polystyrol Multiwell Plates For the selection of TLPC muteins the phagemid library from example 1 was employed. The selection of TLPC muteins was performed as described in Example 3. The deviations from the protocol are described in the following: Prior to incubation with the target protein phagemids from the library were incubated in BSA-blocked polystyrol wells 2 times for 15 minutes each for the depletion of phagemids presenting multi-reactive or misfolded lipcalin muteins. The extracellular domain of hCD22 (Peprotech EC LTD, UK) was coated on polystyrole plates with a concentration of 5 µg/ml. In the first elution step adsorbed phagemids were treated with 300 µl 0.1 M glycine/HCl pH 2.2 per respective well for 10 minutes followed by immediate neutralization of the pH of each elution fraction by the addition of an appropriate amount of 0.5 M Tris. The basic elution step was performed with 300 µL 70 mM Triethylamin per respective well for 10 minutes followed by immediate neutralization of the pH of each elution fraction by the addition of an appropriate amount of 1M Tris/HCl, pH 7.4. As a final elution step 300 µl exponentially growing XL1 blue ($OD_{550}$ about 0.5) were transferred in each well and incubated for 30 minutes at 37° C. Beginning with the second enrichment cycle, only the half of the combined phagemid solutions was used for phagemid amplification as described in Example 3. For the determination of the phagemid input and the number of eluted phagemids a spot-titration was performed after each cycle of selection from the phagemid used for panning, the $8^{th}$ wash fraction and the eluted phagemids according to Example 3.

Three further selection rounds against hCD22 were carried out in this way employing the preparation of amplified phagemids from the respective previous enrichment cycle with the exception that only about $1 \times 10^{11}$ phagemids were utilized beginning with the second enrichment cycle.

Example 8

Figure 8:
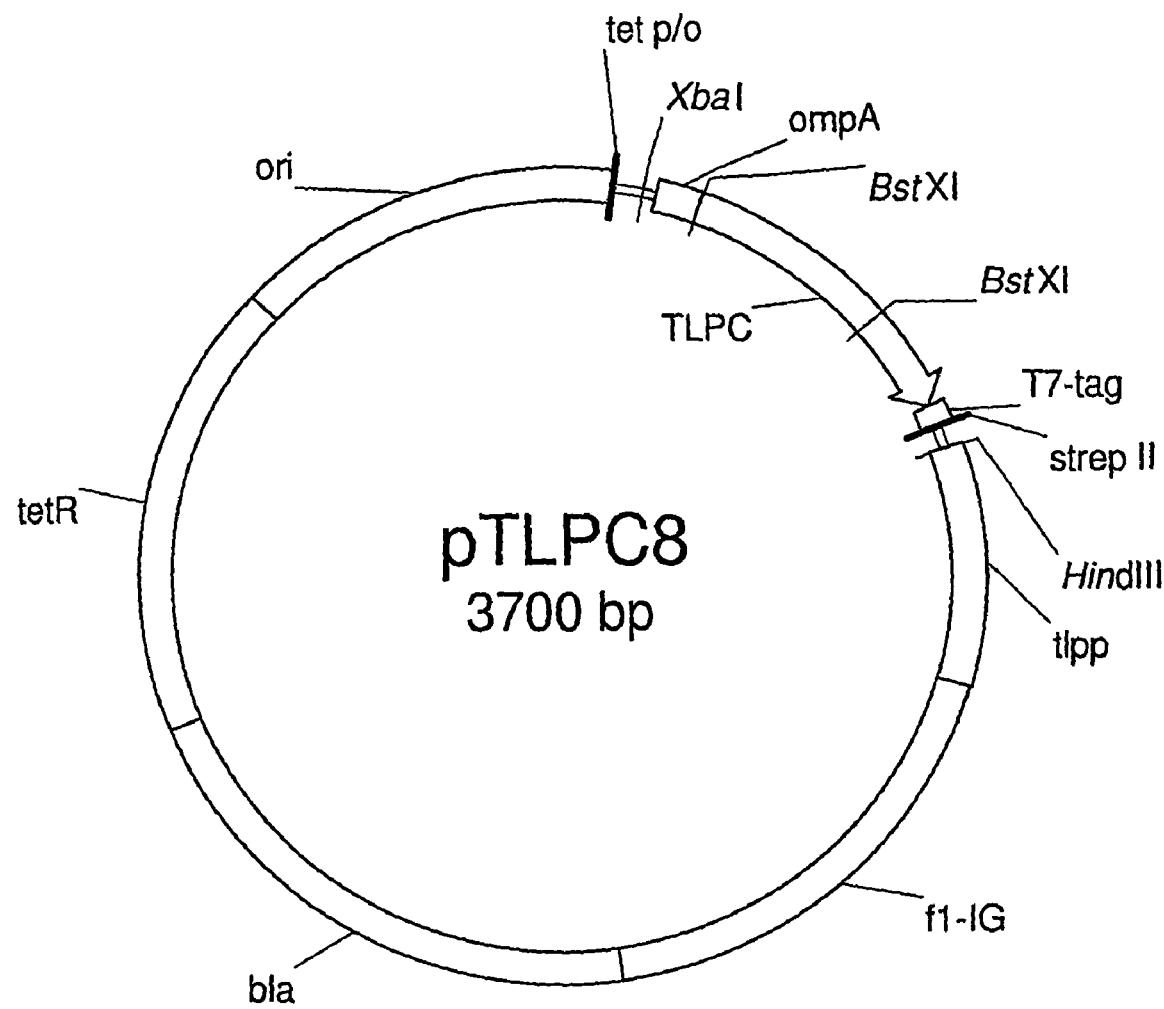
FIG. 8 shows a schematic drawing of the expression vector pTLPC8.

Identification of hCD22-Binding TLPC Muteins by Use of a High-Throughput ELISA Screening Method For the analytical production of the hCD22-binding TLPC muteins equipped with an C-terminal T7 detection tag (Novagen) as well as a STREP-TAG® II affinity tag and their characterization by high-throughput ELISA screening, the gene cassette containing the TLPC between the two BstXI cleavage sites was subcloned from the vector pTLPC7 (FIG. 4) into the vector pTLPC8 (FIG. 8). The hCD22-binding TLPC muteins were identified by a high-throughput ELISA screening method described in Example 4. TLPC muteins that bound hCD22 specifically in the primary screening were selected for more detailed binding analysis in a secondary high-thoughput ELISA screening experiment as described in Example 4 as well.

For the detection of target-specificity of the TLPC muteins, wells of black Fluotrac 600 ELISA plates (Greiner; 384 well) were coated overnight at 4 C with 20 µl of a solution of hCD22 (5 µg/ml, Peprotech) or, as a control, with hCD33-Fc (1 µg/ml, R&D Research), hIgG1 (10 µg/ml, Jackson ImmunoResearch), streptactin (10 µg/ml, IBA), human serum albumin (HSA, 10 µg/ml, Sigma) as well as a conjugate of RNase A (10 µg/ml; RNase from Fluka) with digoxin.

All tested TLPC muteins specifically bound hCD22 specific and the nucleotide sequence of their TLPC gene cassette was determined using the oligodeoxynucleotide SEQ ID NO: 37 as a primer on an automated Genetic Analyzer system (Applied Biosystems) according to the instructions of the manufacturer employing the Big Dye Terminator Cycle Sequencing Kit (Applied Biosystems). All sequenced clones exhibited the same sequence as the clone S76.1 H10. The nucleotide sequence of this clone, S76.1 H10, was translated into the amino acid sequence and those amino acids deviating from the modified TLPC encoded by TLPC 8 (FIG. 8) are given in Table 3. The nucleotide sequence of the clone S76.1 H10 is also given as SEQ ID NO: 13 (encoded protein sequence disclosed as SEQ ID NO: 45).

TABLE 3

Sequence characteristics of selected anti-hCD22 mutein

| Pos Numbering according to wild-type Tlpc | Pos. Numbering according to the experimentally used truncated Tlpc | TLPC | S76.1-H10 |
|---|---|---|---|
| 8 | 4 | Glu | Arg |
| 9 | 5 | Glu | Trp |
| 10 | 6 | Ile | Arg |
| 11 | 7 | Gln | Val |
| 12 | 8 | Asp | Cys |
| 13 | 9 | Val | Trp |
| 43 | 39 | Thr | Gln |
| 45 | 41 | Glu | Asp |
| 47 | 43 | Gly | Lys |
| 70 | 66 | Lys | Leu |
| 72 | 68 | Asp | Asn |
| 74 | 70 | Pro | Gly |
| 75 | 71 | Gly | Val |
| 90 | 86 | Arg | Pro |
| 92 | 88 | His | Arg |
| 94 | 90 | Lys | Ser |
| 97 | 93 | Tyr | Phe |

Example 9

Production of the TLPC Muteins

For the preparative production of the mutein S76.1 H10, obtained from Example 8, the mutagenized coding region between the two BstXI cleavage sites was subcloned from the vector pTLPC7 (FIG. 4) on the expression plasmid pTLPC8 (FIG. 8). The obtained plasmid thus encoded a fusion protein of the mutein with the OmpA signal sequence and the T7-tag as well as the STREP-TAG® II at the C-terminus.

Single colonies of *E. coli*-JM83 and *E. coli*-W3110, respectively, were transformed with the plasmid pTLPC8 coding for the TLPC mutein S76.1 H10. The shaker flask expression, the 1 liter fermentation, the SA-chromatography and the size exclusion chromatography was performed as described in Example 5. It was found, that the mutein S76.1 H10 eluted from the size exclusion chromatography (SEC) in two distinct peaks, containing monomeric and dimeric protein, respectively. The binding affinity of both protein fractions was determined in an ELISA.

Example 10

Measurement of the Affinity of the TLPC Muteins in ELISA

A dilution series of the mutein S76.1 H10, obtained as described in Example 9, was tested in an ELISA assay for binding to direct coated hCD22 and the control proteins hCD33-Fc, HAS, and hIgG1.

For this purpose, the wells of black Fluotrac 600 ELISA plates (Greiner; 384 well) were coated with 20 µl of hCD22 (5 µg/ml, Peprotech) or control proteins hCD33-Fc (1 µg/ml, R&D Research), HSA (10 µg/ml, Sigma), hIgG1 (10 µg/ml, Jackson ImmunoResearch) O/N at 4° C.

After another washing step, a dilution series of the mutein S76.1 H 10, obtained in Example 9, in PBST covering an appropriate concentration rage was added to the coated hCD22 and the control proteins hCD33-Fc, HSA and hIgG1 and incubated for 1 h at RT. Bound mutein was subsequently detected via Streptactin-HRP conjugate (IBA) and the fluorogenic HRP-substrate QUANTABLU™ (PIERCE) according to the respective manufacturers' recommendations. After an appropriate incubation time at room temperature, fluorescence was excited at a wavelength of 320 nm (±12.5 nm) and measured at 430 nm (±17.5 nm) in a GENiosPlus plate reader.

The curve was fitted by non-linear least squares regression with the help of the computer program Kaleidagraph (Synergy software) as described in Example 6.

Figure 10:
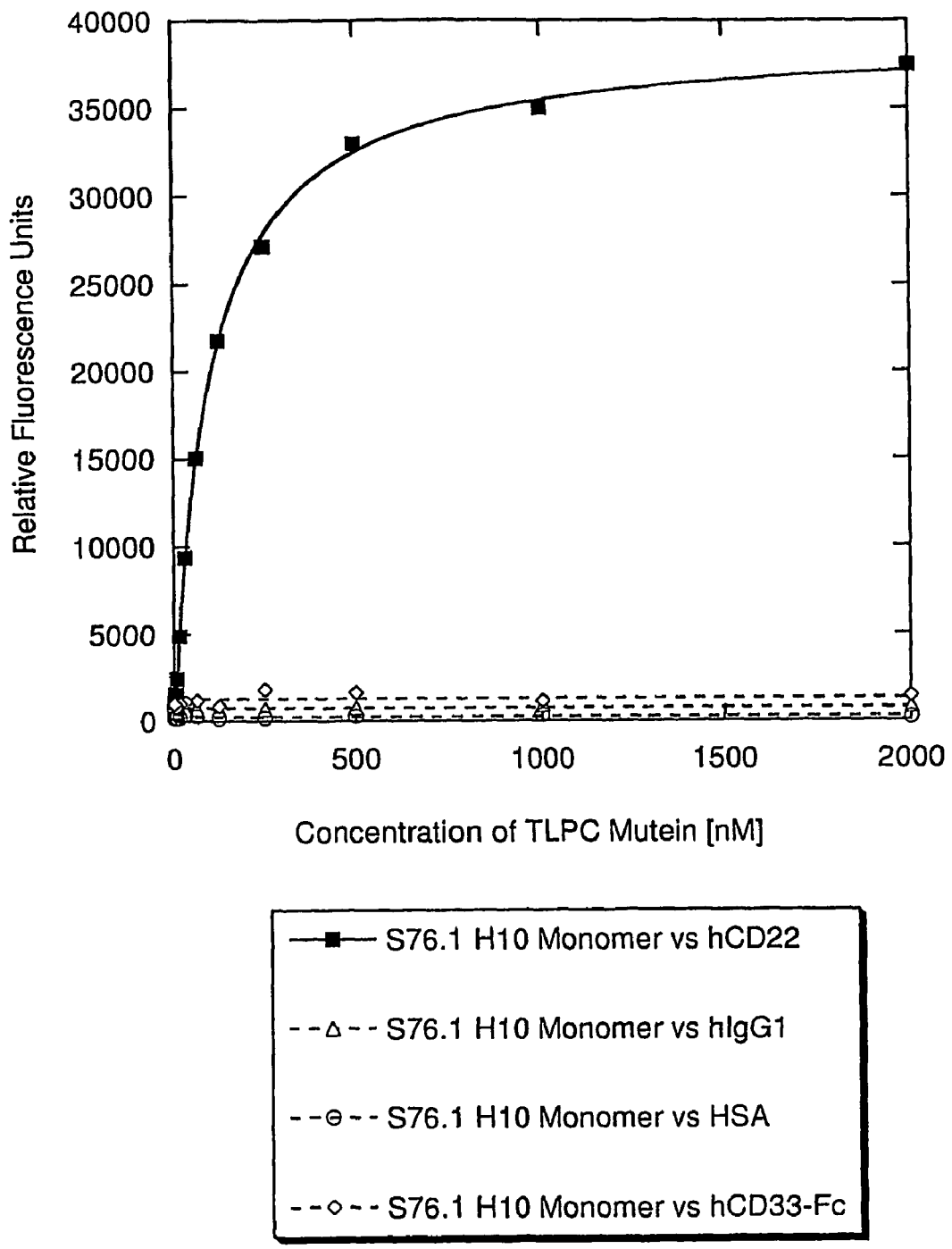
FIG. 10 depicts the binding of the TLPC mutein S76.1H10 Monomer to hCD22 in an ELISA.
Figure 11:
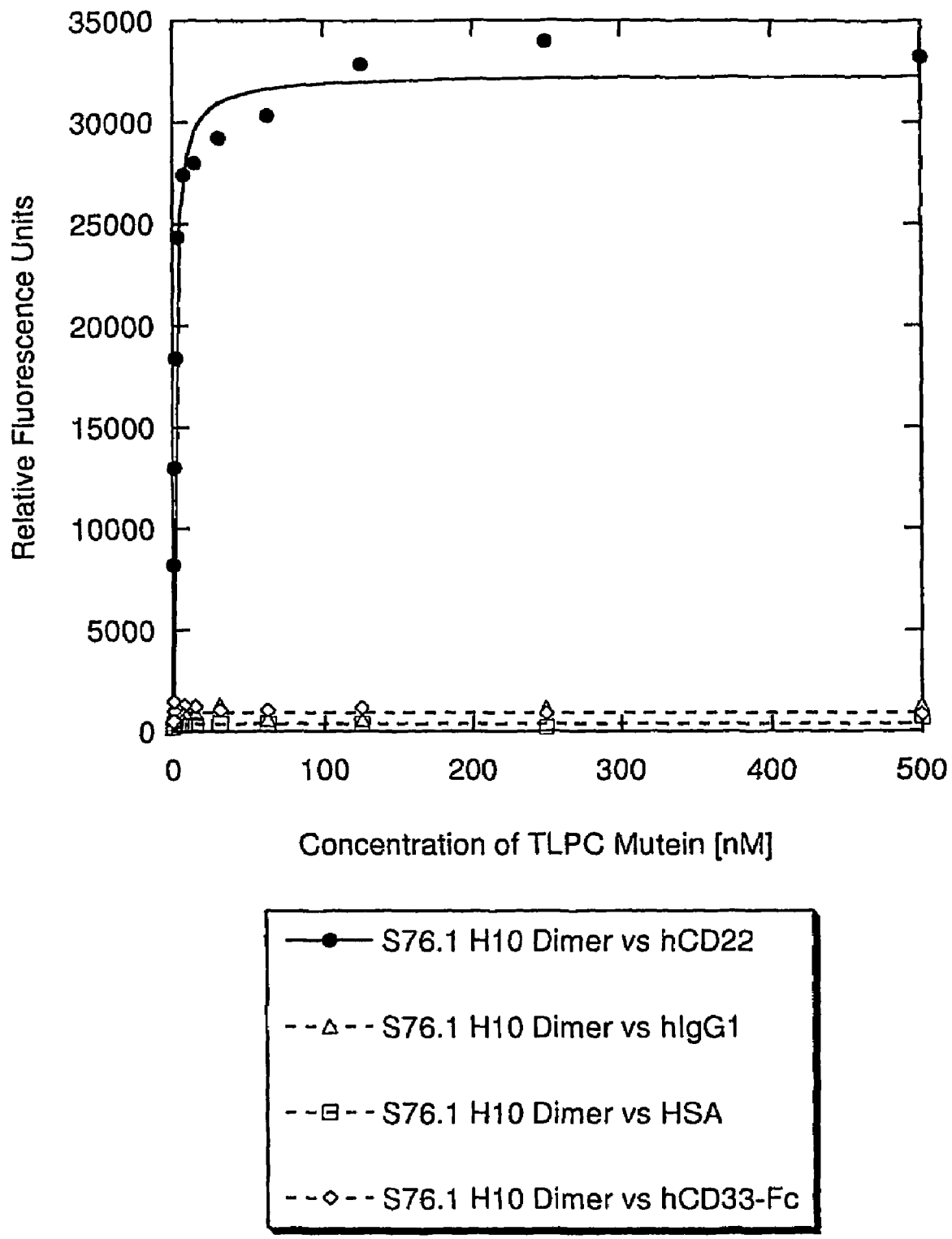
FIG. 11 depicts the binding of the TLPC mutein S76.1 H10 Dimer to hCD22 in an ELISA.

The resulting binding curves were depicted in FIG. 10 and FIG. 11. The values obtained for the apparent dissociation constants of the complexes between the TLPC mutein and the target protein hCD22 as well as complexes between the TLPC muteins and the control proteins hCD33-Fc (R&D Systems), human IgG1 (Jackson ImmunoResearch) and human serum albumin (HSA, Sigma) are summarized in Table 4. No measurable binding activity was obtained for the control proteins.

TABLE 4

Affinity binding constants of the TLPC muteins

| TLPC mutein | $k_D$ [nM]hCD22 | $k_D$ [nM]hCD33-Fc | $k_D$ [nM] hIgG1 | $k_D$ [nM] HSA |
|---|---|---|---|---|
| CD22 S76.1 H10 Monomer | 101 ± 3.3 | —* | —* | —* |
| CD22 S76.1 H10 Dimer | 1.4 ± 0.13 | —* | —* | —* |

*No detectable binding activity

Example 11

Phagemid Presentation and Selection of TPLC Muteins Against the Extracellular Domain of Human CD25 Employing Polystyrol Multiwell Plates The target used for the selection of CD25-specific muteins from the phagemid library described in Example 1 and the subsequent characterization of these muteins in ELISA experiments was purchased from R&D systems (recombinant human IL-2 R alpha/Fc Chimera).

For the selection of CD25-specific TLPC muteins from the phagemid library described in Example 1, 5 rounds of selection were performed, wherein the capture mAb (Mouse Anti-Human IgG, Fc$_{gamma}$ Fragment Specific; Jackson ImmunoResearch) was coated on the polystyrole plates at a concentration of 5 µg/ml. After blocking with 2.5% w/v BSA in PBS, CD25-Fc at a concentration of 5 µg/ml was added, incubated for one hour at RT and used for enrichment of CD25-specific phagemids. Adsorbed phagemids were eluted under denaturing conditions with 0.1 M glycine/HCl pH 2.2, as described in Example 3.

Example 12

Identification of a CD25-Binding TLPC Mutein by Use of a High-Throughput ELISA Screening Method For the analytical production of the TLPC muteins equipped with a C-terminal T7 detection tag (Novagen) as well as a C-terminal STREP-TAG® II affinity tag and their characterization by high-throughput ELISA screening, the gene cassette between the two BstXI cleavage sites was subcloned from the vector pTLPC7 (SEQ ID NO: 1FIG. 4) into pTLPC8 (SEQ ID NO: 24; FIG. 8).

For this purpose the plasmid DNA was isolated from the mixture of the *E. coli* clones obtained by infection with the phagemids from Example 11 eluted as a result of the last selection cycle. Screening for CD25-specific muteins was carried out according to the high-throughput ELISA protocol described in Example 4. Crude cell extracts were tested for binding to the specific target CD25 (immobilized to the microtiter plate as described in Example 11. In parallel, crude cell extracts were tested for binding to the unrelated proteins HSA, Human Gamma Globulin (Jackson ImmunoResearch) and capture mAb, coated at concentrations of 10 µg/1 ml, 10 µg/ml, and 5 µg/ml, respectively. Clones with specific binding properties were confirmed in a secondary high-throughput ELISA assay. In this assay, crude extracts were tested for binding to the same proteins as used for the primary screening and additional unrelated proteins (BSA, CD154 (recombinant human sCD40Ligand; Acris; Catalog Number: PA151XC) and milk, coated at 10 µg/ml, 5 µg/ml and 3%, respectively).

12 clones with a high signal on the specific target and low signals on the unrelated proteins were selected and the nucleotide sequence of the TLPC gene cassette was determined using the oligodeoxynucleotide SEQ ID NO: 37 as primer on an automated Genetic Analyzer system (Applied Biosystems) according to the instructions of the manufacturer employing the Big Dye Terminator Cycle Sequencing Kit (Applied Biosystems). One mutein was found to be enriched during the selection procedure. The nucleotide sequence of this clone, S67.7 C6, was translated into the amino acid sequence and those amino acids deviating from the modified TLPC encoded by pTLPC8 (SEQ ID NO: 24) are given in Table 5. The nucleotide sequence of S67.7 C6 is also given as SEQ ID NO: 20 (encoded protein sequence disclosed as SEQ ID NO: 52).

TABLE 5

Sequence characteristics of a selected TLPC mutein with specificity for CD25

| Pos Numbering according to wild-type Tlpc | Pos. Numbering according to the experimentally used truncated Tlpc | TLPC8 | S67.7 C6 |
|---|---|---|---|
| 8 | 4 | Glu | Val |
| 9 | 5 | Glu | Gly |
| 10 | 6 | Ile | Arg |
| 11 | 7 | Gln | Arg |
| 12 | 8 | Asp | Gly |
| 13 | 9 | Val | Leu |
| 43 | 39 | Thr | Gly |
| 45 | 41 | Glu | Ala |
| 70 | 66 | Lys | Gly |
| 72 | 68 | Asp | Asn |
| 74 | 70 | Pro | Leu |
| 75 | 71 | Gly | Asp |
| 90 | 86 | Arg | His |
| 94 | 90 | Lys | Thr |
| 97 | 93 | Tyr | Leu |

Example 13

Production of the TLPC Mutein

For the preparative production of the mutein S67.7 C6 described in Example 12, the *E. coli* K12 strain W3110 harbouring the expression vector pTLPC8 encoding this mutein was used for the periplasmatic production via fermenter cultivation as described in Example 5.

The mutein was purified from the periplasmic fraction in a single step chromatographic protocol with Strep-Tactin Superflow material (IBA) using a column of appropriate bed volume and suitable equipment according to the manufacturers' recommendations.

Gel filtration was carried out with Superdex 75 material (Amersham Pharmacia Biotech) using a column of appropriate bed volume and suitable equipment according to the manufacturers' recommendations. The monomeric fractions were pooled and used for the further characterization steps.

Example 14

Measurement of the Affinity of the TLPC Mutein for CD25 in ELISA

A dilution series of the mutein S67.7 C6 obtained as described in Example 13 was tested in an ELISA assay for binding to captured CD25-Fc and the control proteins capture mAb, HSA, FCS and captured human IgG Fc-fragment.

For this purpose, the wells of a black Fluotrac 600 microtiter plate (Greiner; 384 well) were coated with the capture mAb (Mouse Anti-Human IgG, Fc$_{gamma}$ Fragment Specific; Jackson ImmunoResearch) at a concentration of 5 µg/ml for 1 h at RT or O/N at 4° C. After a washing step and a subsequent blocking step with 3% w/v milk powder in PBST, CD25-Fc at a concentration of 5 µg/ml was added and incubated for one hour at RT. In parallel, the unrelated proteins capture mAb, HSA and FCS (Fetal Calf Serum; Invitrogen) were coated at concentrations of 5 µg/ml, 10 µl/ml and 10 µg/ml, respectively. In addition, human IgG Fc fragment (Accurate Chemical) was captured at a concentration of 5 µg/ml via the capture mAb coated at 5 µg/ml.

After another washing step, a dilution series of the mutein S67.7 C6 in PBST covering an appropriate concentration range was added to the captured CD25-Fc and the control proteins capture mAb, HSA, FCS and captured human IgG Fc fragment and incubated for 1 h at RT. Bound mutein was subsequently detected via Streptactin-HRP conjugate (IBA) and the fluorogenic HRP-substrate QUANTABLU™ (PIERCE) according to the respective manufacturers' recommendations. After an appropriate incubation time at room temperature, fluorescence was excited at a wavelength of 320 nm (±12.5 nm) and measured at 430 nm (±17.5 nm) in a GENiosPlus plate reader.

The curve was fitted by non-linear least squares regression with the help of the computer program Kaleidagraph (Synergy software) as described in Example 6.

Figure 12:
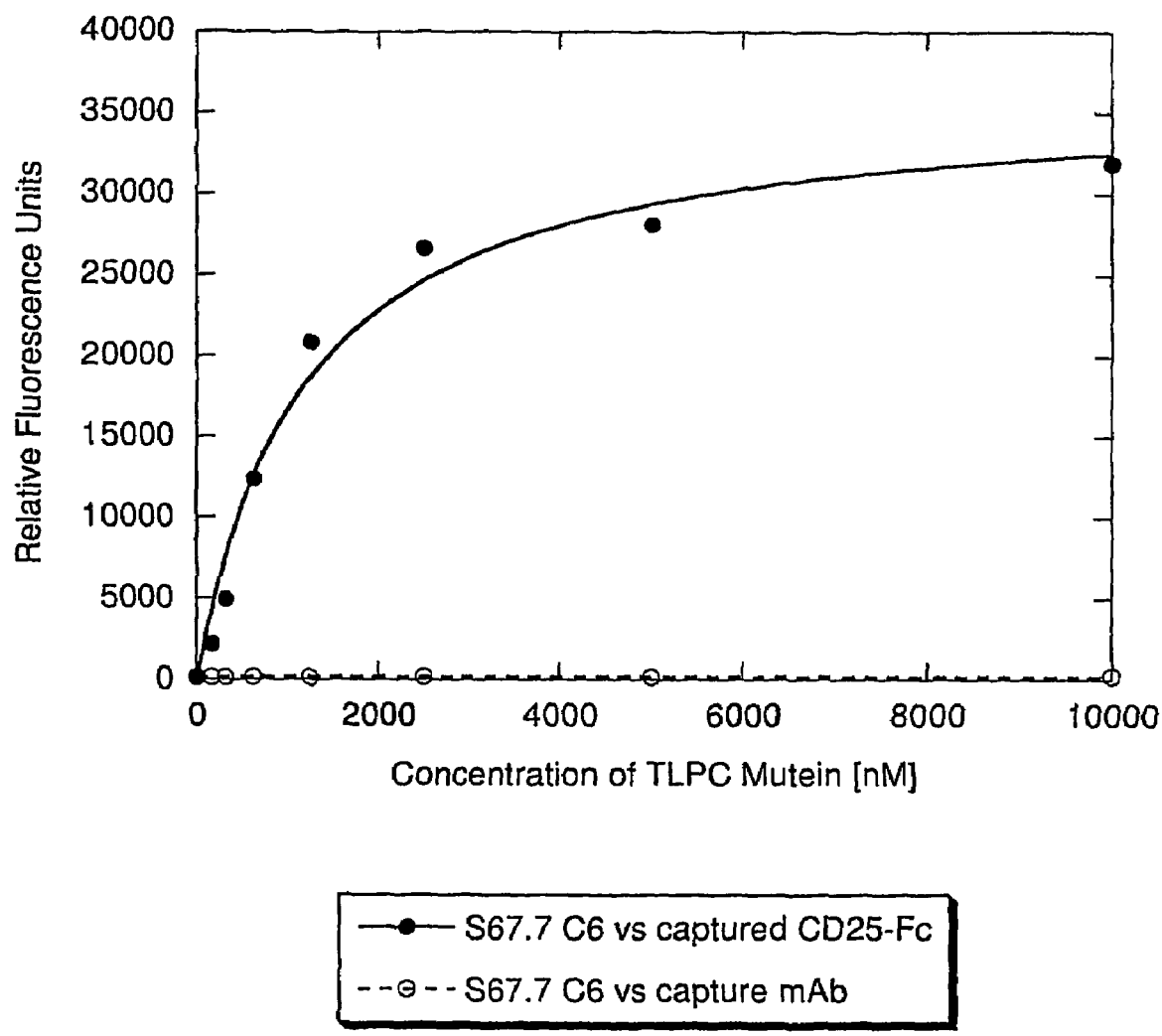
FIG. 12 depicts the binding of the TLPC mutein S67.7 C6 to human CD25 in an ELISA.

The resulting binding curves versus captured CD25-Fc and capture mAb are depicted in FIG. 12. The value obtained for the apparent dissociation constant of the complex between the TLPC mutein S67.7 C6 and the prescribed target protein CD25-Fc is summarized in Table 6. No measurable binding activity was obtained for the control proteins capture mAb, HSA, FCS and captured human IgG Fc fragment.

TABLE 6

Affinity binding constant between the TLPC mutein and CD25-Fc

| TLPC mutein | $K_D$ [nM] CD25-Fc |
|---|---|
| S67.7 C6 | 1178 ± 228 |

Example 15

Generation of a CHO Cell Line Expressing Human CD25

Figure 13:
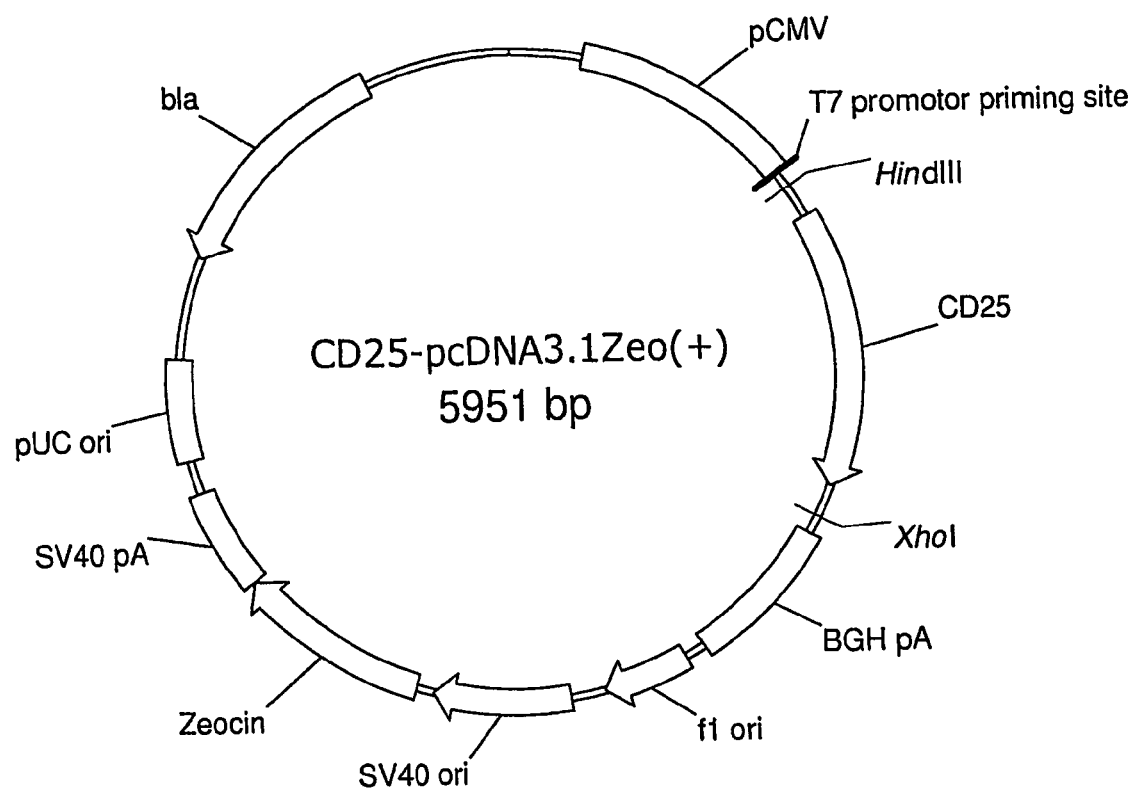
FIG. 13 schematically depicts the mammalian transfection vector CD25-pcDNA3.1Zeo(+).

For the generation of a stable cell line expressing human CD25, CHO-K1 cells (DSMZ, No. ACC 110) were transfected with the expression vector CD25-pcDNA3.1Zeo(+) (SEQ ID NO:10; FIG. 13) encoding human CD25 (NCBI ACCESSION NM_000417 [gi:4557666]).

The expression vector CD25-pcDNA3.1Zeo(+) was obtained as described in the following. The complete coding sequence of human CD25 was amplified from cDNA of human Peripheral Blood Lymphocytes by PCR using forward primer SEQ ID NO:35 and reverse primer SEQ ID NO:36. The PCR product coding for the full-length protein including the signal peptide was ligated into the cloning vector pCR-BluntII-TOPO (Invitrogen) according to the manufacturer's recommendations. The CD25 cDNA was excised from the resulting vector by XhoI/HindIII restriction digestion and isolated by agarose gel electrophoresis as described in Sambrook et al. (supra). The fragment was purified (Wizard SV Clean Up Kit, Promega) and ligated into the expression vector pcDNA3.1Zeo(+) (Invitrogen) which had been linearized with the same restriction enzymes. *E. coli* XL1-Blue was transformed with the resulting expression vector (CD25-pcDNA3.1Zeo(+)) and the DNA was extracted and purified using the EndoFree Plasmid Maxi Kit (Qiagen).

400,000 CHO-K1 cells (DSMZ, No. ACC 110) grown at 37° C. in DMEM Glutamax I medium (Gibco) containing 10% (v/v) FCS and 5% $CO_2$ were plated in 3.5 cm plates and were transfected the following day using 4 µg plasmid DNA and 10 μl Lipofectamine2000 (Invitrogen) according to the manufacturer's recommendations. Cells were either transfected with CD25-pcDNA3.1Zeo(+) or pcDNA3.1Zeo(+) as control. One day later, the cells were trypsinized and transferred into five 9.5 cm plates. The following day, selection started by addition of 200 μg Zeocin per ml medium. After one week, Zeocin-resistant clones were transferred into 24 well plates and subsequently cultured in T25 culture flasks (Greiner). CD25 expression of several clones was analyzed by FACS analysis as described in Example 16. Clones exhibiting the highest expression were kept, stocks were frozen and all further assays were performed with these cell lines up to passage no. 30.

Example 16

Testing of TLPC Mutein for Specific Binding to a CHO Cell Line Expressing Human CD25

The mutein S67.7 C6 was tested for specific binding to a CHO cell line expressing human CD25 in a flow cytometry assay. For this purpose, the CD25-pcDNA3.1Zeo(+)- or pcDNA3.1Zeo(+)-transfected CHO cells described in Example 15 were detached from culture flasks with 0.2% w/v EDTA. Approximately 200,000 cells were resuspended in 30 μl PBS/2% v/v FCS and incubated with 10 μg S67.7 C6 obtained as described in Example 13 and labeled with fluorescein (Fluorescein-5(6)-carboxamido caproic acid N-succinimidyl ester; Fluka) at an equimolar ratio based on the protocol described in Schlehuber and Skerra (*Biol. Chem.* (2001) 382, 1335-1342). As a negative control, 10 μg of the recombinant wild type TLPC encoded by pTLPC8 and labeled with fluorescein at an equimolar ratio was employed. CD25 expression was confirmed with FITC-labeled anti-CD25 mAb (Acris, DM519F), using FITC-labeled IgG1 (Acris, SM10F) as isotype control. After 30 min incubation on ice, cells were washed twice with PBS/2% v/v FCS prior to analysis by flow cytometry using a FACSCalibur (Becton Dickinson).

Figure 14:
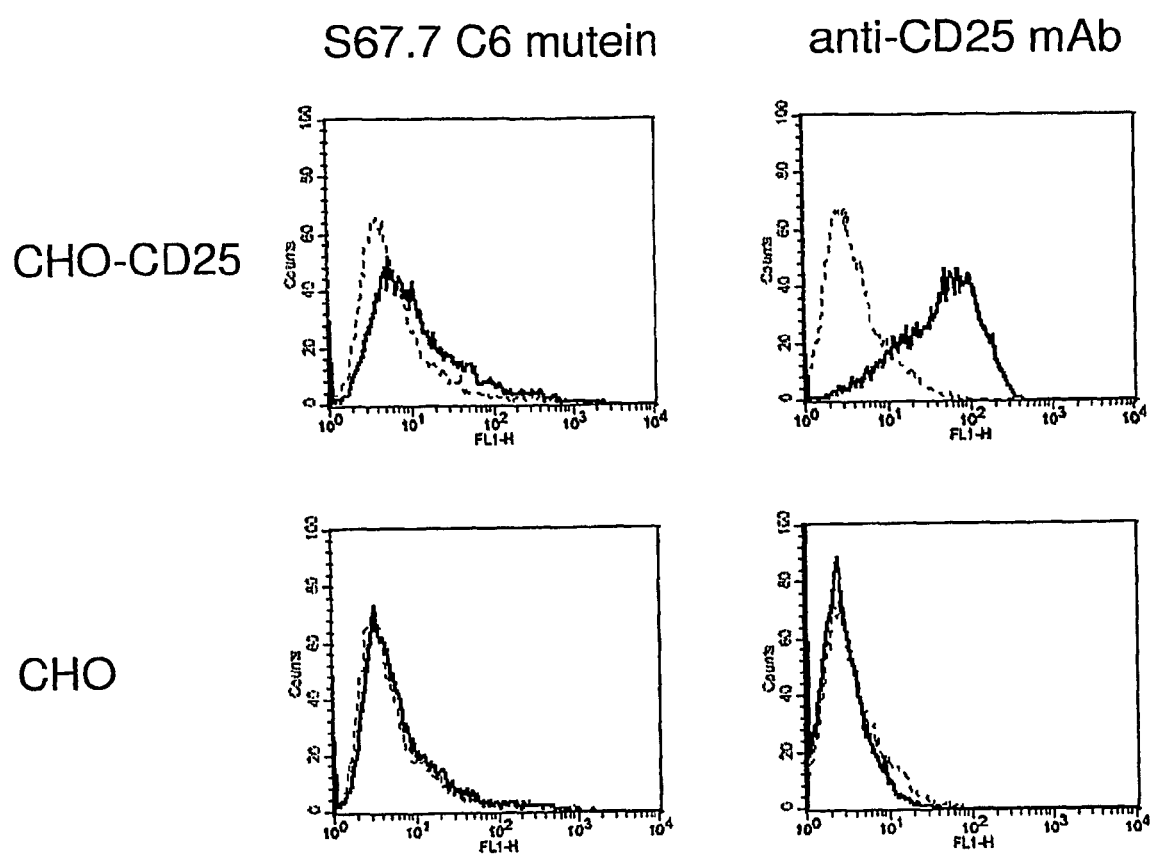
FIG. 14 shows the staining of CHO cells expressing human CD25 with fluorescein-labeled TLPC mutein S67.7 C6.

Both the CD25-specific mutein S67.7 C6 and the CD25-specific mAb show significant staining of the CHO cell line expressing human CD25 while no significant staining of the mock-transfected CHO cell line occurs. The controls wild type TLPC and IgG1 show no significant binding to both cell lines tested. The obtained histograms are depicted in FIG. 14.

Example 17

Generation of an Error-Prone-PCR Library for the Affinity Maturation of a CD25-Specific TLPC Mutein The CD25-specific mutein S67.7-C06 described in Example 12 was employed for an affinity maturation procedure. Therefore, a second generation library was prepared, based on mutein S67.7-C06, by employing an error-prone PCR protocol. This library, already having imprinted the binding information for CD25, was prepared employing the nucleotide analogs 8-oxodGTP and dPTP (TEBU-Bio) according to the method described in literature (Zaccolo et al. (1996) *J. Mol. Biol.* 255, 589-603). For the error-prone amplification reaction the 5' biotinylated oligonucleotides SEQ ID NO: 7 and SEQ ID NO: 8 were used together with the nucleotide analogs. Since these oligodeoxynucleotides are flanking the BstXI restriction sites, the amplification resulted in point mutations randomly distributed over the BstXI gene-cassette, which comprises most of the structural gene of the TLPC mutein. The PCR product was purified using the Wizard SV Gel and PCR Clean-Up System (Promega) and for cloning purposes, this fragment representing the affinity-matured library of TPLC muteins in nucleic acid form was first cut with the restriction enzyme BstXI (Promega) according to the instructions of the manufacturer and then purified as described above, resulting in a double stranded DNA-fragment of 303 nucleotides in size. DNA-fragments not or incompletely digested were removed via their 5'-biotin tags using streptavidin-coated paramagnetic beads (Merck) as described in Example 1.

For subsequent ligation of the affinity-matured muteins from above a 3907 fragment was prepared and purified from the DNA of the vector pTLPC7 (FIG. 4) as described in Example 1. For the ligation reaction, 3.32 μg (15 pmol) of the PCR fragment and 38.7 μg (15 pmol) of the vector fragment were incubated in the presence of 420 Weiss Units of T4 DNA ligase (Promega) in a total volume of 4200 μl (50 mM Tris/HCl pH 7.8, 10 mM $MgCl_2$, 10 mM DTT, 1 mM ATP, 50 μg/ml BSA) for 48 h at 16° C. The DNA in the ligation mixture was then precipitated by adding 105 μl yeast tRNA (10 mg/ml solution in $H_2O$ (Roche)), 4200 μl 5 M ammonium acetate, and 16.8 ml ethanol. Further processing was performed according to example 1 and at the end the DNA was dissolved to a final concentration of 200 μg/ml in a total volume of 210 μl of water.

The preparation and transformation of electrocompetent *E. coli* XL1-Blue (Bullock et al., supra) was carried out according to Example 1. By employing a total of 42 μg ligated DNA about $2.6 \times 10^9$ transformants were obtained in altogether 21 electroporation runs. The transformants were further used for preparation of phagemids as described in Example 7 of the PCT application WO 03/029471.

Example 18

Phagemid Presentation and Selection of Affinity-Improved CD25-Specific TPLC Muteins Employing Polystyrol Multiwell Plates For the selection of affinity-improved CD25-specific TLPC muteins from the error-prone PCR library described in Example 17, 3 rounds of selection were performed with 2 different strategies (selection strategy A and B, respectively) according to the general method described in Example 3. The deviations from the protocol are described in the following. Prior to the incubation with the target protein, phagemids from the library were incubated in BSA-blocked polystyrol wells 2 times for 15 minutes each for the depletion of phagemids presenting multi-reactive or misfolded lipocalin muteins.

The capture mAb (Mouse Anti-Human IgG, $Fc_{gamma}$ Fragment Specific; Jackson ImmunoResearch) was coated on the polystyrole plates at a concentration of 5 μg/ml. After blocking with 2.5% w/v BSA in PBS, CD25-Fc at a concentration of 0.063 μg/ml (selection strategy A) or 0.016 μg/ml (selection strategy B) was added and incubated for one hour at RT. Adsorbed phagemids were eluted under denaturing conditions and by competition using the bacterial strain XL1 blue as described in Example 7. In the first, second and third selection cycle about $2 \times 10^{11}$, $1 \times 10^{11}$ and $1 \times 10^{10}$ phagemids were used as input for the enrichment process; and 8, 10 and 12 washing cycles were performed, respectively. The phagemid amplification was performed as described in Example 3 except that the phagemids were incubated at 22° C. instead of 26° C.

Example 19

Figure 4:
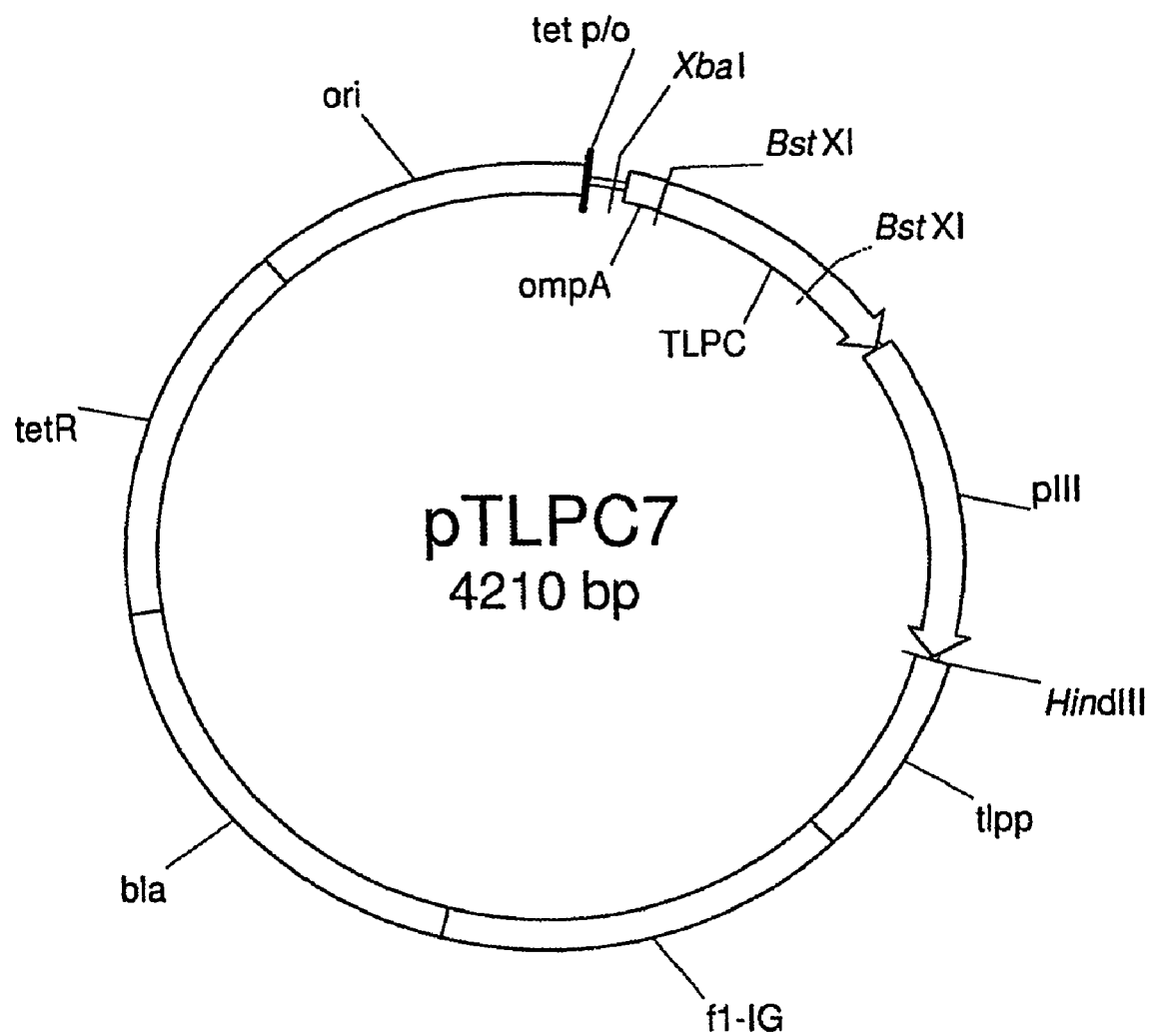
FIG. 4 schematically depicts the phagemid vector pTLPC7.
Figure 15:
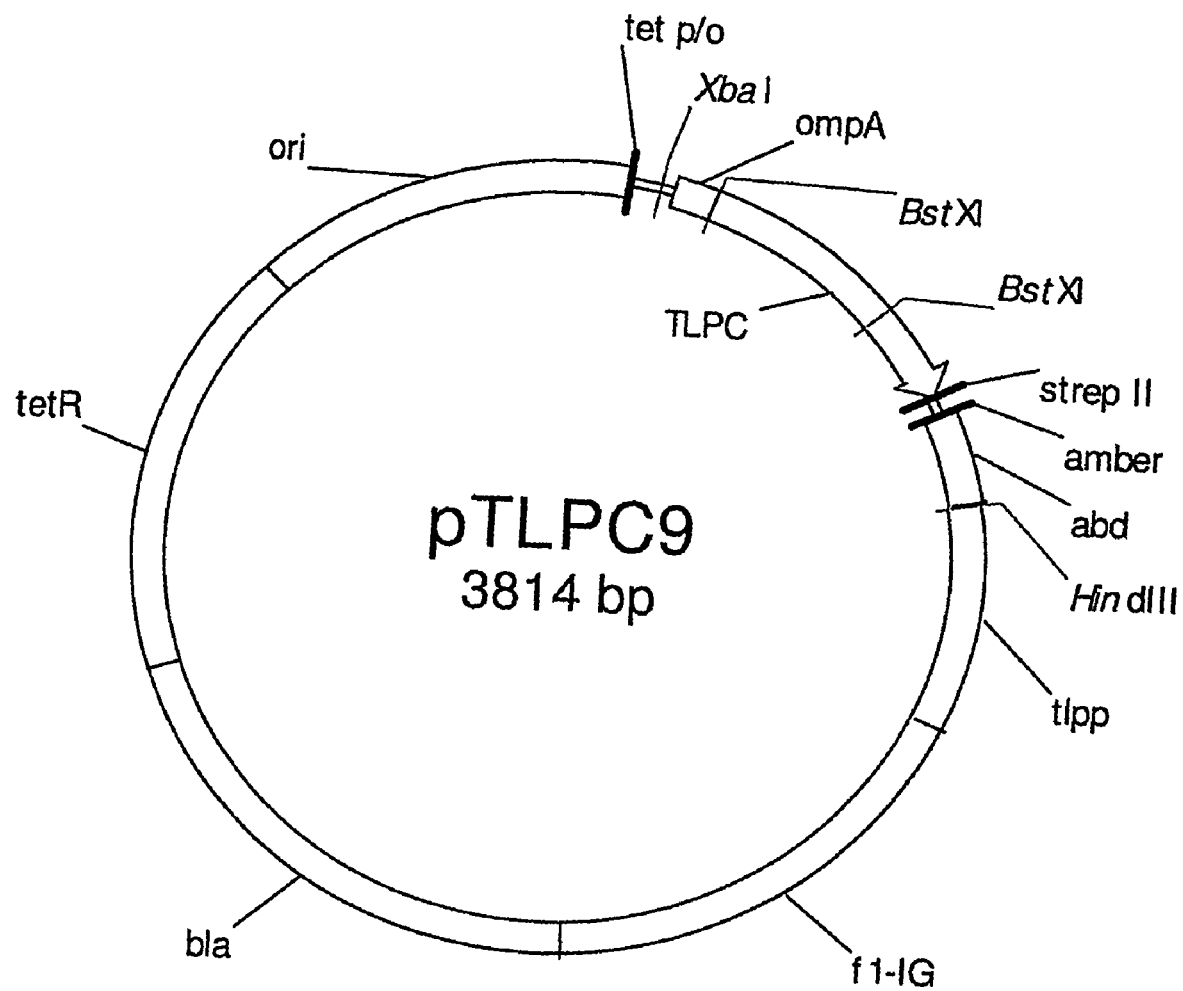
FIG. 15 schematically depicts the expression vector pTLPC9.

Identification of Affinity-Improved CD25-Specific TLPC Muteins by Use of the Colony Screening Method For the analytical production of the TLPC muteins as fusion proteins with the Strep-tag® II and the albumin-binding domain (ABD) and their characterization by colony screening, the gene cassette between the two BstXI cleavage sites was subcloned from the phagemid vector pTLPC7 (SEQ ID NO: 1; FIG. 4) into pTLPC9 (SEQ ID NO:22; FIG. 15).

For this purpose the plasmid DNA was isolated from the mixture of the *E. coli* clones obtained by infection with the phagemids of selection strategy B from Example 18 eluted as a result of the last selection cycle. After subcloning of the gene cassette into the screening vector pTLPC9 and transformation of *E. coli* K12 TG1-F cells, screening for affinity-improved, CD25-specific muteins was carried out via the filter-sandwich colony screening method based on the protocol described in Schlehuber, S. et al. (supra).

A collection of single clones obtained from O/N cultures in 384 well microtiter plates was spotted in duplicates in an identical pattern onto 6 hydrophilic PVDF membranes laid on top of LB/Amp agar plates by means of a 384 pin head (Genetix). After growth for 4 hours at 37° C., followed by another incubation step for 2 hours at 22° C., the hydrophilic membranes were placed on top of the hydrophobic membranes coated with HAS, which in turn were placed on top of LB/Amp agar plates containing 200 µg/l aTc. The culture plates were incubated with the stack of both membranes O/N at 22° C. During this phase the respective TLPC muteins were released from the colonies on the upper membranes and were immobilized via their albumin-binding domain to the HSA on the lower membranes.

For the identification of affinity-improved, CD25-specific muteins, the hydrophobic membranes were screened in parallel with 5 different concentrations of CD25-Fc (10 nM, 3 nM, 1 nM, 0.3 nM and 0.1 nM). Mutein/CD25-Fc complexes were detected via anti-human IgG-Fc-HRP conjugate (Peroxidase-conjugated Goat Anti-Human IgG, $Fc_{gamma}$ Fragment Specific; Jackson ImmunoResearch) and the chromogenic DAB substrate kit for peroxidase (Vector Laboratories) according to the respective manufacturers' recommendations. In parallel, mutein expression was monitored via Strep-tactin-HRP conjugate (IBA) and the DAB substrate kit according to the respective manufacturers' recommendations.

A total of 9 clones from selection strategy B with the highest signal on the lowest concentration of CD25-Fc was selected and the nucleotide sequence of the respective TLPC gene cassette was determined using the oligodeoxynucleotide SEQ ID NO: 37 as primer on an automated Genetic Analyzer system (Applied Biosystems) according to the instructions of the manufacturer employing the Big Dye Terminator Cycle Sequencing Kit (Applied Biosystems). 8 unique muteins containing a functional insert were identified. From these, 1 clone was selected for further characterization. The nucleotide sequence of this clone, F92.8 M1.2 E15, was translated into the amino acid sequence and those amino acids deviating from modified TLPC encoded by pTLPC9 (SEQ ID NO: 22) are given in Table 7. The nucleotide sequence of clone F92.8 M1.2 E15 is also given as SEQ ID NO: 21 (encoded protein sequence disclosed as SEQ ID NO: 53).

TABLE 7

Sequence characteristics of a selected TLPC mutein with improved affinity for CD25

| Pos. Numbering according to wild-type Tlpc | Pos. Numbering according to experimentally used truncted Tlpc | TLPC9 | F92.8 M1.2 E15 |
|---|---|---|---|
| 8 | 4 | Glu | Val |
| 9 | 5 | Glu | Gly |
| 10 | 6 | Ile | Arg |
| 11 | 7 | Gln | Arg |
| 12 | 8 | Asp | Gly |
| 13 | 9 | Val | Leu |
| 24 | 19 | Thr | Ala |
| 43 | 39 | Thr | Gly |
| 45 | 41 | Glu | Ala |
| 50 | 46 | Glu | Gly |
| 51 | 47 | Ala | Val |
| 70 | 66 | Lys | Gly |
| 72 | 68 | Asp | Asn |
| 74 | 70 | Pro | Leu |
| 75 | 71 | Gly | Asp |
| 90 | 86 | Arg | His |
| 94 | 90 | Lys | Thr |
| 97 | 93 | Tyr | Leu |
| 99 | 95 | Phe | Leu |

As can be seen from Table 7, the CD25 mutein F92.8 M1.2 E15 carries amino acid mutations compared to wild type Tlpc at the framework positions 23, 50, and 51.

Example 20

Production of the Affinity-Improved TLPC Mutein Selected by the Colony Screening Method For the preparative production of the mutein F92.8 M1.2 E15 described in Example 19, the *E. coli* K12 strain W3110 harbouring the expression vector pTLPC9 encoding this mutein was used for the periplasmatic production via fermenter cultivation as described in Example 5.

The mutein was purified from the periplasmic fraction in a single step chromatographic protocol with Strep-Tactin Superflow material (IBA) using a column of appropriate bed volume and suitable equipment according to the manufacturers' recommendations.

Gel filtration was carried out with Superdex 75 material (Amersham Pharmacia Biotech) using a column of appropriate bed volume and suitable equipment according to the manufacturers' recommendations. It was found, that the mutein F92.8 M1.2 E15 eluted from the size exclusion column in two distinct peaks, containing monomeric and dimeric protein, respectively. The monomeric and dimeric fractions were pooled and used for the further characterizations steps.

Example 21

Measurement of the Affinity of the Affinity-Improved TLPC Mutein for CD25 in ELISA A dilution series of the mutein F92.8 M1.2 E15 monomeric and dimeric fractions obtained as described in Example 20 was tested in an ELISA assay for binding to captured CD25-Fc and the control proteins capture mAb, HSA, FCS and captured human IgG Fc-fragment.

The assay was performed as described in Example 14, except that 2.5 µg/ml CD25-Fc and 2.5 µg/ml human IgG Fc-fragment were used for capturing.

Figure 16:
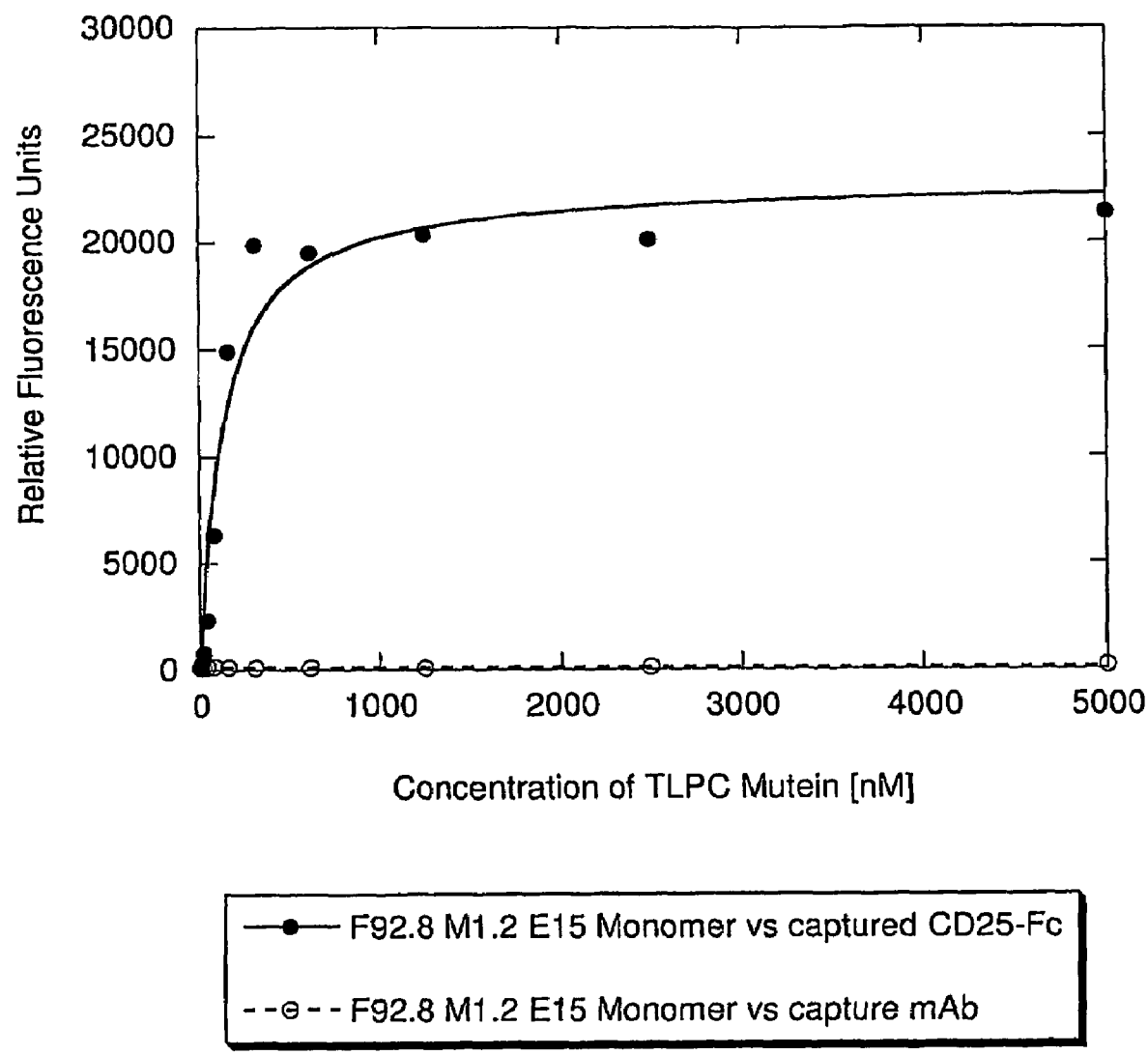
FIG. 16 depicts the binding of the monomeric fraction of the TLPC mutein F92.8 M1.2 E15 to human CD25 in an ELISA.
Figure 17:
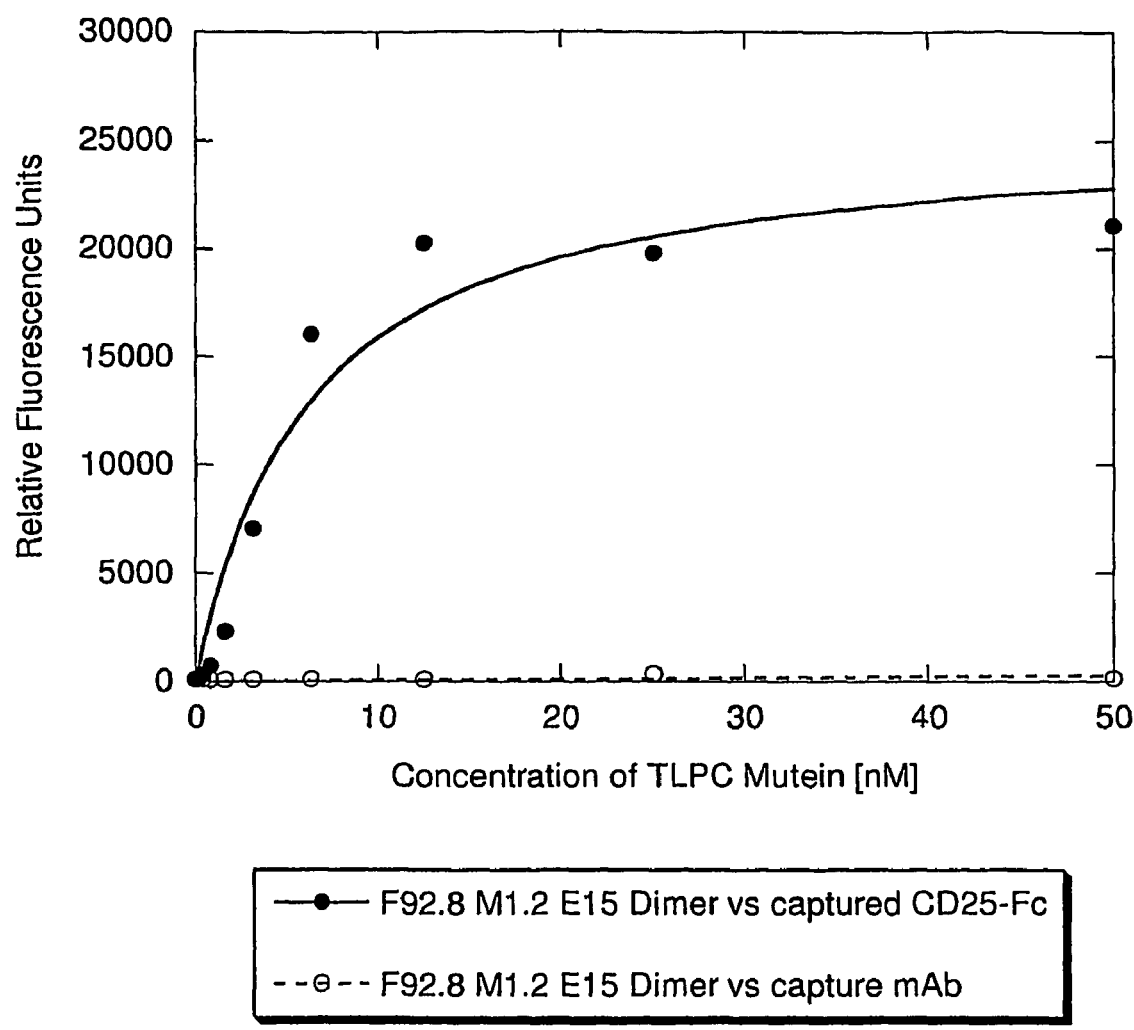
FIG. 17 depicts the binding of the dimeric fraction of the TLPC mutein F92.8 M1.2 E15 to human CD25 in an ELISA.

The resulting binding curves versus captured CD25-Fc and capture mAb are depicted in FIG. 16 and FIG. 17, respectively. The values obtained for the apparent dissociation constants of the complex between the TLPC mutein F92.8 M1.2 E15 monomer or dimer and the prescribed target protein CD25-Fc are summarized in Table 8. No measurable binding activity was obtained for the control proteins capture mAb, HSA, FCS and captured human IgG Fc fragment.

TABLE 8

Affinity binding constants between the affinity-improved TLPC mutein and CD25-Fc

| TLPC mutein | $K_D$ [nM] CD25-Fc |
|---|---|
| F92.8 M1.2 E15 monomer | 131 ± 34 |
| F92.8 M1.2 E15 dimer | 6 ± 1.8 |

Example 22

Generation of a CHO Cell Line Expressing Human CD154

Figure 18:
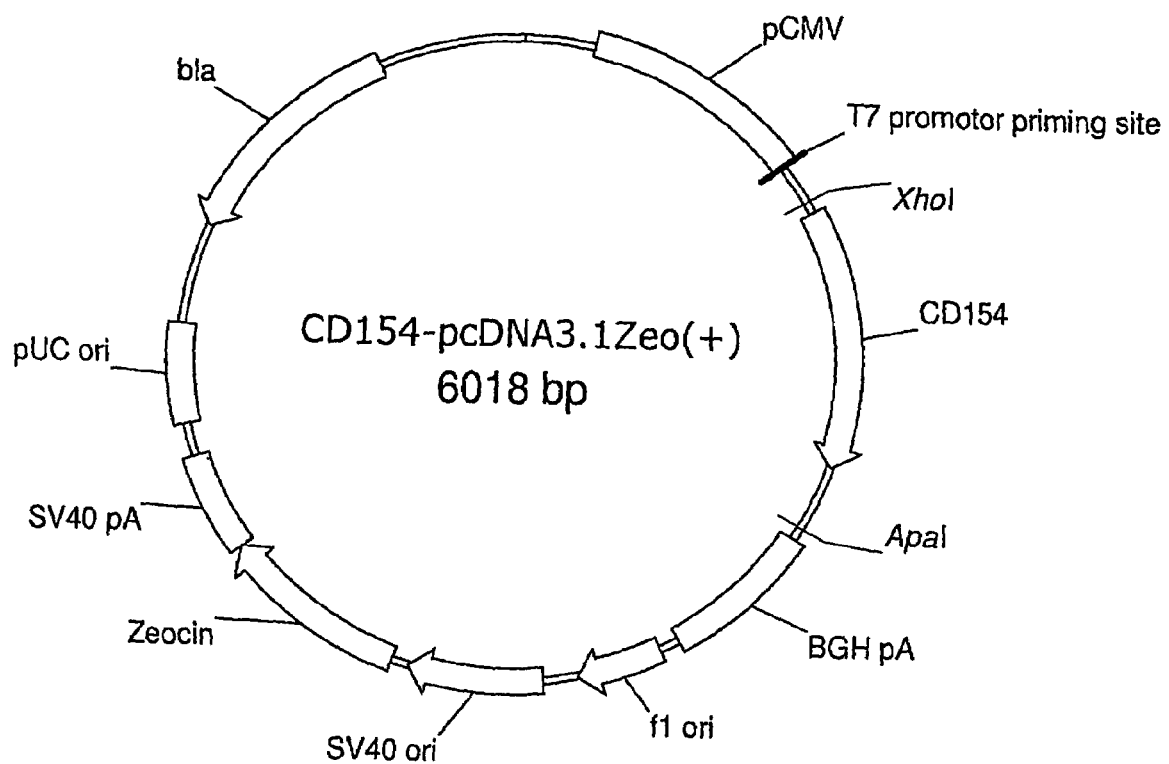
FIG. 18 schematically depicts the mammalian transfection vector CD154-pcDNA3.1Zeo(+).

For the generation of a stable cell line expressing human CD154, CHO-K1 cells (DSMZ, No. ACC 110) were transfected with the expression vector CD154-pcDNA3.1Zeo(+) (SEQ ID NO:11; FIG. 18) encoding human CD154 (NCBI ACCESSION BC_074950 [gi:49902361]).

The expression vector CD154 pcDNA3.1Zeo(+) was obtained as described in the following. We obtained the DNA encoding for human CD154 (NCBI ACCESSION BC_074950 [gi:49902361]) from a pLXSN vector (BD Biosciences Clontech) in which CD154 was subcloned. The correct sequence for the complete cDNA was confirmed by sequencing of the plasmid employing the oligonucleotides SEQ ID NO: 38 and SEQ ID NO: 39. The DNA-fragment encoding the complete sequence of human CD154 was excised from this vector via restriction digest with XhoI/ApaI and isolated by agarose gel electrophoresis as described in Sambrook et al. (supra). The fragment was purified (Wizard SV Clean Up Kit, Promega) and ligated into the expression vector pcDNA3.1Zeo(+) (Invitrogen) which had been linearized with the same restriction enzymes. XL1-Blue bacteria were transformed with the resulting expression vector CD154-pcDNA3.1Zeo(+) and the DNA was extracted and purified using the EndoFree Plasmid Maxi Kit (Qiagen).

Growth and transfection of CHO-K1 cells (DSMZ, No. ACC 110) with the expression vector CD154-pcDNA3.1Zeo (+) was carried out based on the protocol described in Example 15. CD154 expression of several clones was analyzed by FACS analysis as described in Example 23. Clones exhibiting the highest expression were used for all further assays up to passage no. 30.

Example 23

Testing of Affinity-Improved TLPC Mutein for Specific Binding to CHO Cell Line Expressing Human CD25

The mutein F92.8 M1.2 E15 was tested for specific binding to a CHO cell line expressing human CD25 in a flow cytometry assay. For this purpose, the CD25-pcDNA3.1 Zeo(+)- or CD154-pcDNA3.1Zeo(+)-transfected CHO cells described in Examples 15 and 22, respectively were detached from culture flasks with 0.2% w/v EDTA. Approximately 200,000 cells were resuspended in 30 µl PBS/2% v/v FCS and incubated with 2.5 µg of monomeric F92.8 M1.2 E15 fraction obtained as described in Example 20 and labeled at a twofold molar ratio with fluorescein (Fluorescein-5(6)-carboxamido caproic acid N-succinimidyl ester; Fluka) based on the protocol described in Schlehuber and Skerra (supra). As a negative control, 2.5 µg of the recombinant wild type TLPC encoded by pTLPC8 and labeled with fluorescein at a twofold molar ratio was employed. CD25 expression was confirmed with FITC-labeled anti-CD25 mAb (Acris, DM519F), using FITC-labeled IgG1 (Acris, SM10F) as isotype control. After 30 min incubation on ice, cells were washed twice with PBS/2% v/v FCS prior to analysis by flow cytometry using a FACSCalibur (Becton Dickinson).

Figure 19:
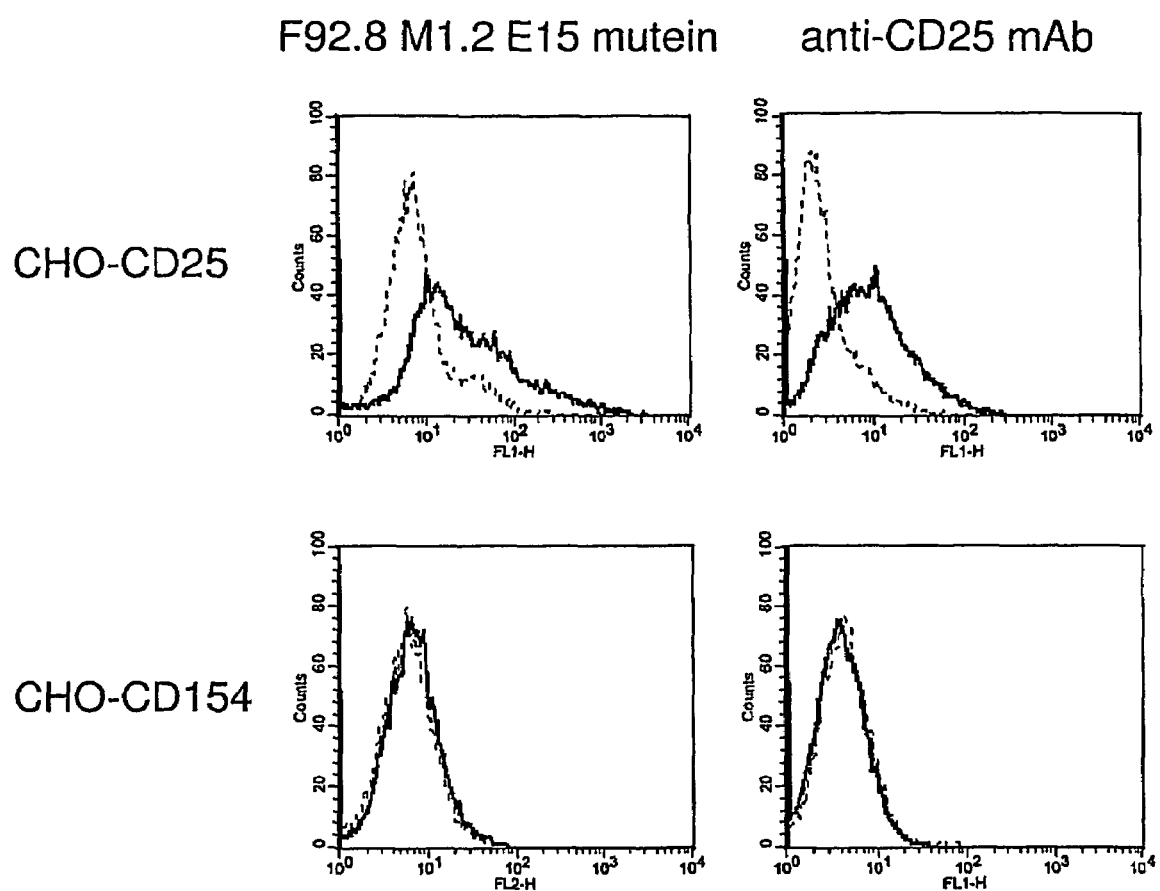
FIG. 19 shows the staining of CHO cells expressing human CD25 with fluorescein-labeled TLPC mutein F92.8 M1.2 E15.

Both the affinity-improved CD25-specific mutein F92.8 M1.2 E15 and the CD25-specific mAb show significant staining of the CHO cell line expressing human CD25 while no significant staining of the CHO cell line expressing human CD154 occurs. The controls wild type TLPC and IgG1 show no significant binding to both cell lines tested. The obtained histograms are depicted in FIG. 19.

Example 24

Identification of Affinity-Improved CD25-Binding TLPC Muteins by Use of a High-Throughput ELISA Screening Method For the analytical production of the affinity-improved TLPC muteins equipped with a C-terminal T7 detection tag (Novagen) as well as a C-terminal STREP-TAG® II affinity tag and their characterization by high-throughput ELISA screening, the gene cassette between the two BstXI cleavage sites was subcloned from the vector pTLPC7 (FIG. 4) into pTLPC8 (FIG. 8).

For this purpose the plasmid DNA was isolated from the mixture of the *E. coli* clones obtained by infection with the phagemids from Example 18 eluted as a result of the last selection cycle. Screening for affinity-improved, CD25-specific muteins was carried out according to the high-throughput ELISA protocol described in Example 4. Crude cell extracts were tested for binding to CD25-Fc captured at different concentrations (5 µg/ml, 1 µg/ml, 0.2 µg/ml, 0.04 µg/ml and 0.008 µg/ml, respectively). In parallel, crude cell extracts were tested for binding to human IgG Fc-fragment (Accurate Chemical) captured at a concentration of 5 µg/ml via the capture mAb which was coated at 5 µg/ml. Clones showing specific binding properties and retaining high signals on the lowest target concentrations were confirmed in a secondary high-throughput ELISA. In this assay, crude extracts were tested for binding to CD25-Fc captured at 1 µg/ml and 0.1 µg/ml. In addition, crude extracts were tested for binding to the unrelated proteins capture mAb, HSA, CD154 and Human Gamma Globulin (Jackson ImmunoResearch), coated at 5 µg/ml, 10 µg/ml, 5 µg/ml and 10 µg/ml, respectively.

A total of 13 clones from both selection strategies giving rise to a high signal at the lowest concentrations of captured CD25-Fc and low signals on the unrelated proteins was selected and the nucleotide sequence of the respective TLPC gene cassette was determined using the oligodeoxynucleotide SEQ ID NO: 37 as primer on an automated Genetic Analyzer system (Applied Biosystems) according to the instructions of the manufacturer employing the Big Dye Terminator Cycle Sequencing Kit (Applied Biosystems). 7 unique muteins containing a functional insert were identified. From these, 3 clones were selected for further characterization. The nucleotide sequence of these clones, S99.3 H24 and S99.3 C13 derived from selection strategy A and S99.4 F 15 obtained from selection strategy B, was translated into the amino acid sequence and those amino acids deviating from modified TLPC encoded by pTLPC8 (SEQ ID NO: 24) are given in Table 9. The nucleotide sequence of clones S99.3 H24, S99.3 C13 and S99.4 F15 is also given as SEQ ID NO: 17 (encoded protein sequence disclosed as SEQ ID NO: 49), SEQ ID NO: 18 (encoded protein sequence disclosed as SEQ ID NO: 50) and SEQ ID NO: 19 (encoded protein sequence disclosed as SEQ ID NO: 51), respectively.

TABLE 9

Sequence characteristics of selected TLPC muteins with improved affinity for CD25

| Pos. Numbering according to wild-type Tlpc | Pos. Numbering according to exp used truncted Tlpc | TLPC8 | S99.3 H24 | S99.3 C13 | S99.4 F15 |
|---|---|---|---|---|---|
| 8 | 4 | Glu | Val | Val | Val |
| 9 | 5 | Glu | Gly | Gly | Gly |
| 10 | 6 | Ile | Lys | Arg | Arg |
| 11 | 7 | Gln | Arg | Arg | Arg |
| 12 | 8 | Asp | Gly | Gly | Gly |
| 13 | 9 | Val | Leu | Leu | Leu |
| 28 | 24 | Phe | Phe | Ser | Ser |
| 32 | 28 | Asn | Asp | Asn | Asn |
| 43 | 39 | Thr | Gly | Gly | Gly |
| 45 | 41 | Glu | Ala | Ala | Ala |
| 67 | 63 | Val | Val | Ala | Val |
| 70 | 66 | Lys | Gly | Gly | Gly |
| 72 | 68 | Asp | Asn | Asn | Asn |
| 74 | 70 | Pro | Leu | Leu | Leu |
| 75 | 71 | Gly | Asp | Asp | Asp |
| 86 | 82 | Ala | Ala | Val | Ala |
| 90 | 86 | Arg | His | His | His |
| 91 | 87 | Ser | Pro | Pro | Pro |
| 94 | 90 | Lys | Thr | Thr | Thr |
| 97 | 93 | Tyr | Leu | Leu | Leu |

As can be seen from Table 9, the Tlpc muteins identified from the affinity maturation contained not only mutations in the binding site at the closed end of the β-barrel structure but also mutations in the peptide segments forming the natural lipocalin binding pocket (here residues 28, 32 of AB peptide loop) and at positions of the framework region (positions 67 and 86 of the Tlpc sequence, respectively).

Example 25

Production of the Affinity-Improved TLPC Mutein Selected by the High-Throughput ELISA Screening Method For the preparative production of the muteins S99.3 H24, S99.3 C13 and S99.4 F15 described in Example 24, the *E. Coli* K12 strain W3110 harbouring the expression vector pTLPC8 encoding these muteins was used for the periplasmatic production via fermenter cultivation as described in Example 5.

The mutein was purified from the periplasmic fraction in a single step chromatographic protocol with Strep-Tactin Superflow material (IBA) using a column of appropriate bed volume and suitable equipment according to the manufacturers' recommendations.

Gel filtration was carried out with Superdex 75 material (Amersham Pharmacia Biotech) using a column of appropriate bed volume and suitable equipment according to the manufacturers' recommendations. The monomeric fractions were pooled and used for the further characterizations steps.

Example 26

Measurement of the Affinity of the Affinity-Improved TLPC Mutein for CD25 in ELISA A dilution series of the muteins S99.3 H24, S99.3 C13 and S99.4 F15 obtained as described in Example 25 was tested in an ELISA assay for binding to captured CD25-Fc and the control proteins capture mAb, HSA, FCS and captured human IgG Fc-fragment.

The assay was performed as described in Example 14, except that 2.5 µg/ml CD25-Fc and 2.5 µg/ml human IgG Fc fragment were used for capturing.

Figure 20:
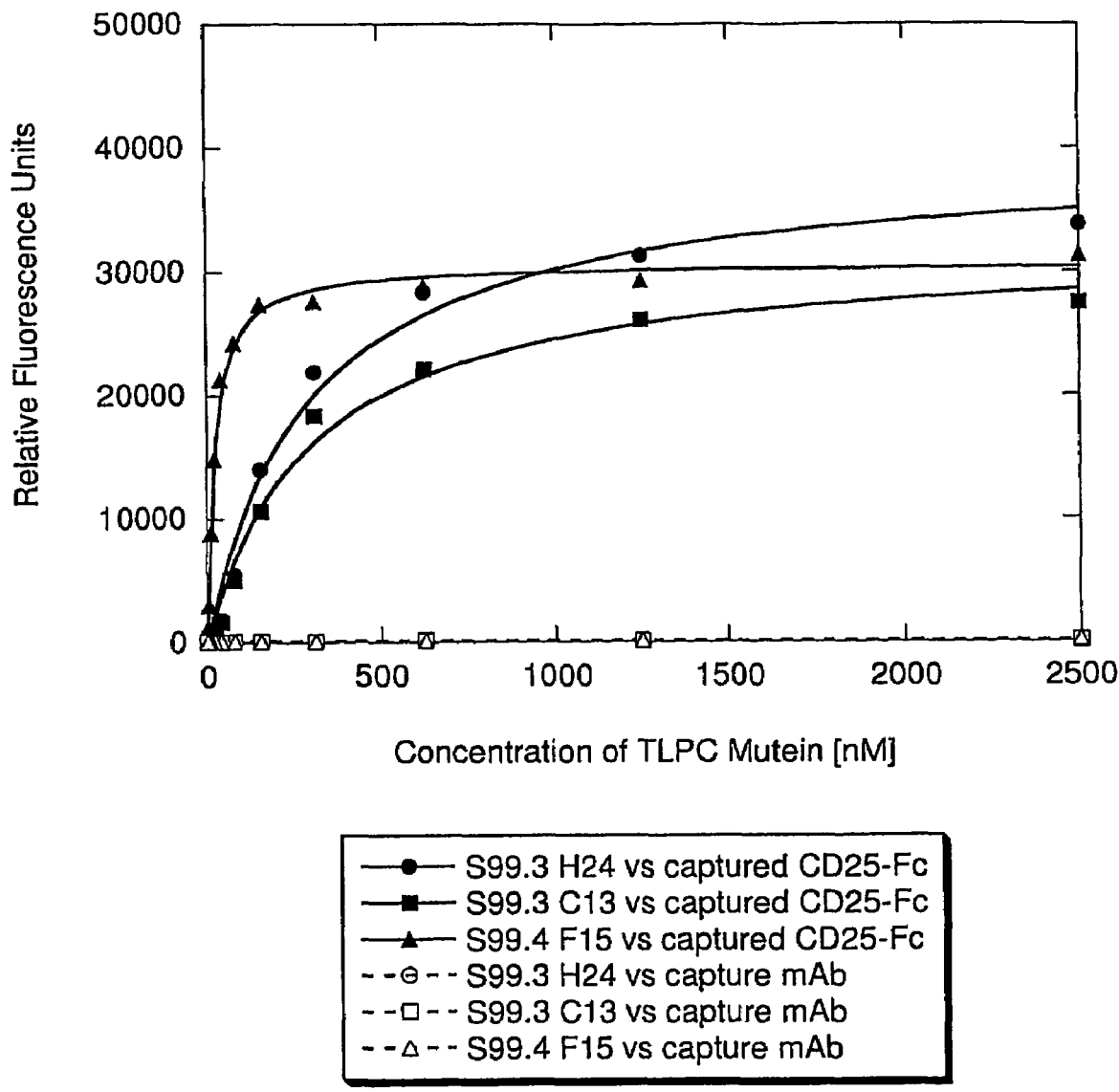
FIG. 20 depicts the binding of the TLPC muteins S99.3 H24, S99.3 C13 and S99.4 F15, respectively to human CD25 in an ELISA.

The resulting binding curves versus captured CD25-Fc and capture mAb are depicted in FIG. 20. The values obtained for the apparent dissociation constants of the complex between the TLPC muteins S99.3 H24, S99.3 C13 and S99.4 P15 and the prescribed target protein CD25-Fc are summarized in Table 10. No measurable binding activity was obtained for the control proteins capture mAb, HSA, FCS and captured human IgG Fc-fragment.

TABLE 10

Affinity binding constants between the affinity-improved TLPC muteins and CD25-Fc

| TLPC mutein | $K_D$ [nM] CD25-Fc |
|---|---|
| S99.3 H24 | 302 ± 46 |
| S99.3 C13 | 307 ± 43 |
| S99.4 F15 | 22 ± 2.4 |

Example 27

Phagemid Presentation and Selection of TPLC Muteins Against the Extracellular Domain of Human CD33-Fc Employing Polystyrol Multiwell Plates and Protein A Magnetic Beads For the selection of TLPC muteins the phagemid library, as described in Example 2, was used. The selection of TLPC muteins employing polystyrol multiwell plates was performed as described in Example 3. The deviations from the protocol are described in Example 7. The target hCD33-Fc (R&D Research) was directly coated on the polystyrol plates with a concentration of 1 µg/ml.

The selection of TLPC muteins was performed employing protein A beads (Dynabeads Protein A, Dynal) essentially following the instructions of the manufacturer. BSA was chosen as blocking agent for phagemids and target. The phagemids were eluted under acidic (0.1 M glycin/Hcl pH 2.2; 10 min RT; neutralization with 0.5 M Tris-base) and/or basic conditions (70 mM triethylamine; 10 min RT; neutralization with 1 M Tris/HCl, ph 7.4) followed by a final bacterial elution step, as described in Example 7.

The deviations from the protocol are described in Example 7 with the exception, that prior to incubation with the target protein phagemids from the library were incubated with 100 µl of BSA-blocked protein A beads, 2 times for 15 minutes each, for the depletion of phagemids presenting multi-reactive or misfolded lipocalin muteins.

Four rounds of selection against hCD33-Fc were carried out in this way employing the preparation of amplified phagemids from the respective previous enrichment cycle with the exception that only about 1·10^11 phagemids were utilized beginning with the second cycle.

Example 28

Figure 21:
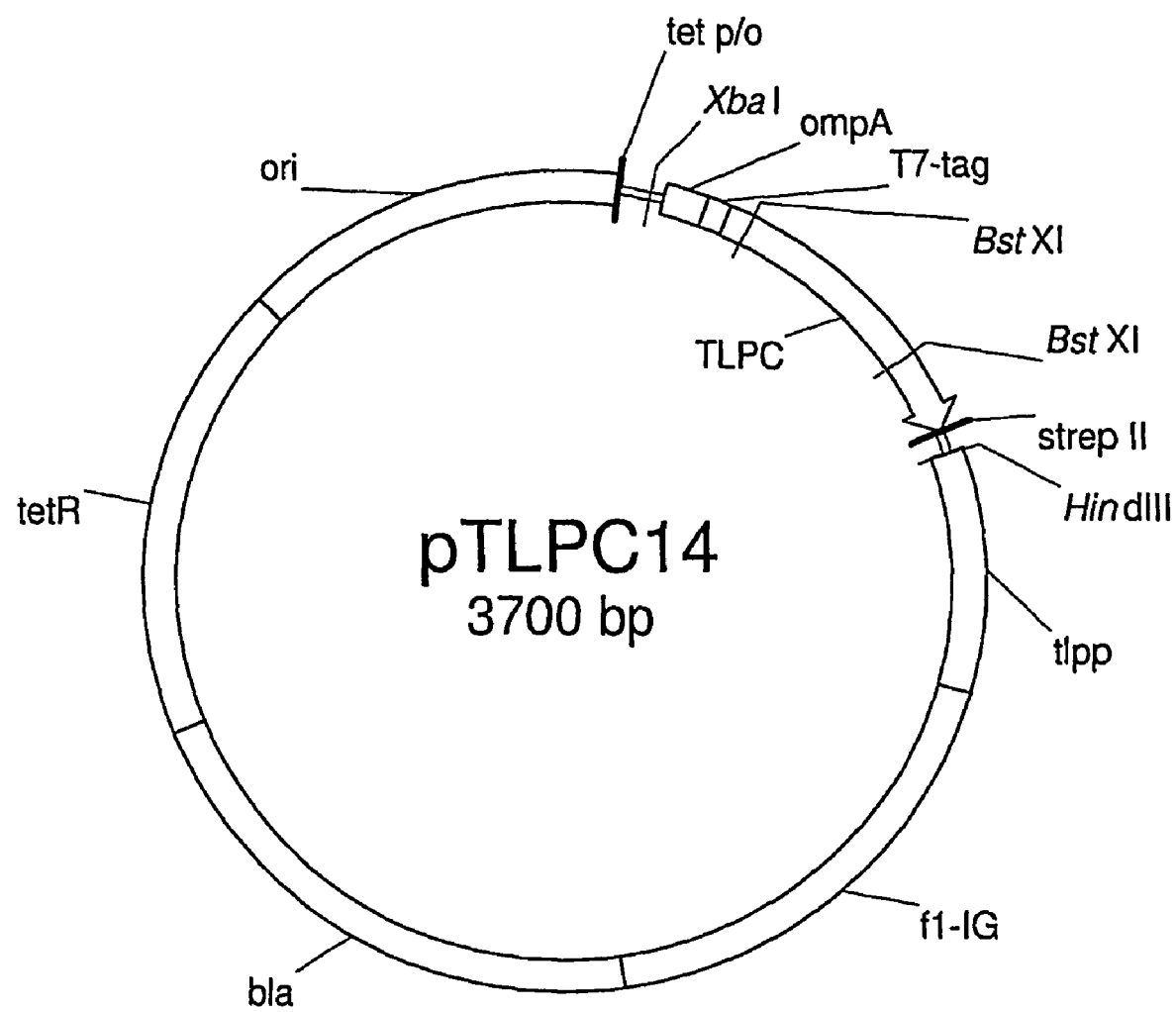
FIG. 21 schematically depicts the expression vector pTLPC14.

Identification of hCD33-Binding TLPC Muteins by Use of a High-Throughout ELISA Screening Method For the analytical production of the hCD33-binding TLPC muteins equipped with an N-terminal T7 detection tag (Novagen) as well as a STREP-TAG® II affinity tag at the C-terminus and their characterization by high-throughput ELISA screening, the gene cassette containing the TLPC between the two BstXI cleavage sites was subcloned from the vector pTLPC12 (FIG. 7) into the vector pTLPC14 (FIG. 21). The hCD33-binding TLPC muteins were identified by a high-throughput ELISA screening method as described in example 4. TLPC muteins that bound hCD33 specifically in the primary screening were selected for more detailed binding analysis in a secondary high-thoughput ELISA screening experiment as described in the same example.

For the detection of target-specificity of the recombinant TLPC muteins, wells of black Fluotrac 600 ELISA plates (Greiner; 384 well) were coated overnight at 4° C. with 20 µl of a solution of AffiniPure mouse anti-human IgG Fc$_{Gamma}$ fragment-specific antibody (5 µg/ml, Jackson ImmunoResearch) and as a control, with hCD22 (5 µg/ml, Peprotech), hIgG1 (10 g/ml, Jackson ImmunoResearch), streptactin (10 µg/ml, BA), human serum albumin (10 µg/ml, Sigma) as well as a conjugate of RNase A (10 µg/ml; RNase from Fluka) and digoxin. The target hCD33-Fc was captured via the anti-human IgG Fc$_{Gamma}$ fragment-specific antibody for 1 h at RT.

Multiple TLPC muteins turned out to bind hCD33-Fc specific and the nucleotide sequence of the TLPC gene cassette was determined from several clones using the oligodeoxynucleotide SEQ ID NO: 37 as a primer on an automated Genetic Analyzer system (Applied Biosystems) according to the instructions of the manufacturer employing the Big Dye Terminator Cycle Sequencing Kit (Applied Biosystems).

The sequencing of clones revealed from the polystyrol multiwell panning revealed 4 different lipocalin muteins. Two of them were analysed further. The nucleotide sequence of these clones was translated into the amino acid sequence and those amino acids deviating from the modified TLPC encoded by TLPC14 (FIG. 21) are given in Table 11. The nucleotide sequences of these lipocalin muteins, named S101.2 O08 and S101.2 A20, are given as SEQ ID NO 16 (encoded protein sequence disclosed as SEQ ID NO: 48), and SEQ ID NO 15 (encoded protein sequence disclosed as SEQ ID NO: 47), respectively.

The sequencing of clones selected from the protein A bead panning revealed two different lipocalin muteins. The nucleotide sequence of the clone S100.1-I08, chosen for further analysis, was translated into the amino acid sequence and those amino acids deviating from the modified TLPC encoded by TLPC14 (FIG. 21) are given in Table 11. The nucleotide sequence is also given as SEQ ID NO: 25 (encoded protein sequence disclosed as SEQ ID NO: 57).

TABLE 11

Sequence characteristics of selected anti-hCD33-Fc muteins

| Pos. Numbering according to the wild type Tlpc | TLPC | S101.2-A20 | S101.2-O08 | S100.1-I08 |
|---|---|---|---|---|
| 25 | Asp | Val | Pro | Gly |
| +4 | | — | — | — |
| +3 | | — | — | — |
| +2 | | — | Asp | — |
| +1 | | — | Leu | — |
| 26 | Arg | His | Ser | Ser |
| 27 | Glu | Gly | Leu | Gly |
| 28 | Phe | Val | Thr | Ser |
| 29 | Pro | His | Leu | Ile |
| 30 | Glu | Asp | Gln | Cys |
| 31 | Met | Leu | Ala | Thr |
| 32 | Asn | Phe | Thr | Cys |
| 33 | Leu | Leu | Ala | Ser |
| 56 | Leu | Phe | Phe | Val |
| 57 | Ile | Gly | Gly | Val |
| 58 | Ser | Asn | Tyr | Arg |
| 65° | Lys | Asn | Lys | Lys |
| 83 | Lys | Asn | Asn | Asn |
| 105 | Leu | His | Leu | Val |
| 106 | His | Met | Met | Met |
| 108 | Lys | Trp | Val | Leu |
| 109 | Pro | Thr | Leu | Pro |

°These amino acid substitutions arose from accidental mutations outside the randomized positions.
+2, +4 describe the insertion of two or 4 amino acids in loop 1 of the TLPC library described in Example 2.

Example 29

Production of the TLPC Muteins

For the preparative production of the anti hCD33 muteins S100.1 I08, S101.2 A20 and S101.2 O08 obtained from Example 28 the mutagenized coding region between the two BstXI cleavage sites was subcloned from the vector pTLPC12 (FIG. 7) on the expression plasmid pTLPC14 (FIG. 21). The obtained plasmid thus encoded a fusion protein of the mutein with the OmpA signal sequence and the T7-tag at the N-terminus as well as the STREP-TAG® II at the C-terminus.

Single colonies of E. coli-W3110 (fermentation) or E. coli-JM83 (shaker flask expression) were transformed with the pTLPC14 plasmids coding for the TLPC muteins S100.1 I08, S101.2 A20 or S101.2 O08, respectively. The shaker flask expression, the 1 l fermentation, the SA-chromatography and the size exclusion chromatography (SEC) were performed as described in Example 5. The SEC revealed a dimeric and a monomeric protein fraction for the clones S100.1-I08 and S101.2 O08. The binding affinity of monomeric and dimeric fraction was separately determined in an ELISA.

Example 30

Measurement of the Affinity of the TLPC Muteins in ELISA

For the determination of binding affinity of the selected TLPC muteins from Example 28 for the prescribed protein target hCD33-Fc as well as the unrelated control proteins in an ELISA the wells of black Fluotrac 600 ELISA plates (Greiner; 384 well) were coated with 20 µl hCD33-Fc (1 µg/ml), AffiniPure mouse anti-human IgG Fc$_{Gamma}$ fragment-specific antibody (5 μg/ml, Jackson ImmunoResearch) and as a control, with hIgG1 (10 μg/ml, Jackson ImmunoResearch) O/N at 4° C. The targets hCD33-Fc (1 μg/ml, R&D Research) and hCD22-Fc (1 μg/ml, Peprtoech) were captured via the AffiniPure mouse anti-human IgG Fc$_{Gamma}$ fragment-specific antibody for 1 h at RT. Afterwards, the ELISA was performed with the TLPC muteins from Example 29 as described in Example 10.

Figure 22:
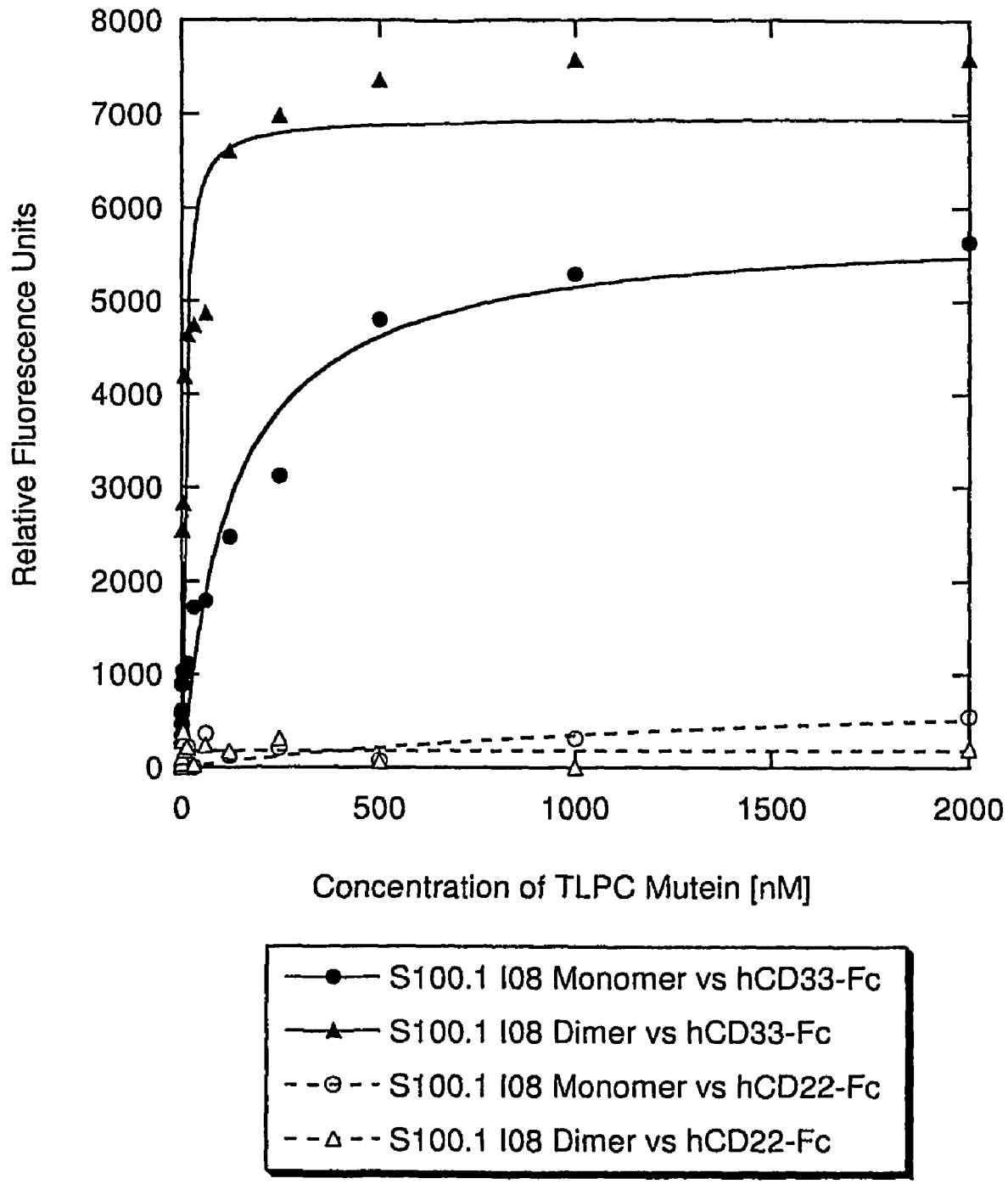
FIG. 22 depicts the binding of the TLPC mutein S100.1 I08 monomer and dimer to hCD33-Fc in an ELISA.
Figure 23:
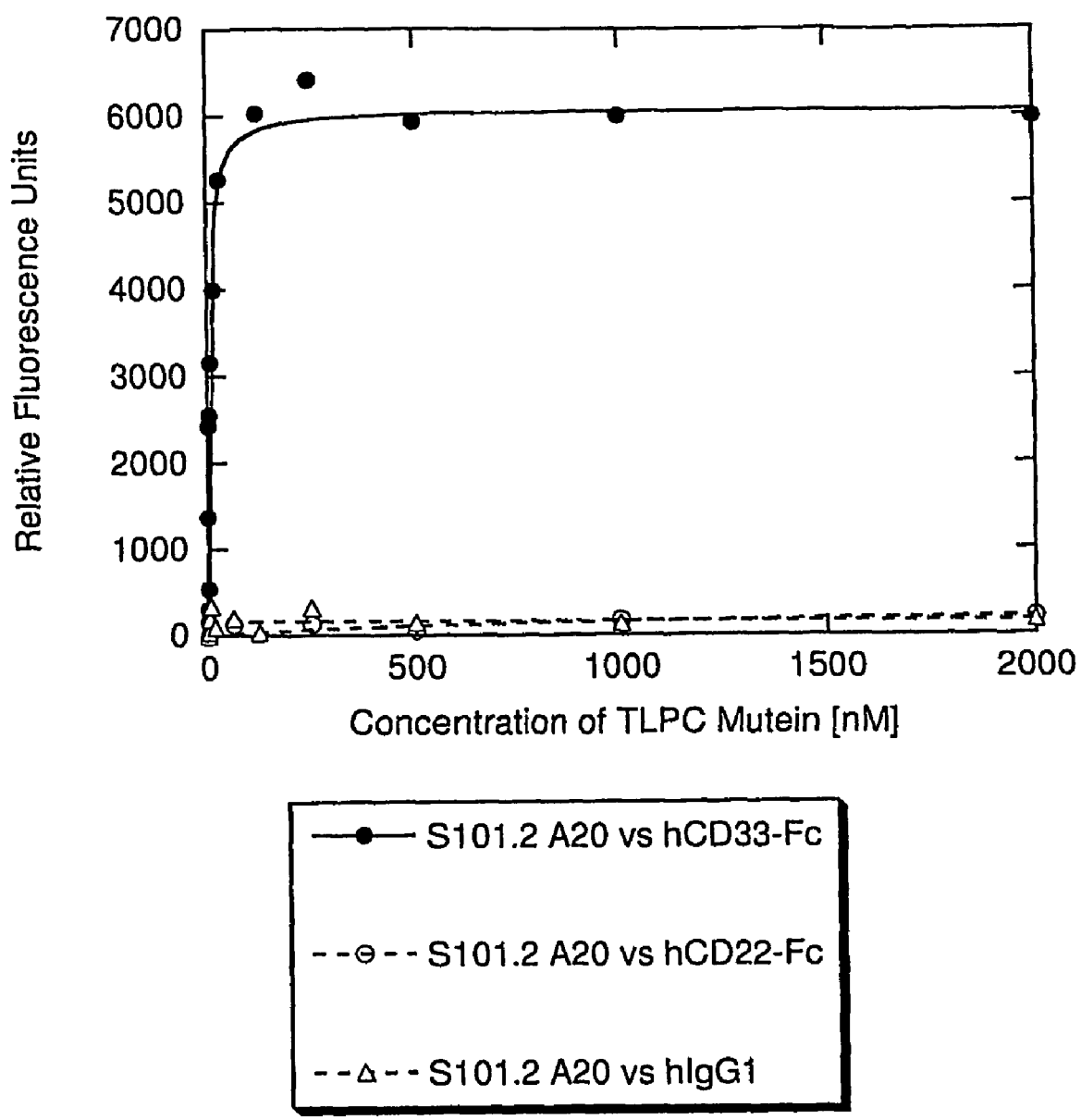
FIG. 23 depicts the binding of the TLPC mutein S101.2 A20 to hCD33-Fc in an ELISA.
Figure 24:
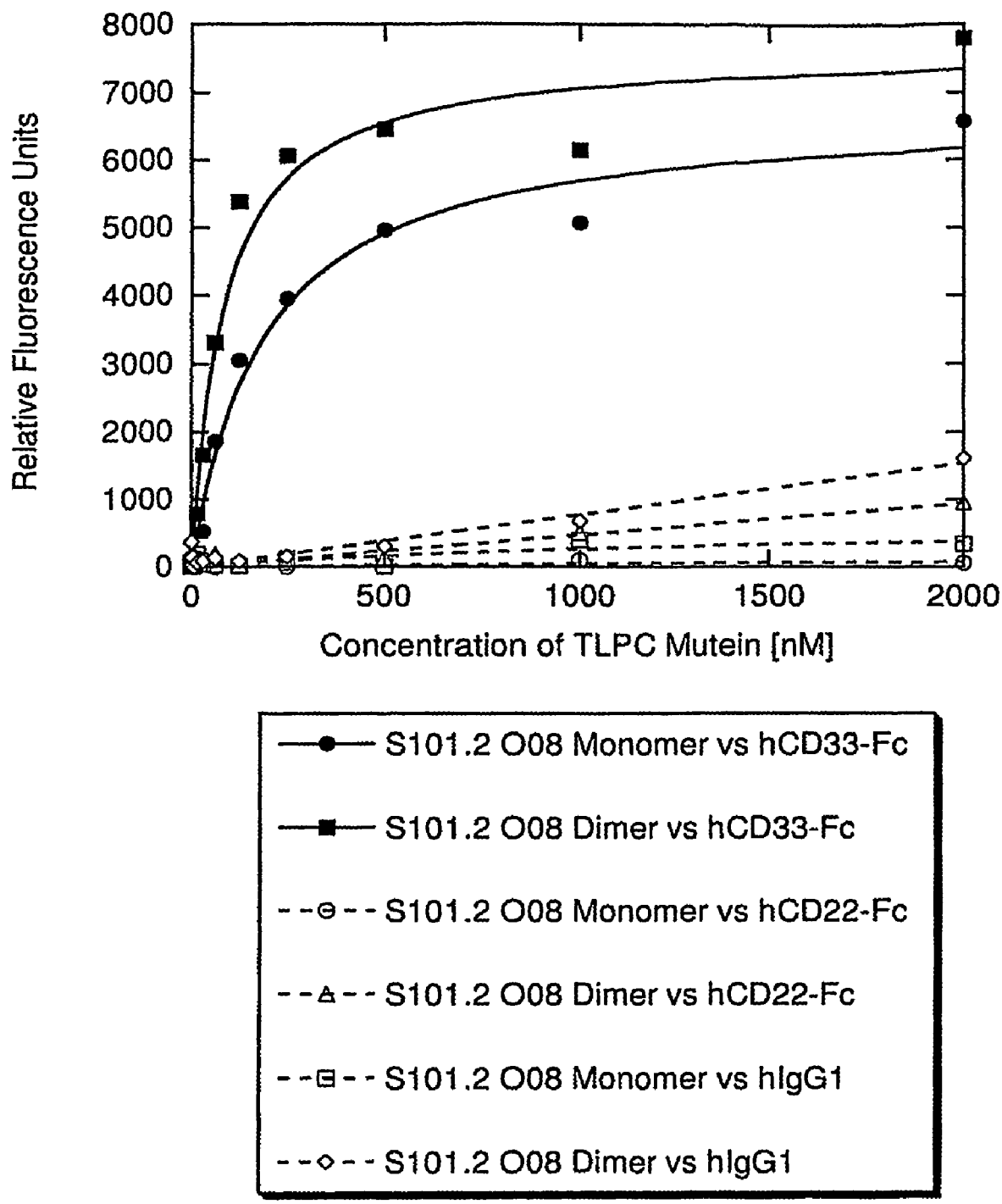
FIG. 24 depicts the binding of the TLPC mutein S101.2 O08 monomer and dimer to hCD33-Fc in an ELISA.

The resulting binding curves were fitted as described in Example 10 and are depicted in FIGS. 22-24. The values obtained for the apparent dissociation constants of the complexes between the TLPC muteins and the target protein hCD33-Fc as well as complexes between the TLPC muteins and the control proteins hCD22-Fc (R&D Systems) and HSA (Sigma) are summarized in Table 12.

TABLE 12

Affinity binding constants of the TLPC muteins

| TLPC mutein, monomer | $K_D$[nM]hCD33-Fc | $K_D$[nM]hCD22-Fc | $K_D$[nM] hIgG1 |
|---|---|---|---|
| CD33 S101.2 A20 | 5.2 ± 0.72 | —* | —* |
| CD33 S101.2 O08 (monomer) | 187 ± 26.9 | —* | —* |
| CD33 S100.1 I08 (monomer) | 131 ± 38.8 | —* | ND |
| CD33 S101.2 O08 (dimer) | 83 ± 13.7 | —* | —* |
| CD33 S100.1 I08 (dimer) | 6.3 ± 1.4 | —* | ND |

*No detectable binding activity;
ND = not determined

Example 31

Figure 25:
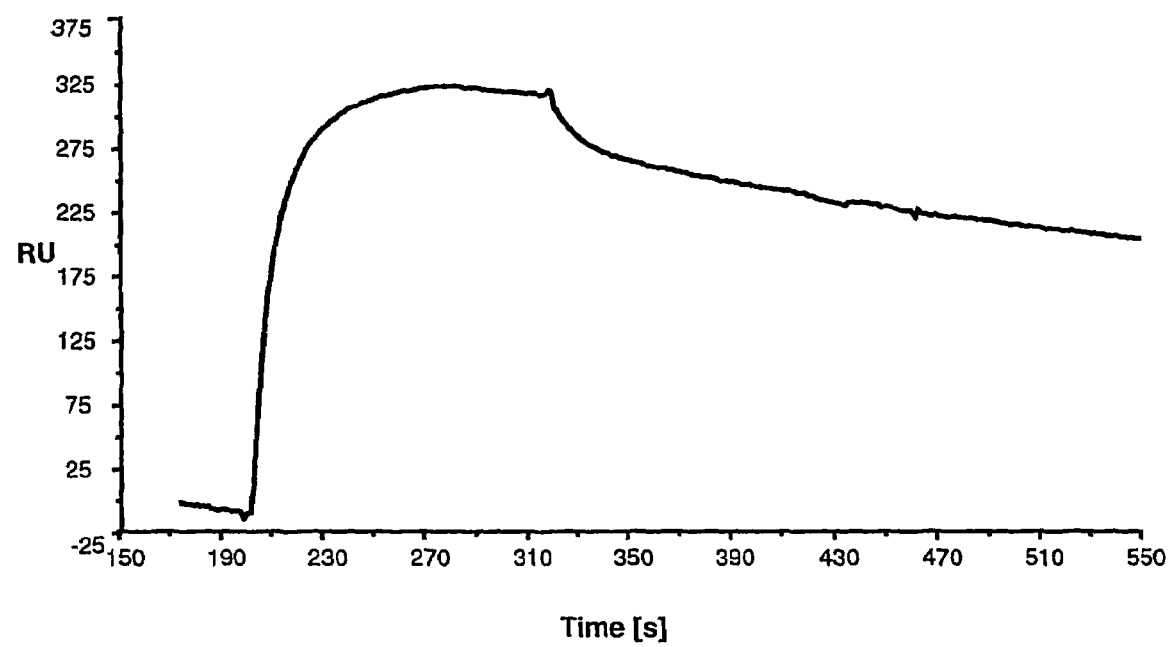
FIG. 25 depicts the binding of the TLPC mutein S100.1 I08 Dimer to hCD33-Fc in BIAcore experiments.
Figure 26:
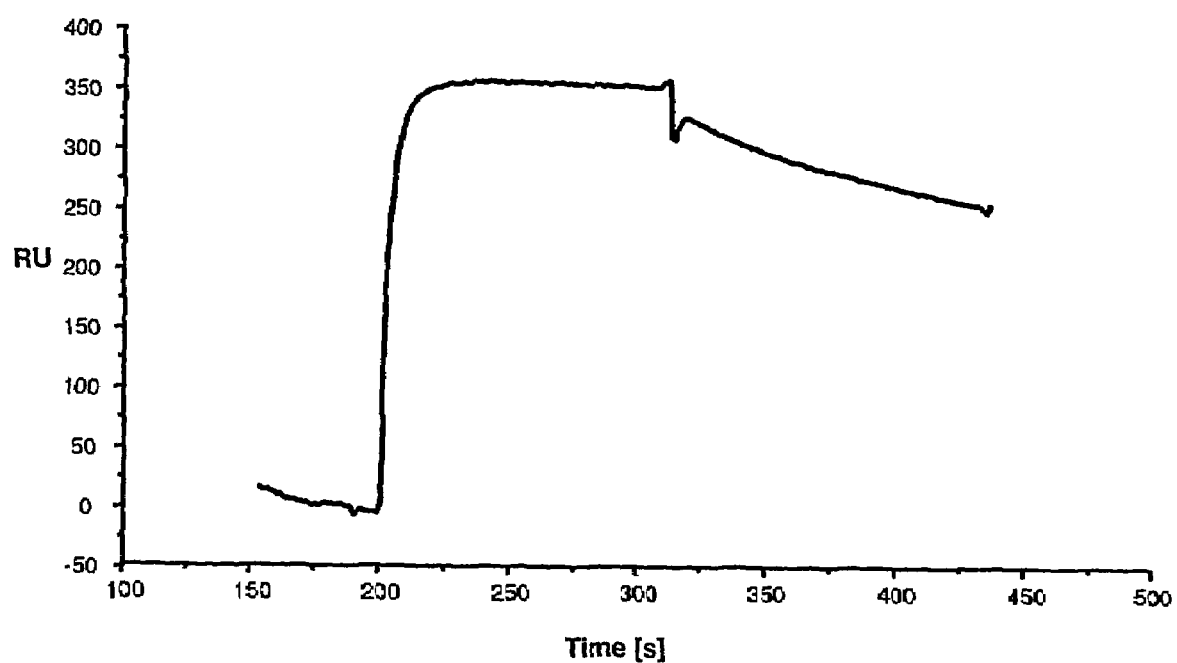
FIG. 26 depicts the binding of the TLPC mutein S101.2 A20 to hCD33-Fc in BIAcore experiments.
Figure 27:
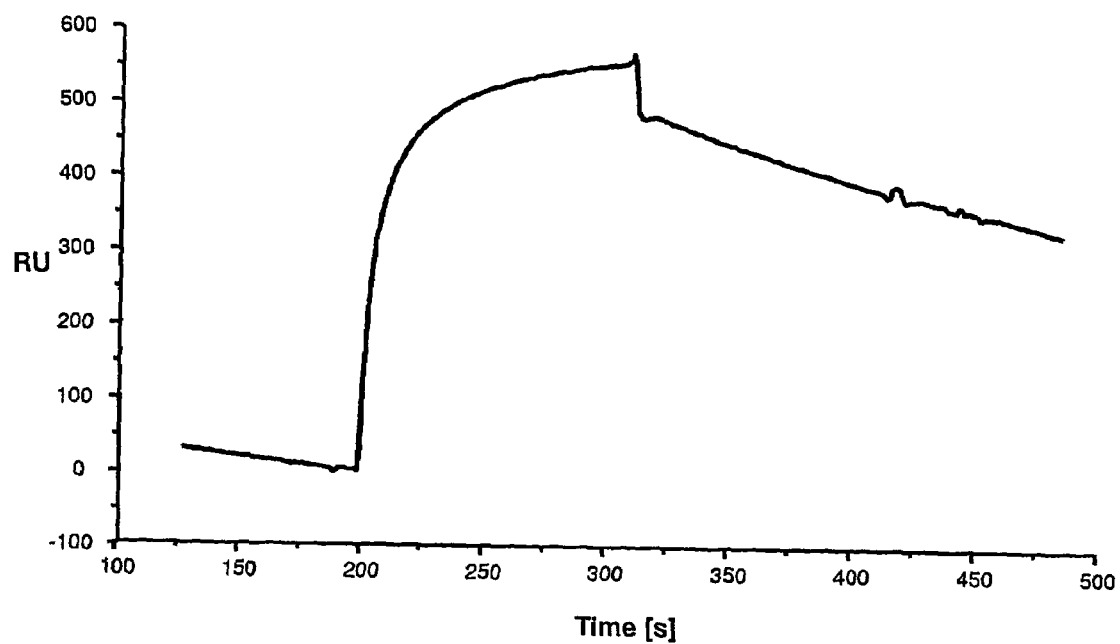
FIG. 27 depicts the binding of the TLPC mutein S101.2 O08 to hCD33-Fc in BIAcore.

Measurement of the Affinity of the TLPC Muteins in BIAcore 14000 response units (RU) AffiniPure mouse anti-human IgG Fc Gamma fragment-specific antibody (Jackson Immunoresearch) were coupled by amine coupling to a CM5 sensor chip (Biacore) according to the manufacturers' recommendations. 3000RU hCD33-Fc (R&D research) were captured to this surface by injecting 10 μl of a 0.2 mg/ml hCD33-Fc solution at a flow rate of 2 μl/min. BBS (10 mM HEPES, 150 mM NaCl, 2 mM EDTA, 0.005% v/v Tween pH 7.4) was used as running buffer. All samples were diluted in this running buffer. The TLPC muteins, obtained in example 29, were added to the hCD33-Fc captured surface by injection of a 40 μl sample with a 20 μl/min flow rate. The solutions of added TLPC mutein were 10 μM and 6.4 μM for S101.2 A20 and S101.2 O08, respectively. The surface of the chip was regenerated with 10 mM HCl followed by recoupling of hCD33-Fc before the next lipocalin mutein was measured. All measurements were performed on a BIAcore X apparatus. To determine the binding affinity of S100.1 I08 2000 RU of hCD33-Fc were captured to the surface described above and the solution of the lipocalin mutein added had a concentration of 5 μM. The obtained binding curves were fitted using the BIAevaluation software 3.1 from Biacore and are shown in FIGS. 25-27. The resulting affinity binding constants of the TLPC muteins are summarized in Table 13.

TABLE 13

Affinity binding constants of the TLPC muteins

| TLPC mutein | $k_{on}$ [M$^{-1}$s$^{-1}$] | $k_{off}$[s$^{-1}$] | $K_D$ [nM]hCD33-Fc |
|---|---|---|---|
| CD33 S101.2 A20 | 2.3 × 10$^4$ | 2.0 × 10$^{-3}$ | 87 |
| CD33 S101.2 O08 | 1.3 × 10$^4$ | 1.9 × 10$^{-3}$ | 146 |
| CD33 S100.1 I08 | 1.5 × 10$^4$ | 8.5 × 10$^{-4}$ | 57 |

What is claimed is:

1. A mutein of human tear lipocalin, wherein the mutein comprises at least 12-16 amino acid mutations with respect to the wild type amino acid sequence of mature human tear lipocalin as set forth in SEQ ID NO: 58 wherein said mutations are selected from any of amino acids 25, 26, 27, 28, 29, 30, 31, 32, 33, 56, 57, 58, 83, 105, 106, 108 and 109, and wherein said mutein possesses at least 80% sequence identity with SEQ ID NO: 58 and binds a given non-natural target of human tear lipocalin with detectable affinity.

2. The mutein of claim 1, wherein the mutein comprises at least any 16 amino acid mutations at any of the sequence positions 25, 26, 27, 28, 29, 30, 31, 32, 33, 56, 57, 58, 83, 105, 106, 108 and 109 of the linear polypeptide sequence of the mature wild-type form of human tear lipocalin set forth in SEQ ID NO: 58.

3. The mutein of claim 1, further comprising 12-16 additional amino acid mutations selected from any of amino acids 8, 9, 10, 11, 12, 13, 43, 45, 47, 70, 72, 74, 75, 90, 92, 94, and 97.

4. The mutein of claim 1, wherein the mutein is conjugated to a label selected from the group consisting of: organic molecules, enzyme labels, radioactive labels, colored labels, fluorescent labels, chromogenic labels, luminescent labels, haptens, digoxigenin, biotin, metal complexes, metals, and colloidal gold.

5. The mutein of claim 1, wherein the mutein is fused at its N-terminus or its C-terminus to a protein, a protein domain or a peptide.

6. A method for the generation of a mutein of human tear lipocalin of claim 1, comprising: (a) subjecting a nucleic acid molecule encoding a human tear lipocalin to mutagenesis and changing at least 12-16 codons of the corresponding sequence positions encoding amino acids 25, 26, 27, 28, 29, 30, 31, 32, 33, 56, 57, 58, 83, 105, 106, 108 and 109 of the linear polypeptide sequence of human tear lipocalin according to SEQ ID NO: 58, (b) expressing at least one mutein nucleic acid molecules obtained in (a) in a suitable expression system, and (c) enriching at least one mutein having a detectable binding affinity for a given target by means of selection and/or isolation.

7. A pharmaceutical composition comprising at least one mutein of claim 1.

8. The method of claim 6, further comprising subjecting before or in step (a) or after step (c) the nucleic acid molecule encoding human tear lipocalin to mutagenesis at least at 12-16 codons of any of the sequence positions 8, 9, 10, 11, 12, 13, 43, 45, 47, 70, 72, 74, 75, 90, 92, 94, and 97 of the linear polypeptide sequence of human tear lipocalin according to SEQ ID NO: 58.

* * * * *

UNITED STATES PATENT AND TRADEMARK OFFICE
CERTIFICATE OF CORRECTION

| | | |
|---|---|---|
| PATENT NO. | : 7,585,940 B2 | Page 1 of 1 |
| APPLICATION NO. | : 10/569134 | |
| DATED | : September 8, 2009 | |
| INVENTOR(S) | : Skerra et al. | |

It is certified that error appears in the above-identified patent and that said Letters Patent is hereby corrected as shown below:

On the cover page,

[*] Notice:  Subject to any disclaimer, the term of this patent is extended or adjusted under 35 USC 154(b) by 336 days.

Delete the phrase "by 336 days" and insert -- by 529 days --

Signed and Sealed this

Tenth Day of August, 2010

David J. Kappos
*Director of the United States Patent and Trademark Office*